US007129039B2

(12) United States Patent
Ariizumi et al.

(10) Patent No.: US 7,129,039 B2
(45) Date of Patent: Oct. 31, 2006

(54) UNIQUE DENDRITIC CELL-ASSOCIATED C-TYPE LECTINS, DECTIN-1 AND DECTIN-2; COMPOSITIONS AND USES THEREOF

(75) Inventors: Kiyoshi Ariizumi, Dallas, TX (US); Akira Takashima, Irving, TX (US)

(73) Assignee: Board of Regents The University of Texas System, Austin, TX (US)

( * ) Notice: Subject to any disclaimer, the term of this patent is extended or adjusted under 35 U.S.C. 154(b) by 732 days.

(21) Appl. No.: 10/201,060

(22) Filed: Jul. 23, 2002

(65) Prior Publication Data
US 2006/0074007 A1 Apr. 6, 2006

Related U.S. Application Data

(62) Division of application No. 09/396,492, filed on Sep. 14, 1999, which is a division of application No. 08/772,440, filed on Dec. 20, 1996, now Pat. No. 6,046,158.

(51) Int. Cl.
C12Q 1/00 (2006.01)
G01N 33/53 (2006.01)

(52) U.S. Cl. .......................... 435/4; 436/501
(58) Field of Classification Search .............. 435/4; 436/501
See application file for complete search history.

(56) References Cited

U.S. PATENT DOCUMENTS

| 5,199,942 A | 4/1993 | Gillis ................... 604/4.01 |
| 5,434,340 A | 7/1995 | Krimpenfort et al. ......... 800/2 |
| 5,470,952 A | 11/1995 | Stahl ..................... 530/350 |
| 5,530,179 A | 6/1996 | Terhorst et al. ............. 800/2 |
| 5,557,032 A | 9/1996 | Mak ....................... 800/2 |
| 6,300,090 B1 * | 10/2001 | Steinman et al. ......... 435/7.24 |

FOREIGN PATENT DOCUMENTS

| WO | WO 96/23882 | 8/1992 |
| WO | WO 95/29236 | * 11/1995 |
| WO | WO 98/02456 | 1/1998 |

OTHER PUBLICATIONS

Willment et al (Journal of Biological Chemistry, 2001, vol. 276, pp. 43818-43823).*
Ariizumi, et al., "Cloning of Novel C-Type Lectins That Are Expressed Selectively By Dendritic Cells," *The Journal of Investigative Dermatology*, 106(4):814, Abstract No. 52, Apr. 1996.
Benzouska et al., "Rat Natural Killer Cell Antigen, NKR-P1, Related to C-Type Animal Lectins Is a Carbohydrate-Binding Protein," *The Journal of Biological Chemistry*, 269(24):16945-16952, Jun. 1994.
Benzouska, "C-Type Lectins of Natural Killer Cells: Carbohydrate Ligands and Role in Tumor Cell Lysis," *Biochemical Society Transactions*, 24:156-161, 1996.
Bernhard et al., "Dendritic cells lose ability to present protein antigen after stimulating antigen-specific T cell responses, despite upregulation of MHC expression," *Immunobiology*, 201:568-582, 2000.
Bieber et al., "CD69, an early activation antigen on lymphocytes, is constitutively expressed by human epidermal langerhans cells," *J. Investigative Dermatology*, 98:771-776, 1992.
Chang et al., "Molecular Characterization of Human CD94: A Type II Membrane Glycoprotein Related to the C-Type Lectin Superfamily," *Eur. J. Immunol.*, 25:2433-2437, 1995.
Cherayil, Weiner and Pillai, "The Mac-2 Antigen Is a Galactose-Specific Lectin That Binds IgE." *J. Exp. Med.*, 170:1959-1972, Dec. 1989.
Davis et al., "Direct gene transfer into skeletal muscle in vivo: factors affecting efficiency of transfer and stability of expression," *Human Gene Therapy*, 4:151-159, 1993.
Dietz and Vuk-Pavlovic. "High efficiency adenovirus-mediated gene transfer to human dendritic cells," *Blood*, 91(2):392-398, 1998.
Erard et al., "Interleukin 2 Is Both Necessary and Sufficient For the Growth and Differentiation of Lectin-Stimulated Cytolytic T Lymphocyte Precursors," *The Journal of Immunology*, 134(3):1644-1652, Mar. 1985.
Ezekowitz et al., "A Human Mannose-Binding Protein Is an Acute-Phase Reactant That Shares Sequence Homology with other Vertebrate Lectins," *J. Exp. Med.*, 167:1034-1046, Mar. 1988.
Hamann et al., "Expression Cloning of the Early Activation Antigen CD69, A Type II Intgral Membrane protein with a C-Type Lectin Domain," *The Journal of Immunology*, 150(11):4920-4927, Jun. 1993.

(Continued)

*Primary Examiner*—Karen A. Canella
(74) *Attorney, Agent, or Firm*—Fulbright & Jaworski LLP

(57) ABSTRACT

Novel genes expressed selectively by long-term dendritic cell (DC) lines (XS series) from murine epidermis which retain important features of resident epidermal Langerhans cells (LC) are provided. These genes encode distinct type II membrane-integrated polypeptides, each consisting of a cytoplasmic domain, a transmembrane domain, an extracellular connecting domain, and a C-terminal extracellular domain that exhibits significant homology to the carbohydrate recognition domains (CRD) of C-type lectins. Expression of both genes is highly restricted to cells of DC lineage (including epidermal LC). Thus, these genes encode new, DC-specific members of the C-type lectin family, now termed "DC-associated C-type lectin-1 and -2" (dectin-1 and dectin-2). Two isoforms of the dectin-1 molecule and five isoforms of the dectin-2 molecule have also been identified. The invention further provides His-tagged fusion proteins comprising 6× histidine and the extracellular domain of dectin-1 or dectin-2. Also provided are antibodies raised to synthetic peptides designed from the dectin-1 sequence or to the His-tagged fusion proteins described.

8 Claims, 15 Drawing Sheets

OTHER PUBLICATIONS

Komatsubare et al., Immortalization of murine leukocytes by oncogenes II. Phenotypic characterization of transformants, immortalized by v-src of Ha-ras oncogenes: expression of B220, a b-cell lineage specific antigens, *Microbiol. Immunol.*, 32(8):869-875, 1988.

Lanier et al., "A Disulfide_Linked Homodimer of the C-Type Lectin Superfamily Expressed by a Subset of NK and T Lymphocytes," *The Journal of Immunology*, 153:2417-2428, 1994.

Licastro et al., "Lectins and Superantigens: Membrane Interactions of These Compounds with T Lymphocytes Affect Immune Responses," *Int. J. Biochem.*, 25(6):845-852, 1993.

Lopez-Cabrera et al., "Molecular Cloning, Expression, and Chromosomal Localization of the Human Earliest Lymphocyte Activation Antigen AIM/CD69, a New Member of the C-Type Animal Lectin Superfamily of Signal Transmitting Receptors," *J. Exp. Med.*, 178 537-547, Aug. 1993.

Lopez-Cabrera et al., "Transcriptional regulation of the gene encoding the human c-tpe lectin leukocyte receptor AIM/CD69 and functional characterization of its tumor necrosis factor α-responsive elements."*J. Biol. Chem.*, 270(37):21545-21551,1995.

Panelli et al., "Phase 1 study in patients with metastatic melanoma of immunization with dendritic cells presenting epitopes derived from the melanoma-associated antigens MART-1 and gp100,"*J. Immunotherapy*, 23:487-498, 2000.

Paul, In *Fundamental Immunology*, 3rd edition, pp. 119-121, 409, 1993.

Rodriguez et al., "Selective transport of internalized antigens to the cytosol for MHC presentation in dendritic cells," *Nature Cell Biology*, 1:362-368, 1999.

Roosnek et al., "T Cell Triggering By Lectins II. Stimuli For Induction of Interleukin 2 Responsiveness and Interleukin 2 Production Differ Only in Quantitative Aspects." *Eur. J. Immunol.*, 15:657-661, 1985.

Rothman et al., "Heart muscle-specific gene expression using relication defective recombinant adenovirus," *Gene Therapy*, 3:919-926, 1996.

Sowalsky and Fox, "Pattern of Lectin Binding to Murine T Lymphocytes," *Immunology*, 75:92-98, 1992.

Steinman and Swanson, "The Endocytic Activity of Dendritic Cells," *J. Exp. Med.*, 182:283-288, Aug. 1995.

Suzuki et al., "Molecular Cloning and Expression of cDNA Encoding Human Macrophage C-Type Lectin," *The Journal of Immunology*, 156:128-135, 1996.

Turley et al., "Transport of peptide-MHC complexes in developing dendritic cells," *Science*, 288:522-527, 2000.

Zitvogel et al., "IL-12-engineered dendritic cells serve as effective tumor vaccine adjuvants in vivo," *Ann NY Acad Sci*, 795:284-293, 1996.

Ariizumi et al., "Subtractive cloning of dendritic cell-specific genes: identification of novel C-type lectins," *FASEB*, 10(6) A1213, Abstract # 1236, 1996.

Bobek et al., "Schistosoma japonicum: analysis of eggshell protein genes, their expression, and comparison with similar genes form other schistosomes," *Experimental Parasitology*, 72:381-390, 1991.

Cameron et al., "Genetic analysis, nucleotide sequence, and products of two *Pseudomonas denitrificans* cob genes encoding nicotinate-nucleotide: dimethylbenzimidazole phosphoribosyltransferase and cobalamin (5'-phosphate) synthase," *J. of Bacteriology*, 173(19):6066-6073, 1991

Dectin-1 (Seq ID No. 2) compared to Dectin-2 (Seq ID No. 4).

Drake and Koomey, "The product of the pilQ gene is essential for the biogenesis of type IV pili in *Neisseria gonorrhoeae,"Molecular Microbiology*, 18(5):975-986, 1995.

Eckhardt et al., "Characterization of the promoter, signal sequence, and amino terminus of a secreted β-galactosidase form *Streptomyces lividans,"J. of Bacteriology*, 169(9):4249-4256, 1987.

Falk et al., "Allele-specific motifs revealed by sequencing of self-peptides eluted from MHC molecules," *Nature*, 351:290-296, 1991.

GenBank Accession No. S4868, A41970, A44922, F69713, A22867, A14997, A12030, A34412, S39414, A00925, A22867, C69549, A25285, A28013.

Raaphorst et al., "Restricted utilization of germ-like $V_H3$ genes and short diverse third complementarity-determining regions (CDR3) in human fetal B lymphocyte immunoglobulin heavy chain rearrangements," *Eur. J. Immunology*, 22:247-251, 1992.

Showalter et al., "Tomato extensin and extensin-like cDNAs: structuer and expression in response to wounding," *Plant Molecular Biology*, 16:547-565, 1991.

\* cited by examiner

|   |   | Cytoplasmic domain | | Transmembrane domain |
|---|---|---|---|---|
| 1 | ▽ MKYHSHIENLDEDGYTQLDFSTQDIHKRPRGSEKGSRAPSSPWR | 44 | PIAVGLGILCFVVVVAAVLGALA | 68 |
| 69 | FWRHNSGRNPEEKDNFLSRNKENHKPTESSLDEKVAPSKASQTTGGFSQS | 118 | | |
|   |   | CRD | | |
| 119 | \* \* CLPNWIMHGKSCYLFSFSGNSWYGSKRHCSQLGAHLLKIDNSKEFEFIESQTSSHRINAFWIG | 181 | | |
| 182 | \* ▶ \* LSRNQSEGPWFWEDGSAFFPNSFQVRNTVPQESLLHNCVWIHGSEVYNQICNTSSYSICEKEL | 244 | | |

FIG. 1A

```
              *      *      *            *       *
Dectin-1  CLPNWIMHGKSCYLFSFSGNSWYGSKRHCSQLGAHLLKIDNSKEF
hHL1      CPVNWVEHERSCYWFSRSGKAWADADNYCRLEDAHLVVVTSWEEQ
rHL2      CPVNWVEFGGSCYWFSRDGLTWAEADQYCQMENAHLLVINSREEQ
hHL2      CPVNWVEHQGSCYWFSHSGKAWAEAEKYCQLENAHLVVINSWEEQ
mCD23     CPKNWLHFQQKCYMFGKGSKQWIQARFACSDLQGRLVSIHSQKEQ
hCD69     CSEDWVGYQRKCYFISTVKRSWTSAQNACSEHGAILAVIDSEKDM

*   *                   *          *
Dectin-1  EFIESQTSSHRINAFWIGLSRNQSEGPWFWEDGSAFFPNSFQVRN
hHL1      KFVQHHIGEVNT---WMGLHD--QNGPWKWVDGTDY-ETGFKNWR
rHL2      EFVVKHRGAFHT---WIGLTD--KDGSWKWVDGTEY-RSNFKNWA
hHL2      KFIVQHTNPFNT---WIGLTD--SDGSWKWVDGTDY-RHNYKNWA
mCD23     DFLMQHINKKDS---WIGLQDLNMEGEFVWSDGS---PVGYSNWN
hCD69     NFLKRYAGR---EEHWVGLKK-EPGHPWKWSNGKEF---------

*           *
Dectin-1  TVPQESLL-------HNCVWIHGSEVYNQ-ICNTSSYS-ICEKEL
hHL1      PFQPDWYGHGLGGGEDCAHFTDDGWNDDVCQR-PYRWVCETEL
rHL2      FTQPDNWQGHEEGGSEDCAEILSDGLWNDNFCQQ-VNRWACERKR
hHL2      VTQPDNWHGHELGGSEDCVEVQPDGRWNDDFCIQ-VYRWVCEKRR
mCD23     EGEPNN------GGQGEDCVMMRGSGQWNDAFCRSYLDAWVCE-QL
hCD69     ----NNWF--NVTGSDKCVFLKNTEVSSME-CEKNLY-WICNKPY
```

FIG. 1B

SEQUENCE LISTING (1) GENERAL INFORMATION:

(iii) NUMBER OF SEQUENCES: 42

(2) INFORMATION FOR SEQ ID NO: 1:

(i) SEQUENCE CHARACTERISTICS:
      (A) LENGTH: 2298 base pairs
      (B) TYPE: nucleic acid
      (C) STRANDEDNESS: single
      (D) TOPOLOGY: linear (ix) FEATURE:
      (A) NAME/KEY: modified_base
      (B) LOCATION: 1966
      (D) OTHER INFORMATION: /mod_base= OTHER
         /note= "Y = C or T"

(xi) SEQUENCE DESCRIPTION: SEQ ID NO: 1:

```
GGGTTTGGCT TAGTGAGCCT CATCCTGGCA GTTATTTTAC TAGTAAAGAA CATTCAAGTG      60

CTCTGCCTAC CTAGGGCCCT GTGAAGCAAT GAAATATCAC TCTCATATAG AGAATCTGGA     120

TGAAGATGGA TATACTCAAT TAGACTTCAG CACTCAAGAC ATCCATAAAA GGCCCAGGGG     180
```

-continued

```
ATCAGAGAAA GGAAGCCGGG CTCCATCTTC ACCTTGGAGG CCCATTGCAG TGGGTTTAGG        240

AATCCTGTGC TTTGTGGTAG TAGTGGTTGC TGCAGTGCTG GGTGCCCTAG CATTTTGGCG        300

ACACAATTCA GGGAGAAATC AGAGGAGAA AGACAACTTC CTATCAAGAA ATAAAGAGAA         360

CCACAAGCCC ACAGAATCAT CTTTAGATGA GAAGGTGGCT CCCTCCAAGG CATCCCAAAC        420

TACAGGAGGT TTTTCTCAGT CTTGCCTTCC TAATTGGATC ATGCATGGGA AGAGCTGTTA        480

CCTATTTAGC TTCTCAGGAA ATTCCTGGTA TGGAAGTAAG AGACACTGCT CCCAGCTAGG        540

TGCTCATCTA CTGAAGATAG ACAACTCAAA AGAATTTGAG TTCATTGAAA GCCAAACATC        600

GTCTCACCGT ATTAATGCAT TTTGGATAGG CCTTTCCCGC AATCAGAGTG AAGGGCCATG        660

GTTCTGGGAG GATGGATCAG CATTCTTCCC CAACTCGTTT CAAGTCAGAA ATACAGTTCC        720

CCAGGAAAGC TTACTGCACA ATTGTGTATG GATTCATGGA TCAGAGGTCT ACAACCAAAT        780

CTGCAATACT TCTTCATACA GTATCTGTGA GAAGGAACTG TAAATGTATG TGAGAATATA       840

AAGATGGTGT GTGTGTGTGT GTGTGTGTGT GTACATGCAC ACACACCACC ACCACCACCA        900

CTACCAACAA CAGAACAGAA CAGAACAGAA CAGAACAGAA CAGAACAGAT TAATATTAAA        960

AAACAGAAAA AATGCTGGGA TGCTAAGAGA CTTTAACCTC ATTTGAGAAC TTGGATGAAG       1020

AAGCTGAGAC TTTTGTACTT GTCATCTTCA CAAAGATGGT GGCACTATCT TCCAGTTAGG       1080

AAGTCACTAG ACATGGAGTG AGGGCAGCTC AACAATACAG AGAATATGTG AACCTGAGGT       1140

ACCCTGACTC AAATTTCACA ACCACAATGA AACCCCTACA CTATCAGGAA ACACTGTAGA       1200

GGAGTGAGAC TGAAGACTTT AAAAGCCAGA GAATCAGCCT ACTTACTGTG GTGTTTTCTA       1260

GACAGGACAG GGAAAGTATA TCTAGGAAAT AAAAACAATA CAATTCAGCA AACAAAATCT       1320

GCATAATGAC AACCTCAGTT GGTATGGTAT GTTATGGTAT GGTATGGGTG TAGAAGTTTC       1380

ACAAGGCCCT ATGAAGAACT ACAGACAGTT AAATAGGGGG AAAGCTTTTT CTAGGATCAA       1440

GCCTACTGAA CCCCAAGAAG TCAGCACTGA ACATATGTAC AGATCAGTAT CATTAAATGA       1500

ACTAGTAAGA CATATACATA TATGTTAATC AAATATTGGT ACCAGAGTAC ACACTGTGTT       1560

TGCATGATTT TCTCAGTATC TACAGTACAC CAGACACAGG GAGAAGGCAA AATGAACTTC       1620

TAAATTGAGA AGTGAAAAAA ATGAGGAAAG AGAATCTTCA CCACAAATAG GGATTCTATT       1680

TTCACCCACA TGATCATTAT TAAGATGGCC ATCACCCAAA CGTCGTGACC CAAGCTACTT       1740

CCTCAACTAG ATAACTCAAA GAGTCTGCCC ACCTTTTCTG ATAGCAAATC TGGTATCTAG       1800

ATTTCACTGT TTCCTTATGC TGTCTGGCCA GCAGTATGAC AAAGGTGCTG CCCTTTCAGG       1860

AAGCAGTCTC CTTAAATGCT GTAGTTGGAA AGATAAATCA TATCTGATAG TGAATATTTA       1920

AAAAGCGCCC AGTCAGGATA AGTGTTTTGG AACACAGAAC ATATTYCATC TTTTTATGAT       1980

ACACTATCTT GCAATTAACA ACCAATTCTT AAGTCATTTC TTTACAAACA TATGACTGGA       2040

ATATGACTGT TTCCTAGTGT GATCTGTCTT GTTAACTTCT AAGATTGTCC ATTAATACCA       2100

CCCTTATTTC CAGTGTGGAC TTCCAAATTG CTGGGGATCT GTTTATAGCT TTCTCAGACT       2160

AATCAATATG TGGGCAGAAA TTGTGCTGAG TCCACTGAAT TGTTCTCTTG AAAATGATTG       2220

GGTTTATGTC ACTTTCATCT CAATTGAAAA ACTGCTTATT AAAGTATCTT TGGCCTCTGA       2280

AAAAAAAAAA AAAAAAAA                                                     2298
```

(2) INFORMATION FOR SEQ ID NO: 2:

(i) SEQUENCE CHARACTERISTICS:
        (A) LENGTH: 244 amino acids
        (B) TYPE: amino acid
        (C) STRANDEDNESS: <Unknown>

(D) TOPOLOGY: linear (xi) SEQUENCE DESCRIPTION: SEQ ID NO: 2:

```
Met Lys Tyr His Ser His Ile Glu Asn Leu Asp Glu Asp Gly Tyr Thr
1               5                   10                  15

Gln Leu Asp Phe Ser Thr Gln Asp Ile His Lys Arg Pro Arg Gly Ser
                20                  25                  30

Glu Lys Gly Ser Arg Ala Pro Ser Ser Pro Trp Arg Pro Ile Ala Val
            35                  40                  45

Gly Leu Gly Ile Leu Cys Phe Val Val Val Val Ala Ala Val Leu
        50                  55                  60

Gly Ala Leu Ala Phe Trp Arg His Asn Ser Gly Arg Asn Pro Glu Glu
65                  70                  75                  80

Lys Asp Asn Phe Leu Ser Arg Asn Lys Glu Asn His Lys Pro Thr Glu
                85                  90                  95

Ser Ser Leu Asp Glu Lys Val Ala Pro Ser Lys Ala Ser Gln Thr Thr
                100                 105                 110

Gly Gly Phe Ser Gln Ser Cys Leu Pro Asn Trp Ile Met His Gly Lys
            115                 120                 125

Ser Cys Tyr Leu Phe Ser Phe Ser Gly Asn Ser Trp Tyr Gly Ser Lys
    130                 135                 140

Arg His Cys Ser Gln Leu Gly Ala His Leu Leu Lys Ile Asp Asn Ser
145                 150                 155                 160

Lys Glu Phe Glu Phe Ile Glu Ser Gln Thr Ser Ser His Arg Ile Asn
                165                 170                 175

Ala Phe Trp Ile Gly Leu Ser Arg Asn Gln Ser Glu Gly Pro Trp Phe
            180                 185                 190

Trp Glu Asp Gly Ser Ala Phe Phe Pro Asn Ser Phe Gln Val Arg Asn
        195                 200                 205

Thr Val Pro Gln Glu Ser Leu Leu His Asn Cys Val Trp Ile His Gly
    210                 215                 220

Ser Glu Val Tyr Asn Gln Ile Cys Asn Thr Ser Ser Tyr Ser Ile Cys
225                 230                 235                 240

Glu Lys Glu Leu
```

(2) INFORMATION FOR SEQ ID NO: 3:

(i) SEQUENCE CHARACTERISTICS:
        (A) LENGTH: 1227 base pairs
        (B) TYPE: nucleic acid
        (C) STRANDEDNESS: single
        (D) TOPOLOGY: linear (xi) SEQUENCE DESCRIPTION: SEQ ID NO: 3:

```
CATTGGCCCG CTCTGTGGCA TTTAACTCAA GTGTGTGTGG AAGTTGATTC TGAACTCTGG    60

CCTCTTTGAC AGAAGCCAGG TCCCTGAGTC GTATTTTGGA GACAGATGCA AGAAACCCCT   120

GACCTTCTGA ACATACACCT CAACAATGGT GCAGGAAAGA CAATCCCAAG GGAAGGGAGT   180

CTGCTGGACC CTGAGACTCT GGTCAGCTGC TGTGATTTCC ATGTTACTCT TGAGTACCTG   240

TTTCATTGCG AGCTGTGTGG TGACTTACCA ATTTATTATG GACCAGCCCA GTAGAAGACT   300

ATATGAACTT CACACATACC ATTCCAGTCT CACCTGCTTC AGTGAAGGGA CTATGGTGTC   360

AGAAAAAATG TGGGGATGCT GCCCAAATCA CTGGAAGTCA TTTGGCTCCA GCTGCTACCT   420

CATTTCTACC AAGGAGAACT TCTGGAGCAC CAGTGAGCAG AACTGTGTTC AGATGGGGGC   480

TCATCTGGTG GTGATCAATA CTGAAGCGGA GCAGAATTTC ATCACCCAGC AGCTGAATGA   540
```

```
GTCACTTTCT TACTTCCTGG GTCTTTCGGA TCCACAAGGT AATGGCAAAT GGCAATGGAT      600

CGATGATACT CCTTTCAGTC AAAATGTCAG GTTCTGGCAC CCCCATGAAC CCAATCTTCC      660

AGAAGAGCGG TGTGTTTCAA TAGTTTACTG AATCCTTCG AAATGGGGCT GGAATGATGT       720

TTTCTGTGAT AGTAAACACA ATTCAATATG TGAAATGAAG AAGATTTACC TATGAGTGCC      780

TGTTATTCAT TAATATCTTT AAAGTTCAGA CCTACCAAGA AGCCATAACT TCTTGGCCTG      840

TACATCTGAC AGAGGCCGTT CTTTTCCTAG CCACTATTCT TTACTCAAAC AGAATGAGCC      900

CTTTCTCCTT CTGATGGTTA GAGTTTTGTC AACTTGACAC AAACTAGAGT CACCTGGGGA      960

GTAGGATCTT CAGCTAAGGA ATTGCCTCTG TCAGCTTGAC CAGTCAGCAT GTCTGGGGGC     1020

ATTTTCTTGA TTAATGATTG TTGTAAGAGG GTCCAGGTGG TAAGCAAAGG TGTTAAACCC     1080

ATGAAGAGCA AGCCAGGGAG CATCATCCAT CCATCTCTGC CCTCAGGTTT CTGCCCCAGG     1140

GTCTTGCCCT GGTTTCTTTC TATGAACTGC TGTTACTTGA AAGTATAAGA TGAATAAACA     1200

ATTTCATCCA AAAAAAAAAA AAAAAAA                                         1227

(2) INFORMATION FOR SEQ ID NO: 4:

(i) SEQUENCE CHARACTERISTICS:
        (A) LENGTH: 209 amino acids
        (B) TYPE: amino acid
        (C) STRANDEDNESS: <Unknown>
        (D) TOPOLOGY: linear (xi) SEQUENCE DESCRIPTION: SEQ ID NO: 4:

Met Val Gln Glu Arg Gln Ser Gln Gly Lys Gly Val Cys Trp Thr Les
1               5                   10                  15

Arg Leu Trp Ser Ala Ala Val Ile Ser Met Leu Leu Ser Thr Cys
            20                  25                  30

Phe Ile Ala Ser Cys Val Val Thr Tyr Gln Phe Ile Met Asp Gln Pro
                35                  40                  45

Ser Arg Arg Leu Tyr Glu Leu His Thr Tyr His Ser Ser Leu Thr Cys
    50                  55                  60

Phe Ser Glu Gly Thr Met Val Ser Glu Lys Met Trp Gly Cys Cys Pro
65                  70                  75                  80

Asn His Trp Lys Ser Phe Gly Ser Ser Cys Tyr Leu Ile Ser Thr Lys
                85                  90                  95

Glu Asn Phe Trp Ser Thr Ser Glu Gln Asn Cys Val Gln Met Gly Ala
            100                 105                 110

His Leu Val Val Ile Asn Thr Glu Ala Glu Gln Asn Phe Ile Thr Gln
        115                 120                 125

Gln Leu Asn Glu Ser Leu Ser Tyr Phe Leu Gly Leu Ser Asp Pro Gln
    130                 135                 140

Gly Asn Gly Lys Trp Gln Trp Ile Asp Asp Thr Pro Phe Ser Gln Asn
145                 150                 155                 160

Val Arg Phe Trp His Pro His Glu Pro Asn Leu Pro Glu Glu Arg Cys
                165                 170                 175

Val Ser Ile Val Tyr Trp Asn Pro Ser Lys Trp Gly Trp Asn Asp Val
            180                 185                 190

Phe Cys Asp Ser Lys His Asn Ser Ile Cys Glu Met Lys Lys Ile Tyr
        195                 200                 205

Leu (2) INFORMATION FOR SEQ ID NO: 5:
```

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO: 5:

AGGCCCATTG CAGTGGGTTT AGGAATCCTG TGCTTTGTGG TAGTAGTGGT TGCTGCAGTG        60

CTGGGTGCCC TAGCA                                                        75

(2) INFORMATION FOR SEQ ID NO: 6:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear (xi) SEQUENCE DESCRIPTION: SEQ ID NO: 6:

Arg Pro Ile Ala Val Gly Leu Gly Ile Leu Cys Phe Val Val Val
1               5                   10                  15

Val Ala Ala Val Leu Gly Ala Leu Ala
            20                  25

(2) INFORMATION FOR SEQ ID NO: 7:

(i) SEQUENCE CHARACTERISTICS:
        (A) LENGTH: 528 base pairs
        (B) TYPE: nucleic acid
        (C) STRANDEDNESS: single
        (D) TOPOLOGY: linear (xi) SEQUENCE DESCRIPTION: SEQ ID NO: 7:

TTTTGGCGAC ACAATTCAGG GAGAAATCCA GAGGAGAAAG ACAACTTCCT ATCAAGAAAT        60

AAAGAGAACC ACAAGCCCAC AGAATCATCT TTAGATGAGA AGGTGGCTCC CTCCAAGGCA       120

TCCCAAACTA CAGGAGGTTT TTCTCAGTCT TGCCTTCCTA ATTGGATCAT GCATGGGAAG       180

AGCTGTTACC TATTTAGCTT CTCAGGAAAT TCCTGGTATG GAAGTAAGAG ACACTGCTCC       240

CAGCTAGGTG CTCATCTACT GAAGATAGAC AACTCAAAAG AATTTGAGTT CATTGAAAGC       300

CAAACATCGT CTCACCGTAT TAATGCATTT TGGATAGGCC TTTCCCGCAA TCAGAGTGAA       360

GGGCCATGGT TCTGGGAGGA TGGATCAGCA TTCTTCCCCA ACTCGTTTCA AGTCAGAAAT       420

ACAGTTCCCC AGGAAAGCTT ACTGCACAAT TGTGTATGGA TTCATGGATC AGAGGTCTAC       480

AACCAAATCT GCAATACTTC TTCATACAGT ATCTGTGAGA AGGAACTG                    528

(2) INFORMATION FOR SEQ ID NO: 8:

(i) SEQUENCE CHARACTERISTICS:
        (A) LENGTH: 176 amino acids
        (B) TYPE: amino acid
        (C) STRANDEDNESS: <Unknown>
        (D) TOPOLOGY: linear (xi) SEQUENCE DESCRIPTION: SEQ ID NO: 8:

Phe Trp Arg His Asn Ser Gly Arg Asn Pro Glu Glu Lys Asp Asn Phe
1               5                   10                  15

Leu Ser Arg Asn Lys Glu Asn His Lys Pro Thr Glu Ser Ser Leu Asp
            20                  25                  30

Glu Lys Val Ala Pro Ser Lys Ala Ser Gln Thr Thr Gly Gly Phe Ser
        35                  40                  45

```
Gln Ser Cys Leu Pro Asn Trp Ile Met His Gly Lys Ser Cys Tyr Leu
 50                  55                  60
Phe Ser Phe Ser Gly Asn Ser Trp Tyr Gly Ser Lys Arg His Cys Ser
 65                  70                  75                  80
Gln Leu Gly Ala His Leu Leu Lys Ile Asp Asn Ser Lys Glu Phe Glu
                 85                  90                  95
Phe Ile Glu Ser Gln Thr Ser Ser His Arg Ile Asn Ala Phe Trp Ile
                100                 105                 110
Gly Leu Ser Arg Asn Gln Ser Glu Gly Pro Trp Phe Trp Glu Asp Gly
                115                 120                 125
Ser Ala Phe Phe Pro Asn Ser Phe Gln Val Arg Asn Thr Val Pro Gln
130                 135                 140
Glu Ser Leu Leu His Asn Cys Val Trp Ile His Gly Ser Glu Val Tyr
145                 150                 155                 160
Asn Gln Ile Cys Asn Thr Ser Ser Tyr Ser Ile Cys Glu Lys Glu Leu
                165                 170                 175
```

(2) INFORMATION FOR SEQ ID NO: 9:

(i) SEQUENCE CHARACTERISTICS:
        (A) LENGTH: 378 base pairs
        (B) TYPE: nucleic acid
        (C) STRANDEDNESS: single
        (D) TOPOLOGY: linear (xi) SEQUENCE DESCRIPTION: SEQ ID NO: 9:

```
TGCCTTCCTA ATTGGATCAT GCATGGGAAG AGCTGTTACC TATTTAGCTT CTCAGGAAAT    60
TCCTGGTATG GAAGTAAGAG ACACTGCTCC CAGCTAGGTG CTCATCTACT GAAGATAGAC   120
AACTCAAAAG AATTTGAGTT CATTGAAAGC CAAACATCGT CTCACCGTAT TAATGCATTT   180
TGGATAGGCC TTTCCCGCAA TCAGAGTGAA GGGCCATGGT TCTGGGAGGA TGGATCAGCA   240
TTCTTCCCCA ACTCGTTTCA AGTCAGAAAT ACAGTTCCCC AGGAAAGCTT ACTGCACAAT   300
TGTGTATGGA TTCATGGATC AGAGGTCTAC AACCAAATCT GCAATACTTC TTCATACAGT   360
ATCTGTGAGA AGGAACTG                                                 378
```

(2) INFORMATION FOR SEQ ID NO: 10:

(i) SEQUENCE CHARACTERISTICS:
        (A) LENGTH: 126 amino acids
        (B) TYPE: amino acid
        (C) STRANDEDNESS: <Unknown>
        (D) TOPOLOGY: linear (xi) SEQUENCE DESCRIPTION: SEQ ID NO: 10:

```
Cys Leu Pro Asn Trp Ile Met His Gly Lys Ser Cys Tyr Leu Phe Ser
  1               5                  10                  15
Phe Ser Gly Asn Ser Trp Tyr Gly Ser Lys Arg His Cys Ser Gln Leu
                 20                  25                  30
Gly Ala His Leu Leu Lys Ile Asp Asn Ser Lys Glu Phe Glu Phe Ile
                 35                  40                  45
Glu Ser Gln Thr Ser Ser His Arg Ile Asn Ala Phe Trp Ile Gly Leu
 50                  55                  60
Ser Arg Asn Gln Ser Glu Gly Pro Trp Phe Trp Glu Asp Gly Ser Ala
 65                  70                  75                  80
Phe Phe Pro Asn Ser Phe Gln Val Arg Asn Thr Val Pro Gln Glu Ser
                 85                  90                  95
Leu Leu His Asn Cys Val Trp Ile His Gly Ser Glu Val Tyr Asn Gln
```

```
                    100                 105                 110
Ile Cys Asn Thr Ser Ser Tyr Ser Ile Cys Glu Lys Glu Leu
            115                 120                 125
```

(2) INFORMATION FOR SEQ ID NO: 11:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (xi) SEQUENCE DESCRIPTION: SEQ ID NO: 11:

```
Gly Arg Asn Pro Glu Glu Lys Asp Asn Phe Leu Ser Arg Asn Lys Glu
1               5                   10                  15

Asn His Lys Pro
            20
```

(2) INFORMATION FOR SEQ ID NO: 12:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: linear (xi) SEQUENCE DESCRIPTION: SEQ ID NO: 12:

```
Met Lys Tyr His Ser His Ile Glu Asn Leu Asp Glu Asp Gly Tyr Thr
1               5                   10                  15

Gln Leu Asp Phe Ser Thr Gln Asp Ile His Lys Arg Pro Arg Gly Ser
            20                  25                  30

Glu Lys Gly Ser Arg Ala Pro Ser Ser Pro Trp
            35                  40
```

(2) INFORMATION FOR SEQ ID NO: 13:

(i) SEQUENCE CHARACTERISTICS:
        (A) LENGTH: 199 amino acids
        (B) TYPE: amino acid
        (C) STRANDEDNESS: <Unknown>
        (D) TOPOLOGY: linear (xi) SEQUENCE DESCRIPTION: SEQ ID NO: 13:

```
Met Lys Tyr His Ser His Ile Glu Asn Leu Asp Glu Asp Gly Tyr Thr
1               5                   10                  15

Gln Leu Asp Phe Ser Thr Gln Asp Ile His Lys Arg Pro Arg Gly Ser
            20                  25                  30

Glu Lys Gly Ser Arg Ala Pro Ser Ser Pro Trp Arg Pro Ile Ala Val
            35                  40                  45

Gly Leu Gly Ile Leu Cys Phe Val Val Val Val Ala Ala Val Leu
    50                  55                  60

Gly Ala Leu Gly Gly Phe Ser Gln Ser Cys Leu Pro Asn Trp Ile Met
65                  70                  75                  80

His Gly Lys Ser Cys Tyr Leu Phe Ser Phe Ser Gly Asn Ser Trp Tyr
            85                  90                  95

Gly Ser Lys Arg His Cys Ser Gln Leu Gly Ala His Leu Leu Lys Ile
            100                 105                 110

Asp Asn Ser Lys Glu Phe Glu Phe Ile Glu Ser Gln Thr Ser Ser His
            115                 120                 125

Arg Ile Asn Ala Phe Trp Ile Gly Leu Ser Arg Asn Gln Ser Glu Gly
            130                 135                 140
```

-continued

```
Pro Trp Phe Trp Glu Asp Gly Ser Ala Phe Phe Pro Asn Ser Phe Gln
145                 150                 155                 160

Val Arg Asn Thr Val Pro Gln Glu Ser Leu Leu His Asn Cys Val Trp
                165                 170                 175

Ile His Gly Ser Glu Val Tyr Asn Gln Ile Cys Asn Thr Ser Ser Tyr
            180                 185                 190

Ser Ile Cys Glu Lys Glu Leu
        195
```

(2) INFORMATION FOR SEQ ID NO: 14:

(i) SEQUENCE CHARACTERISTICS:
        (A) LENGTH: 145 amino acids
        (B) TYPE: amino acid
        (C) STRANDEDNESS: <Unknown>
        (D) TOPOLOGY: linear (xi) SEQUENCE DESCRIPTION: SEQ ID NO: 14:

```
Met Val Gln Glu Arg Gln Ser Gln Glu Lys Met Trp Gly Cys Cys Pro
1               5                   10                  15

Asn His Trp Lys Ser Phe Gly Ser Ser Cys Tyr Leu Ile Ser Thr Lys
                20                  25                  30

Glu Asn Phe Trp Ser Thr Ser Glu Gln Asn Cys Val Gln Met Gly Ala
            35                  40                  45

His Leu Val Val Ile Asn Thr Glu Ala Glu Gln Asn Phe Ile Thr Gln
        50                  55                  60

Gln Leu Asn Glu Ser Leu Ser Tyr Phe Leu Gly Leu Ser Asp Pro Gln
65                  70                  75                  80

Gly Asn Gly Lys Trp Gln Trp Ile Asp Asp Thr Pro Phe Ser Gln Asn
                85                  90                  95

Val Arg Phe Trp His Pro His Glu Pro Asn Leu Pro Glu Glu Arg Cys
            100                 105                 110

Val Ser Ile Val Tyr Trp Asn Pro Ser Lys Trp Gly Trp Asn Asp Val
        115                 120                 125

Phe Cys Asp Ser Lys His Asn Ser Ile Cys Glu Met Lys Lys Ile Tyr
130                 135                 140

Leu
145
```

(2) INFORMATION FOR SEQ ID NO: 15:

(i) SEQUENCE CHARACTERISTICS:
        (A) LENGTH: 175 amino acids
        (B) TYPE: amino acid
        (C) STRANDEDNESS: <Unknown>
        (D) TOPOLOGY: linear (xi) SEQUENCE DESCRIPTION: SEQ ID NO: 15:

```
Met Val Gln Glu Arg Gln Ser Gln Gly Lys Gly Val Cys Trp Thr Leu
1               5                   10                  15

Arg Leu Trp Ser Ala Ala Val Ile Ser Met Leu Leu Leu Ser Thr Cys
                20                  25                  30

Phe Ile Ala Ser Cys Val Glu Lys Met Trp Gly Cys Cys Pro Asn His
            35                  40                  45

Trp Lys Ser Phe Gly Ser Ser Cys Tyr Leu Ile Ser Thr Lys Glu Asn
        50                  55                  60

Phe Trp Ser Thr Ser Glu Gln Asn Cys Val Gln Met Gly Ala His Leu
65                  70                  75                  80
```

```
Val Val Ile Asn Thr Glu Ala Glu Gln Asn Phe Ile Thr Gln Gln Leu
                85                  90                  95

Asn Glu Ser Leu Ser Tyr Phe Leu Gly Leu Ser Asp Pro Gln Gly Asn
            100                 105                 110

Gly Lys Trp Gln Trp Ile Asp Asp Thr Pro Phe Ser Gln Asn Val Arg
            115                 120                 125

Phe Trp His Pro His Glu Pro Asn Leu Pro Glu Arg Cys Val Ser
130                 135                 140

Ile Val Tyr Trp Asn Pro Ser Lys Trp Gly Trp Asn Asp Val Phe Cys
145                 150                 155                 160

Asp Ser Lys His Asn Ser Ile Cys Glu Met Lys Lys Ile Tyr Leu
                165                 170                 175

(2) INFORMATION FOR SEQ ID NO: 16:

(i) SEQUENCE CHARACTERISTICS:
        (A) LENGTH: 134 amino acids
        (B) TYPE: amino acid
        (C) STRANDEDNESS: <Unknown>
        (D) TOPOLOGY: linear (xi) SEQUENCE DESCRIPTION: SEQ ID NO: 16:

Met Val Gln Glu Arg Gln Ser Gln Gly Lys Gly Val Cys Trp Thr Leu
1               5                   10                  15

Arg Leu Trp Ser Ala Ala Val Ile Ser Met Leu Leu Leu Ser Thr Cys
            20                  25                  30

Phe Ile Ala Ser Cys Val Glu Lys Met Trp Gly Cys Cys Pro Asn His
            35                  40                  45

Trp Lys Ser Phe Gly Ser Ser Cys Tyr Leu Ile Ser Thr Lys Glu Asn
50                  55                  60

Phe Trp Ser Thr Ser Glu Gln Asn Cys Val Gln Met Gly Ala His Leu
65                  70                  75                  80

Val Val Ile Asn Thr Glu Ala Glu Gln Asn Phe Ile Thr Gln Gln Leu
                85                  90                  95

Asn Glu Ser Leu Ser Tyr Phe Leu Gly Leu Ser Asp Pro Gln Gly Asn
            100                 105                 110

Gly Lys Trp Gln Trp Ile Asp Asp Thr Pro Phe Ser Gln Asn Val Arg
            115                 120                 125

Phe Trp His Phe Leu Asp
130

(2) INFORMATION FOR SEQ ID NO: 17:

(i) SEQUENCE CHARACTERISTICS:
        (A) LENGTH: 168 amino acids
        (B) TYPE: amino acid
        (C) STRANDEDNESS: <Unknown>
        (D) TOPOLOGY: linear (xi) SEQUENCE DESCRIPTION: SEQ ID NO: 17:

Met Val Gln Glu Arg Gln Ser Gln Gly Lys Gly Val Cys Trp Thr Leu
1               5                   10                  15

Arg Leu Trp Ser Ala Ala Val Ile Ser Met Leu Leu Leu Ser Thr Cys
            20                  25                  30

Phe Ile Ala Ser Cys Val Val Thr Tyr Gln Phe Ile Met Asp Gln Pro
            35                  40                  45

Ser Arg Arg Leu Tyr Glu Leu His Thr Tyr His Ser Ser Leu Thr Cys
50                  55                  60
```

```
Phe Ser Glu Gly Thr Met Val Ser Glu Lys Met Trp Gly Cys Cys Pro
 65                  70                  75                  80

Asn His Trp Lys Ser Phe Gly Ser Ser Cys Tyr Leu Ile Ser Thr Lys
                 85                  90                  95

Glu Asn Phe Trp Ser Thr Ser Glu Gln Asn Cys Val Gln Met Gly Ala
            100                 105                 110

His Leu Val Val Ile Asn Thr Glu Ala Glu Gln Asn Phe Ile Thr Gln
        115                 120                 125

Gln Leu Asn Glu Ser Leu Ser Tyr Phe Leu Gly Leu Ser Asn Pro Ser
    130                 135                 140

Lys Trp Gly Trp Asn Asp Val Phe Cys Asp Ser Lys His Asn Ser Ile
145                 150                 155                 160

Cys Glu Met Lys Lys Ile Tyr Leu
                165

(2) INFORMATION FOR SEQ ID NO: 18:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO: 18:

ACCCTGAGAC TCTGGTCAGC TGCTGTGATT TCCATGTTAC TCTTGAGTAC CTGTTTCATT    60

GCGAGCTGTG TGGTGACTTA CCAA                                          84

(2) INFORMATION FOR SEQ ID NO: 19:

(i) SEQUENCE CHARACTERISTICS:
        (A) LENGTH: 28 amino acids
        (B) TYPE: amino acid
        (C) STRANDEDNESS: <Unknown>
        (D) TOPOLOGY: linear (xi) SEQUENCE DESCRIPTION: SEQ ID NO: 19:

Thr Leu Arg Leu Trp Ser Ala Ala Val Ile Ser Met Leu Leu Leu Ser
 1               5                  10                  15

Thr Cys Phe Ile Ala Ser Cys Val Val Thr Tyr Gln
            20                  25

(2) INFORMATION FOR SEQ ID NO: 20:

(i) SEQUENCE CHARACTERISTICS:
        (A) LENGTH: 501 base pairs
        (B) TYPE: nucleic acid
        (C) STRANDEDNESS: single
        (D) TOPOLOGY: linear (xi) SEQUENCE DESCRIPTION: SEQ ID NO: 20:

TTTATTATGG ACCAGCCCAG TAGAAGACTA TATGAACTTC ACACATACCA TTCCAGTCTC    60

ACCTGCTTCA GTGAAGGGAC TATGGTGTCA GAAAAAATGT GGGGATGCTG CCCAAATCAC   120

TGGAAGTCAT TTGGCTCCAG CTGCTACCTC ATTTCTACCA AGGAGAACTT CTGGAGCACC   180

AGTGAGCAGA ACTGTGTTCA GATGGGGGCT CATCTGGTGG TGATCAATAC TGAAGCGGAG   240

CAGAATTTCA TCACCCAGCA GCTGAATGAG TCACTTTCTT ACTTCCTGGG TCTTTCGGAT   300

CCACAAGGTA ATGGCAAATG GCAATGGATC GATGATACTC CTTTCAGTCA AAATGTCAGG   360

TTCTGGCACC CCCATGAACC CAATCTTCCA GAAGAGCGGT GTGTTTCAAT AGTTTACTGG   420
```

```
AATCCTTCGA AATGGGGCTG GAATGATGTT TTCTGTGATA GTAAACACAA TTCAATATGT      480

GAAATGAAGA AGATTTACCT A                                                501
```

(2) INFORMATION FOR SEQ ID NO: 21:

(i) SEQUENCE CHARACTERISTICS:
        (A) LENGTH: 167 amino acids
        (B) TYPE: amino acid
        (C) STRANDEDNESS: <Unknown>
        (D) TOPOLOGY: linear (xi) SEQUENCE DESCRIPTION: SEQ ID NO: 21:

```
Phe Ile Met Asp Gln Pro Ser Arg Arg Leu Tyr Glu Leu His Thr Tyr
 1               5                  10                  15

His Ser Ser Leu Thr Cys Phe Ser Glu Gly Thr Met Val Ser Glu Lys
            20                  25                  30

Met Trp Gly Cys Cys Pro Asn His Trp Lys Ser Phe Gly Ser Ser Cys
        35                  40                  45

Tyr Leu Ile Ser Thr Lys Glu Asn Phe Trp Ser Thr Ser Glu Gln Asn
50                  55                  60

Cys Val Gln Met Gly Ala His Leu Val Val Ile Asn Thr Glu Ala Glu
65                  70                  75                  80

Gln Asn Phe Ile Thr Gln Gln Leu Asn Glu Ser Leu Ser Tyr Phe Leu
                85                  90                  95

Gly Leu Ser Asp Pro Gln Gly Asn Gly Lys Trp Gln Trp Ile Asp Asp
            100                 105                 110

Thr Pro Phe Ser Gln Asn Val Arg Phe Trp His Pro His Glu Pro Asn
        115                 120                 125

Leu Pro Glu Glu Arg Cys Val Ser Ile Val Tyr Trp Asn Pro Ser Lys
130                 135                 140

Trp Gly Trp Asn Asp Val Phe Cys Asp Ser Lys His Asn Ser Ile Cys
145                 150                 155                 160

Glu Met Lys Lys Ile Tyr Leu
                165
```

(2) INFORMATION FOR SEQ ID NO: 22:

(i) SEQUENCE CHARACTERISTICS:
        (A) LENGTH: 393 base pairs
        (B) TYPE: nucleic acid
        (C) STRANDEDNESS: single
        (D) TOPOLOGY: linear (xi) SEQUENCE DESCRIPTION: SEQ ID NO: 22:

```
TGCCCAAATC ACTGGAAGTC ATTTGGCTCC AGCTGCTACC TCATTTCTAC CAAGGAGAAC       60

TTCTGGAGCA CCAGTGAGCA GAACTGTGTT CAGATGGGGG CTCATCTGGT GGTGATCAAT      120

ACTGAAGCGG AGCAGAATTT CATCACCCAG CAGCTGAATG AGTCACTTTC TTACTTCCTG      180

GGTCTTTCGG ATCCACAAGG TAATGGCAAA TGGCAATGGA TCGATGATAC TCCTTTCAGT      240

CAAAATGTCA GGTTCTGGCA CCCCCATGAA CCCAATCTTC CAGAAGAGCG GTGTGTTTCA      300

ATAGTTTACT GGAATCCTTC GAAATGGGGC TGGAATGATG TTTTCTGTGA TAGTAAACAC      360

AATTCAATAT GTGAAATGAA GAAGATTTAC CTA                                  393
```

(2) INFORMATION FOR SEQ ID NO: 23:

(i) SEQUENCE CHARACTERISTICS:
        (A) LENGTH: 131 amino acids
        (B) TYPE: amino acid (C) STRANDEDNESS: <Unknown>
(D) TOPOLOGY: linear (xi) SEQUENCE DESCRIPTION: SEQ ID NO: 23:

Cys Pro Asn His Trp Lys Ser Phe Gly Ser Ser Cys Tyr Leu Ile Ser
1               5                   10                  15

Thr Lys Glu Asn Phe Trp Ser Thr Ser Glu Gln Asn Cys Val Gln Met
            20                  25                  30

Gly Ala His Leu Val Val Ile Asn Thr Glu Ala Glu Gln Asn Phe Ile
            35                  40                  45

Thr Gln Gln Leu Asn Glu Ser Leu Ser Tyr Phe Leu Gly Leu Ser Asp
50                      55                  60

Pro Gln Gly Asn Gly Lys Trp Gln Trp Ile Asp Asp Thr Pro Phe Ser
65                  70                  75                  80

Gln Asn Val Arg Phe Trp His Pro His Glu Pro Asn Leu Pro Glu Glu
                85                  90                  95

Arg Cys Val Ser Ile Val Tyr Trp Asn Pro Ser Lys Trp Gly Trp Asn
            100                 105                 110

Asp Val Phe Cys Asp Ser Lys His Asn Ser Ile Cys Glu Met Lys Lys
            115                 120                 125

Ile Tyr Leu
130

(2) INFORMATION FOR SEQ ID NO: 24:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (xi) SEQUENCE DESCRIPTION: SEQ ID NO: 24:

Met Val Gln Glu Arg Gln Ser Gln Gly Lys Gly Val Cys Trp
1               5                   10

(2) INFORMATION FOR SEQ ID NO: 25:

(i) SEQUENCE CHARACTERISTICS:
        (A) LENGTH: 50 amino acids
        (B) TYPE: amino acid
        (C) STRANDEDNESS: <Unknown>
        (D) TOPOLOGY: linear (xi) SEQUENCE DESCRIPTION: SEQ ID NO: 25:

Phe Trp Arg His Asn Ser Gly Arg Asn Pro Glu Glu Lys Asp Asn Phe
1               5                   10                  15

Leu Ser Arg Asn Lys Glu Asn His Lys Pro Thr Glu Ser Ser Leu Asp
            20                  25                  30

Glu Lys Val Ala Pro Ser Lys Ala Ser Gln Thr Thr Gly Gly Phe Ser
            35                  40                  45

Gln Ser
50

(2) INFORMATION FOR SEQ ID NO: 26:

(i) SEQUENCE CHARACTERISTICS:
        (A) LENGTH: 36 amino acids
        (B) TYPE: amino acid
        (C) STRANDEDNESS: <Unknown>
        (D) TOPOLOGY: linear (xi) SEQUENCE DESCRIPTION: SEQ ID NO: 26:

```
Phe Ile Met Asp Gln Pro Ser Arg Arg Leu Tyr Glu Leu His Thr Tyr
1               5                   10                  15

His Ser Ser Leu Thr Cys Phe Ser Glu Gly Thr Met Val Ser Glu Lys
                20                  25                  30

Met Trp Gly Cys
            35
```

(2) INFORMATION FOR SEQ ID NO: 27:

(i) SEQUENCE CHARACTERISTICS:
        (A) LENGTH: 131 amino acids
        (B) TYPE: amino acid
        (C) STRANDEDNESS: <Unknown>
        (D) TOPOLOGY: linear (xi) SEQUENCE DESCRIPTION: SEQ ID NO: 27:

```
Cys Pro Asn His Trp Lys Ser Phe Gly Ser Ser Cys Tyr Leu Ile Ser
1               5                   10                  15

Thr Lys Glu Asn Phe Trp Ser Thr Ser Glu Gln Asn Cys Val Gln Met
                20                  25                  30

Gly Ala His Leu Val Val Ile Asn Thr Glu Ala Glu Gln Asn Phe Ile
            35                  40                  45

Thr Gln Gln Leu Asn Glu Ser Leu Ser Tyr Phe Leu Gly Leu Ser Asp
        50                  55                  60

Pro Gln Gly Asn Gly Lys Trp Gln Trp Ile Asp Asp Thr Pro Phe Ser
65                  70                  75                  80

Gln Asn Val Arg Phe Trp His Pro His Glu Pro Asn Leu Pro Glu Glu
                85                  90                  95

Arg Cys Val Ser Ile Val Tyr Trp Asn Pro Ser Lys Trp Gly Trp Asn
                100                 105                 110

Asp Val Phe Cys Asp Ser Lys His Asn Ser Ile Cys Glu Met Lys Lys
                115                 120                 125

Ile Tyr Leu
130
```

(2) INFORMATION FOR SEQ ID NO: 28:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (xi) SEQUENCE DESCRIPTION: SEQ ID NO: 28:

```
His His His His His His
1               5
```

(2) INFORMATION FOR SEQ ID NO: 29:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 29:

AGGCCCTATG AAGAACTACA GACA                                     24

(2) INFORMATION FOR SEQ ID NO: 30:

(i) SEQUENCE CHARACTERISTICS:

```
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 30:

AACCATGGCC CTTCACTCTG                                                     20

(2) INFORMATION FOR SEQ ID NO: 31:

(i) SEQUENCE CHARACTERISTICS:
        (A) LENGTH: 180 amino acids
        (B) TYPE: amino acid
        (C) STRANDEDNESS: <Unknown>
        (D) TOPOLOGY: linear (xi) SEQUENCE DESCRIPTION: SEQ ID NO: 31:

His His His His His His Gly Ser Asn Ser Gly Arg Asn Pro Glu Glu
1               5                   10                  15

Lys Asp Asn Phe Leu Ser Arg Asn Lys Glu Asn His Lys Pro Thr Glu
            20                  25                  30

Ser Ser Leu Asp Glu Lys Val Ala Pro Ser Lys Ala Ser Gln Thr Thr
        35                  40                  45

Gly Gly Phe Ser Gln Ser Cys Leu Pro Asn Trp Ile Met His Gly Lys
    50                  55                  60

Ser Cys Tyr Leu Phe Ser Phe Ser Gly Asn Ser Trp Tyr Gly Ser Lys
65                  70                  75                  80

Arg His Cys Ser Gln Leu Gly Ala His Leu Leu Lys Ile Asp Asn Ser
                85                  90                  95

Lys Glu Phe Glu Phe Ile Glu Ser Gln Thr Ser Ser His Arg Ile Asn
            100                 105                 110

Ala Phe Trp Ile Gly Leu Ser Arg Asn Gln Ser Glu Gly Pro Trp Phe
        115                 120                 125

Trp Glu Asp Gly Ser Ala Phe Phe Pro Asn Ser Phe Gln Val Arg Asn
    130                 135                 140

Thr Val Pro Gln Glu Ser Leu Leu His Asn Cys Val Trp Ile His Gly
145                 150                 155                 160

Ser Glu Val Tyr Asn Gln Ile Cys Asn Thr Ser Ser Tyr Ser Ile Cys
                165                 170                 175

Glu Lys Glu Leu
            180

(2) INFORMATION FOR SEQ ID NO: 32:

(i) SEQUENCE CHARACTERISTICS:
        (A) LENGTH: 85 amino acids
        (B) TYPE: amino acid
        (C) STRANDEDNESS: <Unknown>
        (D) TOPOLOGY: linear (xi) SEQUENCE DESCRIPTION: SEQ ID NO: 32:

His His His His His His Gly Ser Ala Cys Glu Leu Trp Gly Cys Cys
1               5                   10                  15

Pro Asn His Trp Lys Ser Phe Gly Ser Ser Cys Tyr Leu Ile Ser Thr
            20                  25                  30

Lys Glu Asn Phe Trp Ser Thr Ser Glu Gln Asn Cys Val Gln Met Gly
        35                  40                  45

Ala His Leu Val Val Ile Asn Thr Glu Ala Asp Glu Asn Phe Ile Thr
    50                  55                  60
```

```
Gln Gln Leu Asn Glu Ser Leu Ser Tyr Phe Leu Gly Leu Ser Asp Pro
 65                  70                  75                  80

Gln Gly Asn Gly Lys
                85

(2) INFORMATION FOR SEQ ID NO: 33:

(i) SEQUENCE CHARACTERISTICS:
        (A) LENGTH: 10409 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 6510
        (D) OTHER INFORMATION: /mod_base= OTHER
            /note= "D = A or G or T"

(ix) FEATURE:
        (A) NAME/KEY: modified_base
        (B) LOCATION: 3406..6470
        (D) OTHER INFORMATION: /mod_base= OTHER
            /note= "K = G or T"

(ix) FEATURE:
        (A) NAME/KEY: modified_base
        (B) LOCATION: 3564..7896
        (D) OTHER INFORMATION: /mod_base= OTHER
            /note= "M = A or C"

(ix) FEATURE:
        (A) NAME/KEY: modified_base
        (B) LOCATION: 3497..3607
        (D) OTHER INFORMATION: /mod_base= OTHER
            /note= "N = A or C or G or T"

(ix) FEATURE:
        (A) NAME/KEY: modified_base
        (B) LOCATION: 3479..6422
        (D) OTHER INFORMATION: /mod_base= OTHER
            /note= "R = A or G"

(ix) FEATURE:
        (A) NAME/KEY: modified_base
        (B) LOCATION: 3405..6871
        (D) OTHER INFORMATION: /mod_base= OTHER
            /note= "S = C or G"

(ix) FEATURE:
        (A) NAME/KEY: modified_base
        (B) LOCATION: 3457..9998
        (D) OTHER INFORMATION: /mod_base= OTHER
            /note= "W = A or T"

(ix) FEATURE:
        (A) NAME/KEY: modified_base
        (B) LOCATION: 3595..9999
        (D) OTHER INFORMATION: /mod_base= OTHER
            /note= "Y = C or T"

(xi) SEQUENCE DESCRIPTION: SEQ ID NO: 33:

CATTGGCCCG CTCTGTGGCA TTTAACTCAA GTGTGTGTGG AAGTTGATTC TGAACTCTGG      60

CCTCTTTGAC AGAAGCCAGG TCCCTGAGTC GTATTTTGGA GACAGATGCA AGGAAACCCC     120

TGACCTTCTG AACATACACC TCAACAATGG TGCAGGAAAG ACAATCCCAA GGTGAGGTGA     180

GAATTCCTGT CTCAGTCAAA GGAGACAATA GGAATACGTA CTGTGATGAG GATCTACCTG     240

GGACAAGTGG CAGGCTGAAG TGGTGAAGTA GATCAAGACA GCAGAGTCCC AGGGATGTGT     300

CAGAAGTATA ATATCTCAGA GCCAGAAGCC CTCAAAACAA CAAGAAACCA AATTATTGAA     360

GGGGGTGTGA AATGTGACAA CAAGAAGAAA GTATAAGGTC ATGGAAATTG CAGGTGCCTG     420
```

-continued

| | | | | | |
|---|---|---|---|---|---|
| AGGGTGAAAT | ATTTCTAGAT | TGTGAGTGTG | TGTGTGTGTG | TGTGTGTGTG | 480 |
| TGTGTGTGCT | TAAGAGCTGA | CTTGGTCATA | TTATAGGGCT | GTGACAGCTT | TTTCCTACTT | 540 |
| TAAGTTCATA | ATTATTCTGA | GCATTTTGTC | TGGTTATTAA | CTGATCTAAG | GTTTTTGGTC | 600 |
| CTGTGGTGAG | TACATCTGAT | TGCTATCTGA | CAGGGAAGGG | AGTCTGCTGG | ACCCTGAGAC | 660 |
| TCTGGTCAGC | TGCTGTGATT | CCATGTTAC | TCTTGAGTAC | CTGTTTCATT | GCGAGCTGTG | 720 |
| TGGGTAAGTT | CTTCATTGAC | TGGTGTCTCT | TTTGGGGCAC | TGTCTAGTCT | CTGTTCCACA | 780 |
| GAGACTCCAA | GGGACACTTT | TGTTTTGTTT | TGGCTTTTCA | AGACAGAGTT | TTTCTGTGTA | 840 |
| ACAAGCCTTG | GCTGTCCTGG | AATTCTCTCC | ATAGATCAGG | ATGGCCCTGA | ACTCAAAGAG | 900 |
| ATCCTCCTAC | CTCTGCCTCT | TAAGTGCTGG | GATTGAAGGC | ATATGCTACC | ACCAGCCTGG | 960 |
| AGTTGTTATT | TTAATCCCAT | TATCCGGTCT | GACTTCACAG | GTAATGCCAT | GTTTTCTTG | 1020 |
| ACTTCTCTTC | TTTGTTCCTT | TTCTTTTTTT | TCCCCCATCT | TTTGACTAAT | GAGATATGTA | 1080 |
| AGGTTTCTTC | ACCAGCTTTG | TTAGCTCATA | CTATTTACAA | CCATTGTCTG | TGACAGTGCC | 1140 |
| TTCCAGCACT | GGGTTCACCA | GTAATCACAG | TCTCTTCTCA | CATCTCTATA | TTGGGAGTGC | 1200 |
| AAGTCCAGTT | GATTTCATAA | TGTCGACAGC | TTAGAGTCTG | ATTTATATGG | GATTTTCCTT | 1260 |
| TCTCAATAGA | AGAGTAAAAA | GTCACCAAAT | GAGATAGTGA | TGATTGAGGA | AATAAAATAT | 1320 |
| CTCTGTCCTG | TTTCATCTGC | TCAGAATCCG | TGTGTGAAGT | CTATTATGTG | AGAAGTTTTG | 1380 |
| ATGATATTCT | TTGCAGTCAA | CAGTCTGCTT | CTCCATTTGC | TATCAGGTTG | ATCACAATAA | 1440 |
| TTGCTGTACA | GTCCAGGAAA | TAGTGAGAGT | GACTTGATGT | TGGCAGTATG | CTCTGTGATA | 1500 |
| AGACAAACTC | ATCTTCTCCT | TGAAGCAACA | TCTGCTCTAA | TTGGCAGAGT | CAAACTTAAG | 1560 |
| AGAACAGATT | GTGGCCATTA | AGAATAGTTA | TTTCACGGAC | CAAGAAGAAA | CAGATGGTCA | 1620 |
| GAACCCAAAA | CATGGAGTAG | AAACATTTGC | TTAGAATAGT | AAAGAAGATC | TGTTTTTGTT | 1680 |
| AACATTGTTT | AATGTGCACA | CTCATGAAAA | CTGCTAATTA | AAAATAATTT | TTATTTATTT | 1740 |
| TTTGAAACTT | TCCTACTCAT | ATACAACATA | CCTTGACCAT | ACATTCCCCA | CTTAAAAGTC | 1800 |
| TCTAGATGTT | TAAAGTCCTC | CTACCTACAA | TCAGGAATGG | TAAGGATATG | TAAACATACC | 1860 |
| CATTATTCTT | GCCTCAAAGT | TGTTTAAACA | AAGGAGGCTA | GACACTGGTG | AGGCAACAGA | 1920 |
| TTACTATCCA | GGACTTGTGG | CAGTTCCCTG | ATGCAGGGGT | TTGTTATTAA | TTCATGAAGA | 1980 |
| AGATTAGATG | TTTATTCCAG | AAAAATACAG | CTGATATTAT | AGTGGGGAAA | AGAAAAAACA | 2040 |
| AATGAGGAGA | TGTATAAACT | AGTAATTTAA | ATGAATATAG | GAGAGCAATA | ATTTAGTCTT | 2100 |
| GTCGTTAGTG | GGTTTACCTG | GAGATGTAGG | GGAGGTATAG | TGGAGGGAGA | AGCCTGACCC | 2160 |
| AGGTAGAGGA | CATGAGGCTC | CAGGGATAGC | TAGGTCATGC | TCATACCCTT | CTTTCTTCAC | 2220 |
| AGTGACTTAC | CAATTTATTA | TGGACCAGCC | CAGTAGAAGA | CTATATGAAC | TTCACACATA | 2280 |
| CCATTCCAGT | CTCACCTGCT | TCAGTGAAGG | GACTATGGTG | TCAGGTGAAG | ATTTTCAATA | 2340 |
| TTTTGCTAGA | CTTGGGGGT | CATTATTAGG | GTTAAATTTA | ACATATATTT | ATTATACTGT | 2400 |
| AGGTGTGAGA | AAGAGAGAGA | AAAAAATAGA | GGGACACAC | ACACACACAC | ACACACACAC | 2460 |
| ACACAGAGAG | AGTATGTCAG | GTAAACTCTG | GAAGTTTTTA | TTAAAGATTC | TCATGAGTTT | 2520 |
| TAAATTCAAT | ACATAAAATT | CTCTTTGGCA | GTTGANTTCC | CTCCAATTAA | TACTATACAT | 2580 |
| CTCCATTCCC | CAAGTTACCA | GCTTTTATTA | CTGGGGAAAA | CTTGACCCNG | GCTGAACCCC | 2640 |
| GCCCCGTGTT | CATAAATTGC | ATAAAATGGC | AATTTGCTCC | NATTCAATTT | AATTCCTAGG | 2700 |
| NATCTTGATT | TTGAGNAACA | CTGTCAACAC | ACACACACAC | ACACACACAC | ACACACACAC | 2760 |
| ACACACACAC | ACACACACAC | AGTATGTCAN | NNAAACTCTG | NAAGNTNTNA | TTAAAGATTC | 2820 |

```
TCATGAGNNN NAAATTCAAT ANATAAAATT CTCTTTGGCA GNTGAGTTCC TCAATTAATA      2880

CTATACATCT CCGATTCCAA GTACCAGCTT TATTACTGGG AAAACTGACT CAGCTGAGCC      2940

TGCCCGAGTC ATAAGTGCAT AAATGGCAAA TTTGTGTATG GAGAGTCAAN TTNGANCATC      3000

ATATCTGCCT CACCTCTGTG TNATGATAGG CACTTGTCTT TAATTTTCTT TATGGGATTA      3060

TTATTTAACA TATAACAATG GCATCTAAAC ATCGATCAGA GTCCTGATCC AAGGAACTGG      3120

GTTACTCACC ATGCCATATC TATTAATNAC TATTATTATT ATTATTAATT TACATCCTTG      3180

TGGAAAGAGA AGTATATGTG AAGACAGAAC AAAAGCCCCT CATACATCTA NGTGTTGTTG      3240

ANATTTCTG TTTCAGTCAN TGTNTANAAT ACATTGTGCG GCANCNCNAN GGTTGCCCTG       3300

ACCATGCTTA TCTTANCACA TTGAGTTCAT TGTGCCAAAC AACTGTGGGG CTGATTCTTT      3360

CCCGAGGAAA ACATAATTCC AAGAGGATAG TCTTTCTTTA TTTTSKGGAG AACATTTATA      3420

ACCAATAACC TGTTTCCATA TATTCTAATT TTTGGAWGGT AAWCAGTTTC WACCCAGGRA      3480

AGGGTTGGGC TCCTTANRAA AGCCTAAACT ARCTTGTACW TCGCAACCCT CCTGCTTCAG      3540

CCTCCCTGTG TTCTGGGGAT TACMACMGAA TATTAGAAGG ACTTCMACMA NGGGYTRCAG      3600

NYWGYWNKTT WWAAARGRAA AAAATTGGGC AMCTTGGGCC CTTTTAAGGG RRGGCYYCTT      3660

GARAAATKGA GASARGAAGT RRRATTTTAA ATTTAAATTA ATTTTGGTAT TCTATTCTAT      3720

AAAACAACAT TTCCTAAAGT GTATCTGCCT TAAAATTATG GGTCAAGCAG GCTATTTGGC      3780

ATAATTAATT TTGTTTCTTA GGATAAGTTT ATGTGATGAA ATTATTTATC TTATACCATG      3840

TCAWGAAAAA TCAAATAACA GACGTTTAAC AATACTCTTT AGAATTAATA CAATACAAAG      3900

AAGAGGGAAA CTTTCAGCAA AAATATTTAT ATTTTGTTAT TCATGCTGAT TCATTAAATT      3960

CTGTAATCCC AACACTTCGG AGGTAGTGGC AGGAGAATTT GTACAGATAT GAATTTAGTC      4020

TGGTCTACCT AGAGATTTCT AGGGCTAAAT AATGAGATTC TGTATCAAAG GGAAAAATTA      4080

TCTGGGTGTA AAAGGAAAAA TAATTATCTG GCTGTAGCAG TCTGGGCTCA TATCTGTGGT      4140

TTCTTAGAGT TTGTAGAACA TCTGTTCAGG CCCTTCTGGC TTTTACAGTC TTCAATGAGA      4200

GGTCAGGCAT TATTCTAGTA GGTTTATATT TATATGTTAC TCAGTCTTTT CCTCTTGCAG      4260

CTTTTCACAT TCTTTCTTTG TTCTGTATGT TTAGCATTTT GATTATTGTG TGTTGTGGGG      4320

AATATCTTTT CTGATCCAGT CCATTGGTG TTCTGCATGT TTTTTGTACC TTGATAATCA       4380

TCTCCTTAAG GTTGAAGACA TTTTCTTTTA TGATTTTGTT GAAAATATTT CCTGTGCATT      4440

TTAACTTGGC YTTCTTTTTC TTTGTCTATT CCYATAGACT TAGTTTTGTT TGTTTGTTTG      4500

TTTTTAATCT GAGAATTCCT GGATGTTTTG TGCCCTKGAG TTTTTTTTTT WTATTAATAT      4560

TTYCTTKGAC TGGAGATAYW CCTTTCTTCT ATCCTGTCTT CAGTGCCTGA GTTTTTCTCT      4620

TTCATTTCCT ATACTGAGTT GTTGGTGAGG CATACCTCTT AGACCTTGTT TGTCTTCCCA      4680

AATTATACAT TTCCAGTTTC ATGTCTAGTT TTACTTATCG ATTATATTTT TACTTTCATG      4740

ACATAACTTC TTTTCATTAT TTTATTCTAC CATGTGTGTT TTTACAGACT TCTAATTCAA      4800

TGGTATTTTT GCCAATTATT TTGGTCTCAT ATTGCTTTAT TGGGGCATTG AAAAACAATA      4860

CTGGTCTTTG TTTGTAAATT ATGGTTCCTT TTTTTTAAAT GATCTTTGTT TCTCTCTGTG      4920

TCAGTTGAGT CTCTGTGTGT TTCTTGTTCT TTTCTTTAAT TTTAAATTGT GTCCTTTAAA      4980

AAATTTGCCC GTTTATTTTC AAGAGAGAGA GAGAGAGAGA GAGAGAGAGA GAGAGAGAGA      5040

GGGAGAGAGA GAGAGAGAGA GACAGACAGA GACAGACACA GAGAGACAGA GACAGAGAGA      5100

CAGAGACAGA GAGAGAGAGA GAGGAAGAGA GGGAGAGAAG GTATGGAATT GGATGTGAAG      5160
```

-continued

```
AGAGGTGGGA AGGATCATGG AAGAGATGGT GGAGAAGAAG TCATGATCAG GATATATTGT    5220

GTAAAAATGA CTTTCAATTA AAAAAATAAA AGCGAAGAAT AAAATTAGTT CATAAAGGCC    5280

AGAAAGATGT CCATTTTGAA CACAGTTAAA TAATGTTTAG AAAGGACACT TTCCTTTTTA    5340

CAGTACATTC CTACTCAGGG AGAGTGTTAA GAAATTGGGA TACTTGAGTC AAAGCATAAA    5400

CTATATTATT CATTCTTAAT AATCAATAAA TTATGGATAC AATTTTTGAA TGTTTGATAA    5460

TCCATAAAAA TTAGTAAGGA AGTAATATTT ATAGAGCAAT TACTATGAAC TAAGTACTGT    5520

TTCAAATGTT TCAGAGATAT TATGTGATTA AATAACCCAT GAGGCCAGCA CTGCTCTCAA    5580

TATAAGTTCC CTGGCCCCAA ATTATTTATT CTAAAAATGG TAAACGTGTA ATTACATTGA    5640

GAAAGCACCT CTGGCAAGGA GCCTCAGAAC CTTGGAGTTT CCTAGAATAT GTCTCCTTAA    5700

TCTTATTTGT CTCATCTCAT GGTCAAACTT CTTGTTCATG TCACAGAAAA AATGTGGGGA    5760

TGCTGCCCAA ATCACTGGAA GTCATTTGGC TCCAGCTGCT ACCTCATTTC TACCAAGGAG    5820

AACTTCTGGA GCACCAGTGA GCAGAACTGT GTTCAGATGG GGGCTCATCT GGTGGTGATC    5880

AATACTGAAG CGGAGCAGGT AGTGCTTTCT TGTTTTTCAT TAGCCTTTTA ATTGTAGGAA    5940

AATGTAGTTT GAAATGTATG TTCATCCCAT TGTAGAAAAG CCCCTTAGAA TTTTTATACC    6000

TAGGAAGATT GGAGTTCTCT GCTCCAGTGG GTAGTCGAAT AGACTACCCA CTTCCAAATC    6060

CATAAGGTTC TGGCAATTAC TCTTCTAATT TTTTTTAAAT GAGTTTGATT ACTTTAGATT    6120

CTTCATATAA GTGGAATCAT GTATTATTTT GTGTGTATGT GTGTGTGTAT GCTTGTACAT    6180

GTGTGTGTTT GTCTAGATGA TTTTATTCAG CATGATGTCC TCAAGACTCA TTCATGTTGT    6240

ACCATGTGAC TTTTTTTTAA GTCTGAATAT TCCATTATAT ACATATTTCA CATTTTATCT    6300

TTGTTTTATG TGTTTTTTTT AGTTATCTTA AGGTGTGATT GACAGAAAAA GATGTACATA    6360

TTTCCAGTGT TACAATGTTA ATTATTTGCC AATACATTTT TGAAAATGRA KTACMACAGT    6420

GRAATTAATG GYTCAAAAYT CATWACAATG KGGCATGTAT GTGTGTGGAK GAGAAMACYT    6480

AAATTACCAC CATCTCTCCA TTCAGGGGTD GCTTCCATAC AGATTGCTTC CATTCCATGG    6540

CTATTGTGAA TAGTACAGTG AATATGGTTG TGTAAATTTC TTCTTTACGT CTTACTGTTA    6600

ATAAAATTAT TTCACAATTT TATTCATATA TAATGCTCTT TGATCAGTTT CCCTCATCAT    6660

TTTCTCTTAT CCCCTCCCTT TTCTGCTGAA CCTCTATTCT TTCCAAATTT CCCTCTCTAT    6720

CCTTTCTTTT TGTGAATGAG ATTCATATTT CAATAACCCT ATGAGCATAG GTGTGCAGCT    6780

ATTTACTTGA GTGAGGGCAA TGCCCAGTGG CCAAACCTCT GACAAATATA ACTCCTAGCA    6840

GGAAATTGTT AACTGGTCCC ATAGCCCCYC SGAGAGGGAT GGGGTCTTAC TATCCCCTCC    6900

CATATCCATG ATGGGCTGTT GAGGCTCCCA GTCTTGTGCA TGTCTTTTAC AGGTAGCCAT    6960

TGCTGTTGTG AGTTTCAACT CTTGCATTCT TTCTCCTCTG TGATACTCAC TGAGCTTGGA    7020

GTGGAGTGGC ATAGTTGTTT CATTGAAGGA CATTAACCTG TTATGAGTCT CTGCAAAAGC    7080

ATCATCCACT GTAAATAGAA GCTTTTCTGA AGCCTCTGTG GCCTTCCTGA CCAACATCTT    7140

ATAAAGAAGT ATCTCAGAAA AAATACTGGG ATTTTTTTCT AATGATTTAT TTATTTATTT    7200

ATTTATTTAT TTATTTATTT ATTTAACGCA TATTAGTGTT TACCTGTATG TATGTCTGTG    7260

TGAGGTTGTC GGATTCCATG GAACTGGAGT TACAGACAGT TGTGAGTTGC CATGTGGGTG    7320

CTGGGAATTG AAATCTGGTC TTCTGGAAGA GCAGCTAGTA CTCTTAACCA CTGAGCAATT    7380

TCTCTAGCCC TTCTTTTTAT TTAATAACTG CTGGAGCAAC TATATTCATA GAGGTTAACC    7440

CCCTTCAAAC TCTATTTTTA AAATTTTATT TTAAACTGGT GTACAAAGCT GTAGGCTTCA    7500

ATATGACTTT CTCACACATC CTTAGTTTTG GTTCAACCTC CCCCATCCAT TCATCTCCCT    7560
```

-continued

| | |
|---|---|
| CATCACCCAC TACACATTCA CTTAAACATT TACAAATTCA CATTTACGTT CACTCCACCC | 7620 |
| ACTTTTCTAG CACWTTGGGT TCTYCTATCC CTCCTCCTTT AAGGCATTCC CACCCTTCTC | 7680 |
| CATCAATGGC CCCGTTTCTC GGTTTCCTGC GACTCTMACC AGATACTTTA CATTAAACCC | 7740 |
| ATTAATCTAA AAATTCCAAG AGAGGTTTCA CATAGAGWTA GAATATGCTG GCATTTCGCC | 7800 |
| TTCCTGGGGC CTGGCTTAAC TAATAATTTT TCCTCATGYY ATTAATTCAC TTTCACATTT | 7860 |
| CACAATTTCA TTTTCTTTCA CAATTCTATC AGTATMACCA TGGGTCACAT TTACCACTGT | 7920 |
| CCAGTTTTAA TTGGYGGACA TCTAGGGATG ATCCCATTTT CTTCAGCTAC TGTGCATAGG | 7980 |
| AACAAACAAT GAAGGTAGAT GAGTAAATAC CTCTGAAATA GAATGCTTTG GGTATGCCCC | 8040 |
| AGGAATGACA TAGTTGAGTC ATGTGGCATT TCTAGTTTTA GTGATCTCTA CCAAAGGCAG | 8100 |
| GAAGCAAGAT AAGATGAACT GCTCTTTCCT TTGCCTTGTT CTATTTAGGA TCTTAAATGT | 8160 |
| TTAGATAATG TCTACCCACA TTGGTTAGGA CAAGCTGGTT TAATGAGATC ACAGATACTG | 8220 |
| TAGCCAATTA TATCTGGGAA CACATTACAG ATATACTCAG AAATGTTCTT TTAATCTGAG | 8280 |
| CATTTCTTGG CTCTGCCAAG AATAGACATA GAATATAATA TCTTAACATT TAAACAAATC | 8340 |
| ACATTTTTTT CTCTTTCTTT TTTTTCCCCA TTTTTATTAG GTATTTACCT CATTTACATT | 8400 |
| TCCAATGCTA TACCAAAAGT CCCCCATACC CACCCACCCC CACTCCCCTA CCCACCCACT | 8460 |
| CCCCCTTTTT GGCCCTGGCG TTCCCCCGTA CTGGGCATA TAAAGTTTGC GTGTCCAATG | 8520 |
| GGCCTTTCTT TCCAGTGATG TCCGACTAGG CCATCTTTTG ATACATATGC AGCTAGAGTC | 8580 |
| AAGAGCTCCA ATCTTCCTAG GTATAAAAAT TCTAAGGGGC TTTTCTACAA TGGGATGAAC | 8640 |
| ATACATTTCA AACTACATTT TCCTACAATT AAAAGGCTAA TGAAAAACAA GAAAGCACTA | 8700 |
| CCTGCTCCGC TTCAGTATTG ATCACCACCA GATGAGCCCC CATCTGAACA CAGTTCTGCT | 8760 |
| CACTGGTGCT CCAAGCCGAA TTCCAGCACA CTGGCGGCCG TTACTAGTGG ATCCCTGGAT | 8820 |
| ATGGCAGTCT CTACATGGTC CATCCTTTCA TCTCAGCTCC AAACTTTGTC TTTGTAACTC | 8880 |
| CTTCCATGGG TGTTTTGTTC CCAATTCTAA GGAGGGGCAT AGTGTCCACA CTTCAGTCTT | 8940 |
| CATTCTTCTT GAGTTTCATG TGTTTAGCAA ATTGTATCTT ATATCTTGGA TATCCTAGGT | 9000 |
| TTGGGGCTAA TATCCACTTA TCAGTGAGTA CATATTGTGT GAGTTCCTTT GTGAATGTGT | 9060 |
| TACCTCACTC AGGATGATGC CCTCAAGGTC CATCCATTTG CATAGGAATT TCATAAATTC | 9120 |
| ATTCTTTTTA ATAGCTGAGT AGTACTCCAT TGTGTAGATG TACCACATTT TCTGTATCCA | 9180 |
| TTCCTCTGTT GAGGGCATC TGGGTTCTTT CCAGCTTCTG GCTATTATAA ATAAGGCTGC | 9240 |
| TATGAACATA GTGGAGCATG TGTCCTTCTT ACCAGTTGGG GCATCTTCTG GATATATGCC | 9300 |
| CAGGAGAGGT AATGCTGGAT CCTCCGGTAG TACTATGTCC AATTTTCTGA GGAACCGCCA | 9360 |
| GACTGATTTC CAGAGTGGTT GTACAAGCCT GCAATCCCAC CAACAATGGA GGAGTGTTCC | 9420 |
| TCTTTCTCCA CATCCACGCC AGCATCTGCT GTCACCTGAA TTTTTGATCT TAGCCATTCT | 9480 |
| GACTGGTGTG AGGTGGAATC TCAGGGTTAT TTTGATCTGC ATTTCCCTGA TGATTAAAGA | 9540 |
| TGTTGAACAT TTTTTCAGGT GCTTCTCTGC CATTCGGTAT TCCTCAGGTG AGAATTCTTT | 9600 |
| GTTCAGTTCT GAGCCCCATT TTTTAATGGG GTTATTTGAT TTTCTGAAGT CCACCTTCTT | 9660 |
| GAGTTCTTTA TATATGTTGG ATATTAGTCC CCTATCTGAT TTAGGATAGG TAAAGATCCT | 9720 |
| TTCCCAATCT GTTGGTGGTC TTTTTATCTT ATTGACGGTG TCTTTTGCCT TGCAGAAACT | 9780 |
| TTGGAGTTAC ATTAGGTTCC ATTTGTCAAT TCTCGATCTT ACAGCACAAG CCATTGCTGT | 9840 |
| TCTGTTCAGG AATTTTTCCC CTGTGCCCAT ATCTTCAAGG CTTTTCCCCA CTTTCTCCCT | 9900 |

-continued

```
TATAAGTTTC AGTGTCTCTG GTTTTATGTG AAGTTCCTTG WATCCACTTA GATTTGACCT    9960

TAGTACAAGG AGATAAGCAT GGATCAATTC WACATTCWYT TCTCCATGAT AACAACCAGT   10020

TGTGCCAGCA CCAATTGTTG AAAATGCTGT CTTTCTTCCA CTGGATGGTT TTAGCTCCCT   10080

TGTCGAAGAT CAAGTGACCA TAGGTGTGTG GGTTCATTTC TGGGTCTTCA ATTCTATTCC   10140

ATTGGTCTAC TTGTCTGTCT CTACACCAGT ACCATGCTGT TTTTATCACA ATTGCTCTGT   10200

AGTAAAGCTT TAGGTCAGGC ATGGTGATTC CACCAGAAGT TCTTTTATCC TTGAGAAGAC   10260

TTTTTGCTAT CCTAGGTTTT TTGTTATTCC AGACGAATTT GCAAATTGCT CCTTCCAATT   10320

CGTTGAAGAA TTGAGTTGGA ATTTTGATGG GGATTGCATT GAATCTGTAG ATTGCTTTTG   10380

GCAAGATAGC CATTTTTACA ACGTTGATC                                    10409
```

(2) INFORMATION FOR SEQ ID NO: 34:

(i) SEQUENCE CHARACTERISTICS:
        (A) LENGTH: 146 base pairs
        (B) TYPE: nucleic acid
        (C) STRANDEDNESS: single
        (D) TOPOLOGY: linear (xi) SEQUENCE DESCRIPTION: SEQ ID NO: 34:

```
CATTGGCCCG CTCTGTGGCA TTTAACTCAA GTGTGTGTGG AAGTTGATTC TGAACTCTGG     60

CCTCTTTGAC AGAAGCCAGG TCCCTGAGTC GTATTTGGA GACAGATGCA AGGAAACCCC    120

TGACCTTCTG AACATACACC TCAACA                                       146
```

(2) INFORMATION FOR SEQ ID NO: 35:

(i) SEQUENCE CHARACTERISTICS:
        (A) LENGTH: 57 amino acids
        (B) TYPE: amino acid
        (C) STRANDEDNESS: single
        (D) TOPOLOGY: linear (xi) SEQUENCE DESCRIPTION: SEQ ID NO: 35:

```
Asn Trp Ile Ile Tyr Glu Lys Ser Cys Tyr Leu Phe Ser Met Ser Leu
 1               5                  10                  15

Asn Ser Trp Asp Gly Ser Lys Arg Gln Cys Trp Gln Leu Gly Ser Asn
            20                  25                  30

Leu Leu Lys Ile Asp Ser Ser Asn Glu Leu Gly Phe Ile Val Lys Gln
        35                  40                  45

Val Ser Ser Gln Pro Asp Asn Ser Phe
    50                  55
```

(2) INFORMATION FOR SEQ ID NO: 36:

(i) SEQUENCE CHARACTERISTICS:
        (A) LENGTH: 172 base pairs
        (B) TYPE: nucleic acid
        (C) STRANDEDNESS: single
        (D) TOPOLOGY: linear (xi) SEQUENCE DESCRIPTION: SEQ ID NO: 36:

```
TAATTGGATT ATATATGAGA AGAGCTGTTA TCTATTCAGC ATGTCACTAA ATTCCTGGGA     60

CGGAAGTAAA AGACAATGCT GGCAACTGGG CTCTAATCTC CTAAAGATAG ACAGCTCAAa   120

TGAATTGGGA TTTATAGTAA AACAAGTGTC TTCCCAACCT GATAATTCAT TT           172
```

(2) INFORMATION FOR SEQ ID NO: 37:

(i) SEQUENCE CHARACTERISTICS:

(A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 37:

ATGGTGCAGG AAAGACAATC CCAA                                          24

(2) INFORMATION FOR SEQ ID NO: 38:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (xi) SEQUENCE DESCRIPTION: SEQ ID NO: 38:

GGGAAGGGAG TCTGCTGGAC CCTGAGACTC TGGTCAGCTG CTGTGATTTC CATGTTACTC    60

TTGAGTACCT GTTTCATTGC GAGCTGTGTG GT                                 92

(2) INFORMATION FOR SEQ ID NO: 39:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (xi) SEQUENCE DESCRIPTION: SEQ ID NO: 39:

GACTTACCAA TTTATTATGG ACCAGCCCAG TAGAAGACTA TATGAACTTC ACACATACCA    60

TTCCAGTCTC ACCTGCTTCA GTGAAGGGAC TATGGTGTCA G                       101

(2) INFORMATION FOR SEQ ID NO: 40:

(i) SEQUENCE CHARACTERISTICS:
        (A) LENGTH: 152 base pairs
        (B) TYPE: nucleic acid
        (C) STRANDEDNESS: single
        (D) TOPOLOGY: linear (xi) SEQUENCE DESCRIPTION: SEQ ID NO: 40:

AAAAAATGTG GGGATGCTGC CCAAATCACT GGAAGTCATT TGGCTCCAGC TGCTACCTCA    60

TTTCTACCAA GGAGAACTTC TGGAGCACCA GTGAGCAGAA CTGTGTTCAG ATGGGGGCTC   120

ATCTGGTGGT GATCAATACT GAAGCGGAGC AG                                 152

(2) INFORMATION FOR SEQ ID NO: 41:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (xi) SEQUENCE DESCRIPTION: SEQ ID NO: 41:

AATTTCATCA CCCAGCAGCT GAATGAGTCA CTTTCTTACT TCCTGGGTCT TTCGGATCCA    60

CAAGGTAATG GCAAATGGCA ATGGATCGAT GATACTCCTT TCAGTCAAAA TGTCAG       116

(2) INFORMATION FOR SEQ ID NO: 42:

(i) SEQUENCE CHARACTERISTICS:
        (A) LENGTH: 145 base pairs
        (B) TYPE: nucleic acid
        (C) STRANDEDNESS: single
        (D) TOPOLOGY: linear -continued (xi) SEQUENCE DESCRIPTION: SEQ ID NO: 42:

```
GTTCTGGCAC CCCCATGAAC CCAATCTTCC AGAAGAGCGG TGTGTTTCAA TAGTTTACTG        60

GAATCCTTCG AAATGGGGCT GGAATGATGT TTTCTGTGAT AGTAAACACA ATTCAATATG       120

TGAAATGAAG AAGATTTACC TATGA                                             145
```

UNIQUE DENDRITIC CELL-ASSOCIATED C-TYPE LECTINS, DECTIN-1 AND DECTIN-2; COMPOSITIONS AND USES THEREOF

This is a divisional of application Ser. No. 09/396,492 filed Sep. 14, 1999, itself a divisional of application Ser. No. 08/772,440 filed Dec. 20, 1996, now issued U.S. Pat. No. 6,046,158, the entire disclosure of which is incorporated herein by reference without disclaimer and to which benefit of priority is claimed. The government owns rights in the present invention pursuant to grant numbers R01AR35068 and R01AR41150 from the National Institutes of Health.

BACKGROUND OF THE INVENTION

1. Field of the Invention

The present invention relates generally to dendritic cells and their role in T cell activation. More specifically, the invention relates to the identification and isolation of genes encoding dendritic cell surface proteins required for T cell activation. The invention further relates to the production and use of reagents that inhibit or augment dendritic cell-dependent activation of T cells.

2. Description of Related Art

Dendritic cells (DC) are unique among antigen presenting cells (APC) by virtue of their potent capacity to activate immunologically naive T cells (Steinman, 1991). DC express constitutively, or after maturation, several molecules that mediate physical interaction with and deliver activation signals to responding T cells. These include class I and class II MHC molecules, CD80 (B7-1) and CD86 (B7-2), CD40, CD11a/CD18 (LFA-1), and CD54 (ICAM-1) (Steinman, 1991; Steinman et al., 1995). DC also secrete, upon stimulation, several T cell-stimulatory cytokines, including IL-1β, IL-6, IL-8, macrophage-inflammatory protein-1α (MIP-1α) and MIP-1γ (Matsue et al., 1992; Kitajima et al., 1995; Ariizumi et al., 1995; Caux et al, 1994; Heufler et al., 1992; Schreiber et al, 1992; Enk et al., 1992; Mohamadzadeh et al., 1996). Both of these properties, adhesion molecule expression and cytokine production are shared by other APC (e.g., activated macrophages and B cells), which are substantially less competent in activating naive T cells.

T cell activation is an important step in the protective immunity against pathogenic microorganisms (e.g., viruses, bacteria, and parasites), foreign proteins, and harmful chemicals in the environment. T cells express receptors on their surface (i.e., T cell receptors) which recognize antigens presented on the surface of antigen-presenting cells. During a normal immune response, binding of these antigens to the T cell receptor initiates intracellular changes leading to T cell activation. DC express several different adhesion (and costimulatory) molecules, which mediate their interaction with T cells. The combinations of receptors (on DC) and counter-receptors (on T cells) that are known to play this role include: a) class I MHC and CD8, b) class II MHC and CD4, c) CD54 (ICAM-1) and CD11a/CD18 (LFA-1), d) ICAM-3 and CD11a/CD18, e) LFA-3 and CD2, f) CD80 (B7-1) and CD28 (and CTLA4), g) CD86 (B7-2) and CD28 (and CTLA4), and h) CD40 and CD40L (Steinman et al., 1995). Importantly, not only does ligation of these molecules promote physical binding between DC and T cells, it also transduces activation signals.

C-type lectins are a family of glycoproteins that exhibit amino acid sequence similarities in their carbohydrate recognition domains (CRD) and that bind to selected carbohydrates in a $Ca^{2+}$-dependent manner. C-type lectins have been subdivided into four categories (Vasta et al, 1994; Spiess 1990). The first group comprises type II membrane-integrated proteins, such as asialoglycoprotein receptors, macrophage galactose and N-acetyl glucosamine (GlcNac)-specific lectin, and CD23 (FcεRII). Many members in this group exhibit specificity for galactose/fucose, galactosamine/GalNac, or GlcNac residues. The second group includes cartilage and fibroblast proteoglycan core proteins. The third group includes the so-called "collectins" such as serum mannose-binding proteins, pulmonary surfactant protein SP-A, and conglutinin. The fourth group includes certain adhesion molecules which are known as LEC-CAMs (e.g., Mel-14, GMP-140, and ELAM-1).

C-type lectins are known to function as agglutinins, opsonins, complement activators, and cell-associated recognition molecules (Vasta et al., 1994; Spiess 1990; Kery, 1991). For instance, macrophage mannose receptors serve a scavenger function (Shepherd et al., 1990), as well as mediating the uptake of pathogenic organisms, including *Pneumocystis carinii* (Ezekowitz et al., 1991) and *Candida albicans* (Ezekowitz et al., 1990). Serum mannose-binding protein mimics C1q in its capacity to activate complement through the classical pathway. Importantly, genetic mutations in this lectin predispose for severe recurrent infections, diarrhea, and failure to thrive (Reid et al., 1994). Thus, C-type lectins exhibit diverse functions with biological significance.

Importantly, carbohydrate moieties do not necessarily serve as "natural" ligands for C-type lectins. For example, CD23 (FcεRII), which belongs to the C-type lectin family as verified by its binding of Gal-Gal-Nac (Kijimoto-Ochiai et al., 1994) and by its CRD sequence, is now known to recognize IgE in a carbohydrate-independent manner; an enzymatically deglycosylated form of IgE as well as recombinant (non-glycosylated) IgE produced in *E. coli* both bind to CD23 (Vercelli et al., 1989). Thus, some C-type lectins recognize polypeptide sequences in their natural ligands. Even more extreme is the recent hypothesis that a major biological function of lectins is the recognition of polypeptides, instead of carbohydrates, as suggested by the identification, from a random polypeptide library, of several polypeptide ligands for Con A, a prototypic plant lectin (Oldenburg et al., 1992).

Recently, two C-type lectins have been identified on DC surfaces. First, Jiang et al. cloned the protein recognized by the NLDC-145 mAb, one of the most widely used mAb against murine DC (Jiang et al., 1995). This protein, now termed DEC-205, was found to be a new member of the C-type lectin family, one that contains ten distinct CRD. Second, Sallusto et al. reported that human DC express macrophage mannose receptors (MMR), which also contain multiple CRD (Sallusto et al., 1995). Both receptors have been proposed to mediate endocytosis of glycosylated molecules by DC, based on the observations that: a) polyclonal rabbit antibodies against DEC-205 not only bound to DEC-205 on DC surfaces, but were subsequently internalized; b) these DC activated effectively a T cell line reactive to rabbit IgG; and c) internalization of FITC-dextran by DC was blocked effectively with mannan, a mannose receptor competitor (Jiang et al., 1995; Sallusto et al., 1995). With respect to cell type specificity, DEC-205 is now known to be also expressed, albeit at lower levels, by B cells and epithelial cells in thymus, intestine, and lung (Witmer-Pack et al., 1995; Inaba et al., 1995) and MMR is also expressed even more abundantly by macrophages (Stahl 1992). Thus, there have been no C-type lectins that are expressed in a DC-specific manner.

Since it is known that DC are far more potent than other APC in their capacity to activate immunologically naive T cells, it is probable that DC express a protein or proteins which function to activate T cells and which are not expressed by other APC. Knowledge of the structure of such a protein or proteins would prove quite valuable in many areas. For example, the purified protein(s) could be used to identify its (or their) ligands expressed by T cells. Additionally, antibodies could be raised against the purified protein(s) and used to inhibit DC-mediated T cell activation.

SUMMARY OF THE INVENTION

The present invention seeks to overcome these and other drawbacks inherent in the prior art by providing genes found to be substantially exclusively expressed by DC, but not by other APC. As such, the present invention concerns the identification of genes, termed DC-associated C-type lectin-1 and -2 (Dectin-1 and Dectin-2), which are expressed selectively by DC and encode DC surface molecules required for T cell activation. Thus, the invention is generally drawn to DNA segments encoding dectin-1 or dectin-2 proteins or polypeptides. Accordingly, the present invention provides dectin-1 or dectin-2 genes and methods of making and using such genes.

The DNA segments of the invention may be further characterized as comprising an isolated DC gene whose product is required for DC-mediated activation of T cells.

Preferred DNA segments of the invention encode a dectin-1 protein or polypeptide comprising a contiguous amino acid sequence from SEQ ID NO:2 or encode a dectin-2 protein or polypeptide comprising a contiguous amino acid sequence from SEQ ID NO:4. The DNA segments of the invention may alternatively be defined as comprising a contiguous nucleic acid sequence from SEQ ID NO:1 or SEQ ID NO:3, respectively. Further, the DNA segment may comprise a dectin-1 gene that includes a contiguous nucleic acid sequence from between position 89 and position 823 of coding sequence SEQ ID NO: 1. Alternatively, the DNA segment may comprise a dectin-2 gene that includes a contiguous nucleic acid sequence from between position 146 and position 775 of coding sequence SEQ ID NO:3.

The dectin proteins or polypeptides of the invention are typically characterized as comprising a cytoplasmic domain, a putative transmembrane domain and extracellular domains comprising generally a connecting domain and a carbohydrate recognition domain (CRD). The dectin proteins of the invention may be further characterized as being expressed on DC and binding to T cells. The dectin-1 proteins of the invention may be described as a group of glycoproteins that consist of a major band migrating as 41 kD in SDS-PAGE and at least two minor bands migrating as 40 and 33 kD. All these bands are detectable with anti-dectin-1 polyclonal antibodies in western blotting or immunoprecipitation, validating their identities. The molecular weight of the major band is reduced by about 5 kD after treatment with glycosidases, indicating its glycosylation. The dectin-2 proteins of the invention may be described as a group of (glyco)proteins consisting of a major band migrating as 26 kD in SDS-PAGE and at least three minor bands of 32, 30, and 19 kD, as detected with monoclonal antibodies against dectin-2.

The cytoplasmic domain of dectin-1 may be characterized as including an amino acid sequence from between position 1 and position 44 from SEQ ID NO:2. It may further be defined by SEQ ID NO:12. The cytoplasmic domain of dectin-2 may be characterized as including an amino acid sequence from between position 1 and position 13 from SEQ ID NO:4. It may further be defined by SEQ ID NO:24.

The transmembrane domain of dectin-1 may be characterized as including an amino acid sequence from between position 45 and position 68 from SEQ ID NO:2. It may further be defined by SEQ ID NO:6. The transmembrane domain of dectin-2 may be characterized as including an amino acid sequence from between position 14 and position 42 from SEQ ID NO:4. It may further be defined by SEQ ID NO:19.

The extracellular domains of dectin-1 may be characterized as including an amino acid sequence from between position 69 and position 244 from SEQ ID NO:2. They may further be defined by SEQ ID NO:8. Moreover, the extracellular domains of dectin-1 may be characterized as comprising a connecting domain including an amino acid sequence from between position 68 and position 118 from SEQ ID NO:2 and a CRD domain including an amino acid sequence from between position 119 and position 244 from SEQ ID NO:2. The dectin-1 connecting domain may further be defined by SEQ ID NO:25 and the dectin-1 CRD domain may further be defined by SEQ ID NO:10.

The extracellular domains of dectin-2 may be characterized as including an amino acid sequence from between position 43 and position 209 from SEQ ID NO:4. They may further be defined by SEQ ID NO:21. Moreover, the extracellular domain of dectin-2 may be characterized as comprising a connecting domain including an amino acid sequence from between position 43 and position 78 from SEQ ID NO:4 and a CRD domain including an amino acid sequence from between position 79 and position 209 from SEQ ID NO:4. The dectin-2 connecting domain may further be defined by SEQ ID NO:26 and the dectin-2 CRD domain may further be defined by SEQ ID NO:27.

In certain embodiments, the present invention provides dectin-1 genes that encode a dectin-1 protein of about 244 amino acids in length. Preferably, the dectin-1 genes encode a dectin-1 protein that has the amino acid sequence of SEQ ID NO:2. In certain other embodiments, the present invention provides dectin-2 genes that encode a dectin-2 protein of about 209 amino acids in length. Preferably, the dectin-2 genes encode a dectin-2 protein that has the amino acid sequence of SEQ ID NO:4.

In other preferred embodiments, the present invention provides dectin-1 genes that encode a dectin-1 protein or polypeptide comprising a contiguous amino acid sequence from SEQ ID NO:2. Alternatively, the present invention provides dectin-2 genes that encode a dectin-2 protein or polypeptide comprising a contiguous amino acid sequence from SEQ ID NO:4.

The dectin-1 or dectin-2 genes of the invention are preferably cDNAs, although genomic copies are by no means excluded. In fact, the genomic DNA for dectin-2 is identified as SEQ ID NO:33. The dectin-1 or dectin-2 genes may be obtained from the XS52 DC line established from murine epidermis (Xu et al., 1995), although other dectin-1 or dectin-2 gene sources are not excluded.

Additionally, dectin-1 or dectin-2 genes will encode truncated dectin-1 or dectin-2 proteins that are generally based upon the foregoing sequences, but that have certain changes. For example, one such gene may encode a "Tβ isoform" of dectin-1 which is characterized as having a 45 amino acid deletion in its connecting domain and defined by SEQ ID NO:13.

Another example of such dectin genes encoding truncated dectin proteins is a gene encoding a "Tβ isoform" of dectin-2 which is characterized as having a 65 amino acid deletion primarily in the transmembrane and connecting domains and defined by SEQ ID NO:14. Still another example is a gene encoding a "Tγ isoform" of dectin-2, characterized as having a 34 amino deletion primarily in the connecting domain and defined by SEQ ID NO:15. Further, a dectin gene of the invention may encode a "Tδ isoform" of dectin-2 which is characterized as having a 41 amino acid deletion in the C-terminus of the CRD domain in addition to the same 34 amino acid deletion seen in Tγ and defined by SEQ ID NO:16. A dectin gene of the invention may also encode a "Tε isoform" of dectin-2, characterized as having a 43 amino acid deletion within the CRD domain and defined by SEQ ID NO:17.

Biological functional equivalents and structural equivalents of the dectin-1 or dectin-2 genes as described hereinbelow are also included within the present invention.

Certain preferred dectin-1 or dectin-2 genes will comprise the nucleic acid sequences of SEQ ID NO:1 or SEQ ID NO:3, respectively. However, this is by no means limiting and is just one exemplary embodiment of the present invention. Detailed directions as how to make and use many other such dectin-1 or dectin-2 genes are included herein.

Genes of the invention may also be operatively linked to other protein-encoding nucleic acid sequences. This will generally result in the production of a fusion protein following expression of such a nucleic acid construct. Both N-terminal and C-terminal fusion proteins are contemplated.

Virtually any protein- or polypeptide-encoding DNA sequence, or combinations thereof, may be fused to a dectin-1 or dectin-2 sequence in order to encode a fusion protein. This includes DNA sequences that encode targeting polypeptides, therapeutic proteins, proteins for recombinant expression, proteins to which one or more targeting polypeptides is attached, protein subunits and the like. The preferred sequence for fusion to a dectin-1 or dectin-2 gene of the invention is 6× Histidine (SEQ ID NO:28).

Another embodiment of the invention may generally be described as a nucleic acid segment characterized as a nucleic acid segment comprising a sequence region that consists of at least 14 contiguous nucleotides that have the same sequence as, or are complementary to, 14 contiguous nucleotides of SEQ ID NO:1 or SEQ ID NO:3. Alternatively, the nucleic acid segment of the invention may be characterized as a nucleic acid segment of from 14 to about 10,000 nucleotides in length that hybridizes to the nucleic acid segment of SEQ ID NO:1 or SEQ ID NO:3, or the complement thereof, under standard hybridization conditions.

Preferred nucleic acid segments comprise a sequence region of at least 14 contiguous nucleotides from SEQ ID NO:1 or SEQ ID NO:3 or the complement thereof. Other preferred nucleic acid segments comprise segments that hybridize to the nucleic acid segment of SEQ ID NO:1 or SEQ ID NO:3 or the complement thereof. In more preferred embodiments, the segment is about 25 nucleotides in length. Alternatively, the segment may be up to about 2.4 kilobasepairs in length for dectin-1 or about 1.2 kilobasepairs in length for dectin-2.

The invention further includes DNA segments comprising the 5' untranslated regions (5' UTR) and 3' UTR of dectin-1 or dectin-2 cDNA and 5'-flanking regions and 3'-flanking regions of dectin-1 or dectin-2. These 5' UTR and 3' UTR genomic DNA sequences and 5'-flanking and 3'-flanking sequences are important in terms of regulating DC-specific transcription of the dectin-1 or dectin-2 gene. It has been found that the 5' flanking sequence may be particularly useful in targeting the transcription of foreign genes into DC. For example, an isolated putative promoter fragment (about 3.2 kb) of the dectin-2 gene (SEQ ID NO:34) has been shown to drive transcription of the luciferase gene in the XS552 DC line, but not in other cell types. Thus, in one aspect of the invention, a DNA segment comprising the 5'-flanking regions of dectin-2 is operatively linked to a heterologous gene or a DNA segment that encodes a selected protein. Examples of DNA segments to which the 5'-flanking regions may be linked are listed in Table 4 at pages 60–66.

Another aspect of the invention generally involves a purified dectin-1 or dectin-2 protein or polypeptide. In certain embodiments, the protein or polypeptide of the invention may be operatively linked to a selected polypeptide sequence. A preferred polypeptide sequence to be operatively linked to the dectin-1 or dectin-2 protein or polypeptide of the invention is 6× Histidine (SEQ ID NO:28). It is also contemplated that purified polypeptides of between about 5 to about 20 amino acids in length comprising a sequence from SEQ ID NO:2 or SEQ ID NO:4 be encompassed by the invention. One such preferred sequence may be defined by SEQ ID NO:11.

Still other embodiments of the invention may include a composition comprising a purified dectin-1 or dectin-2 protein or polypeptide. In such embodiments, the protein or polypeptide of the invention may be linked to a selected non-dectin polypeptide sequence. A preferred non-dectin polypeptide sequence to be linked to the protein or polypeptide in the composition is 6× Histidine (SEQ ID NO:28). In certain preferred compositions, the protein or polypeptide comprises an isolated dectin-1 or dectin-2 extracellular domain. The non-dectin polypeptide sequence will preferably be linked covalently, although other types of linkages known in the art are within the scope of the invention.

Recombinant vectors and plasmids form another important aspect of the present invention. In such vectors, the dectin-1 or dectin-2 gene is positioned under the transcriptional control of a promoter, generally a promoter operative in a mammalian or human cell. "Positioned under the transcriptional control of" means that the dectin-1 or dectin-2 sequence is positioned downstream from and under the transcriptional control of the promoter such that the promoter is capable of directing expression of the encoded dectin-1 or dectin-2 protein in a mammalian or human host cell upon introduction of the vector into such a cell.

The recombinant vectors of the invention will thus generally comprise a dectin-1 or dectin-2 gene operatively positioned downstream from a promoter, wherein the promoter is capable of directing expression of the dectin-1 or dectin-2 gene in a mammalian or human cell. Preferably the promoter will direct expression of dectin-1 or dectin-2 in an amount sufficient to allow dectin-1 or dectin-2 detection. Such promoters are thus "operative" in mammalian and human cells.

Expression vectors and plasmids in accordance with the present invention may comprise one or more constitutive promoters, such as viral promoters or promoters from mammalian genes that are generally active in promoting transcription. Examples of constitutive viral promoters include the HSV, TK, RSV, SV40 and CMV promoters, of which the CMV promoter is a currently preferred example. Examples of constitutive mammalian promoters include various housekeeping gene promoters, as exemplified by the β actin promoter.

Inducible promoters and/or regulatory elements are also contemplated for use with the expression vectors of the invention. Examples of suitable inducible promoters include promoters from genes such as cytochrome P450 genes, heat shock protein genes, metallothionein genes, hormone-inducible genes, such as the estrogen gene promoter, and such like. Promoters that are activated in response to exposure to ionizing radiation, such as fos, jun and egr-1, are also contemplated.

Tissue-specific promoters and/or regulatory elements will be useful in certain embodiments. Examples of such promoters that may be used with the expression vectors of the invention include promoters from the liver fatty acid binding (FAB) protein gene, specific for colon epithelial cells; the keratin genes, specific for keratinocytes; the insulin gene, specific for pancreatic cells; the transphyretin, α1-antitrypsin, plasminogen activator inhibitor type 1 (PAI-1), apolipoprotein AI and LDL receptor genes, specific for liver cells; the myelin basic protein (MBP) gene, specific for oligodendrocytes; the glial fibrillary acidic protein (GFAP) gene, specific for glial cells; OPSIN, specific for targeting to the eye; and the neural-specific enolase (NSE) promoter that is specific for nerve cells.

The construction and use of expression vectors and plasmids is well known to those of skill in the art. Virtually any mammalian cell expression vector may thus be used connection with the genes disclosed herein.

Preferred vectors and plasmids will be constructed with at least one multiple cloning site. In certain embodiments, the expression vector will comprise a multiple cloning site that is operatively positioned between a promoter and a dectin-1 or dectin-2 gene sequence. Such vectors may be used, in addition to their uses in other embodiments, to create N-terminal fusion proteins by cloning a second protein-encoding DNA segment into the multiple cloning site so that it is contiguous and in-frame with the dectin-1 or dectin-2 sequence.

In other embodiments, expression vectors may comprise a multiple cloning site that is operatively positioned downstream from the expressible dectin-1 or dectin-2 gene sequence. These vectors are useful, in addition to their uses, in creating C-terminal fusion proteins by cloning a second protein-encoding DNA segment into the multiple cloning site so that it is contiguous and in-frame with the dectin-1 or dectin-2 sequence.

Vectors and plasmids in which a second protein- or RNA-encoding nucleic acid segment is also present are, of course, also encompassed by the invention, irrespective of the nature of the nucleic acid segment itself.

A second reporter gene may be included within an expression vector of the present invention. The second reporter gene may be comprised within a second transcriptional unit. Suitable second reporter genes include those that confer resistance to agents such as neomycin, hygromycin, puromycin, zeocin, mycophenolic acid, histidinol and methotrexate.

Expression vectors may also contain other nucleic acid sequences, such as IRES elements, polyadenylation signals, splice donor/splice acceptor signals, and the like.

Particular examples of suitable expression vectors are those adapted for expression using a recombinant adenoviral, recombinant adeno-associated viral (AAV) or recombinant retroviral system. Vaccinia virus, herpes simplex virus, cytomegalovirus, and defective hepatitis B viruses, amongst others, may also be used.

In certain embodiments, the expression vector or plasmid may comprise a dectin-1 reporter gene that has the nucleic acid sequence of SEQ ID NO:1. In certain other embodiments, the expression vector or plasmid may comprise a dectin-2 reporter gene that has the nucleic acid sequence of SEQ ID NO:3.

Recombinant host cells form another aspect of the present invention. Such host cells will generally comprise at least one copy of an isolated dectin-1 or dectin-2 gene. Preferred cells for expression purposes will be prokaryotic host cells or eukaryotic host cells. Accordingly, cells such as bacterial, yeast, fungal, insect, nematode and plant cells are also possible. Most preferably, the host cell will be a bacterial host cell. An example of a preferred bacterial host cell is *E. coli*. Alternatively, an example of a preferred eukaryotic host cell is a dendritic cell. However, it will be understood that other cell types are not excluded from those of the invention.

In certain embodiments, the recombinant host cells will preferably incorporate a dectin-1 or dectin-2 gene in a manner effective to allow the cell to express, or to be stimulated to express, dectin-1 or dectin-2, most preferably, in an amount sufficient to allow dectin-1 or dectin-2 detection. The recombinant host cell will thus preferably include a dectin-1 or dectin-2 gene that was introduced into the cell by means of a recombinant vector.

In certain embodiments, the recombinant host cell will express the dectin-1 or dectin-2 gene to produce the encoded dectin-1 or dectin-2 protein, preferably, in an amount sufficient to allow dectin-1 or dectin-2 detection. The expressed dectin-1 protein or polypeptide preferably includes a contiguous amino acid sequence from SEQ ID NO:2. The expressed dectin-2 protein or polypeptide preferably includes a contiguous amino acid sequence from SEQ ID NO:4.

The recombinant dectin-1 or dectin-2 proteins or polypeptides of the invention may, in certain embodiments, be prepared by expressing a dectin-1 or dectin-2 protein or polypeptide in a recombinant host cell and purifying the expressed dectin-1 or dectin-2 protein or polypeptide away from total recombinant host cell components.

Examples of suitable recombinant host cells include VERO cells, HeLa cells, cells of Chinese hamster ovary (CHO) cell lines, COS cells, such as COS-7, and I138, BHK, HepG2, 3T3, RIN, MDCK, A549, PC12, K562 and 293 cells.

Cells of primary cell lines that have been established after removing cells from a mammal and culturing the cells for a limited period of time are also included within the cells of the present invention. These cells may be engineered by the hand of man and returned to the same host animal from which they were originally recovered. Such cells that contain a dectin-1 or dectin-2 gene fall within the scope of the invention, irrespective of their location.

Naturally, recombinant cells also include those cells that are located within the body of an animal or human subject, as may have been targeted by gene therapy. These cells include all those that comprise at least one copy of a dectin-1 or dectin-2 gene or vector, irrespective of the manner in which gene was acquired, e.g., by transfection, infection and the like.

In certain particular embodiments, recombinant host cells that comprise a dectin-1 gene that comprises the nucleic acid sequence of SEQ ID NO:1 are contemplated. In certain other particular embodiments, recombinant host cells that comprise a dectin-2 gene that comprises the nucleic acid sequence of SEQ ID NO:3 are contemplated.

Also obtained from the invention are cells engineered not to express or to express at significantly reduced levels dectin-1 or dectin-2. Such cells may be produced by selecting a cell, preferably a DC, and providing to the cell an expression construct comprising a polynucleotide encoding a dectin-1 or dectin-2 gene wherein the polynucleotide is positioned antisense to and operatively linked to a promoter.

The expression of such a polynucleotide effectively produces a cell deficient in dectin-1 or dectin-2.

In other embodiments the present invention provides a method for the preparation of recombinant host cells which produce significantly reduced amounts or even "knockout" the production of dectin-1 or dectin-2. It is contemplated that these recombinant host cells will be prepared by using one or more means that are well known to those of skill in the art. For example, gene expression can be inhibited by the incorporation of constructs for antisense DNA or RNA into the genome, deletions or mutations of the endogenous dectin-1 or dectin-2 genes can rendered them nonfunctional or even nucleic acids encoding ribozymes—RNA-cleaving enzymes—that specifically cleave dectin-1 or dectin-2 mRNA can be introduced into the recombinant host cells.

The term "knockout" refers to partial or complete suppression of the expression of at least a portion of a protein encoded by an endogenous DNA sequence, e.g. dectin-1 or dectin-2, in a cell. The term "knockout construct" refers to a nucleic acid sequence that is designed to decrease or suppress expression of a protein encoded by endogenous DNA sequences in a cell.

It is contemplated that these recombinant host cells will be incorporated into knockout mammals such that the production of dectin-1 or dectin-2 or dectin-like proteins is suppressed in DCs. The preparation of knock out and transgenic animals is well known to those of skill in the art and is described in U.S. Pat. Nos. 5,434,340, 5,530,179 and 5,557,032, incorporated herein by reference.

The invention further provides methods for producing animals that overexpress dectin-1 or dectin-2. These methods generally comprise introducing animal cells such as mouse, rat, pig, human, chicken or fish teratocarcinoma cells, into an animal, such as a mouse, rat, pig, or human (or even chicken or fish), respectively, said animal cells having been treated in vitro to insert therein a DNA segment encoding a dectin-1 or dectin-2 polypeptide, said animal cells expressing in vivo in said animal an amount of said dectin-1 or dectin-2 polypeptide which is greater than the amount of dectin-1 or dectin-2 polypeptide normally expressed in said cells. The same methods may be used to produce "immunoprotected" cattles, by introducing dectin-1 or dectin-2 cDNA into other animal species (e.g., cow, sheep, horse).

In another aspect, the invention provides methods of engineering animals to not express dectin-1 or dectin-2. Such methods generally comprise obtaining cells from the animal, providing an expression construct to the cells comprising a polynucleotide encoding a dectin-1 or dectin-2 gene wherein the polynucleotide is positioned antense to and operatively linked to a promoter, wherein expression of the polynucleotide produces cells deficient in dectin-1 or dectin-2 production, and re-introducing the engineered cells into the animal from which they were taken. It is also contemplated that anti-sense RNA or DNA insertion could be used to engineer animals to not express dectin-1 or dectin-2.

Many methods of using dectin-1 or dectin-2 genes are obtained from the present invention. For example, the invention provides a method for inhibiting the interaction of a DC with a T cell, comprising contacting a composition comprising DC and T cells with an effective amount of an agent that inhibits the interaction of dectin-1 or dectin-2 with the T cell. The agent that inhibits the interaction of dectin-1 or dectin-2 with the T cell may be an antibody. Currently available antibodies against dectin-1 or dectin-2 include: a) affinity purified rabbit anti-peptide antibodies against dectin-1 (BAD1-Pep), b) rabbit antibodies against His-dectin-1 (BAD1-Rhi), c) rat antibodies against His-dectin-1 (TAD1-Rhi), d) rabbit antibodies against His-dectin-2 (BAD2-Rhi), e) rat antibodies against His-dectin-2 (TAD2-Rhi), and f) rat monoclonal antibodies against His-dectin-2 (MAD2-Rhi). In preferred embodiments, the antibody will be the antibody designated BAD1-Pep, BAD1-Rhi or TAD1-Rhi. In certain other preferred embodiments, the antibody will be the antibody designated BAD2-Rhi, TAD2-Rhi or MAD2-Rhi.

In certain embodiments, the composition comprising DC and T cells will be located within an animal and the agent will be administered to the animal. For example, the method may be a method of treating inflammation, comprising administering to an animal a therapeutically effective amount of an agent that inhibits the interaction of dectin-1 or dectin-2 with T cells.

In a general sense, the invention provides a method for identifying an effector of DC interaction with T cells. This method comprises admixing a dectin-1 or dectin-2 composition with a population of T cells and a candidate substance and identifying a candidate substance that alters the interaction of dectin-1 or dectin-2 with the T cells. In certain embodiments, the composition comprising dectin-1 or dectin-2 comprises engineered cells that express recombinant dectin-1 or dectin-2. Alternatively, the dectin-1 or dectin-2 is expressed on the surface of a DC.

In other embodiments, the dectin-1 or dectin-2 composition comprises purified dectin-1 or dectin-2 linked to a detectable label; or a population of DC that express dectin-1 or dectin-2. The candidate substance that affects the interaction of dectin-1 or dectin-2 with T cells may be identified by an alteration in dectin-1 or dectin-2 binding to T cells or by an alteration in dectin-1 or dectin-2 mediated alteration of T cells. This described method may be used to identify effectors which stimulate the interaction of dectin-1 or dectin-2 with T cells or, in the alternative, to identify effectors which inhibit the interaction of dectin-1 or dectin-2 with T cells, depending on the effect observed.

More specific methods obtained from the invention are methods for identifying an inhibitory agent, or a stimulatory agent, comprising admixing a dectin-1 or dectin-2 composition with a population of T cells and a candidate substance and identifying a candidate substance that inhibits, or stimulates, the interaction of dectin-1 or dectin-2 with the T cells. Preferably, the dectin-1 or dectin-2 of this method will be expressed on the surface of a DC. Alternatively, the composition comprising dectin-1 or dectin-2 may comprise engineered cells that express recombinant dectin-1 or dectin-2. In yet another embodiment, the dectin-1 or dectin-2 composition may comprise purified dectin-1 or dectin-2 operatively linked to a detectable label. The dectin-1 or dectin-2 composition may alternatively comprise a population of DC that express dectin-1 or dectin-2.

The candidate substance that inhibits, or stimulates, the interaction of dectin-1 or dectin-2 with T cells may be identified by inhibition, or stimulation, of dectin-1 or dectin-2 binding to the T cells. Alternatively, the candidate substance that inhibits, or stimulates, the interaction of dectin-1 or dectin-2 with T cells may be identified by inhibition, or stimulation, of dectin-1 or dectin-2 mediated activation of T cells.

More specifically, the invention also provides methods for identifying an inhibitory agent, or a stimulatory agent, comprising the steps of:

(a) admixing a first composition comprising a population of recombinant cells expressing dectin-1 or dectin-2 with a second composition comprising a population of T cells;
(b) incubating the admixture with a candidate substance;
(c) testing said admixture for T cell activation; and
(d) identifying a candidate substance that inhibits, or stimulates, the activation of T cells.

The invention further provides agents that inhibit, or stimulate, the binding of dectin-1 or dectin-2 to T cells. Alternatively, the invention provides agents that inhibit, or stimulate, dectin-1 or dectin-2-mediated activation of T cells. In preferred embodiments, the agent of the invention will be formulated in a pharmaceutical acceptable medium.

In certain embodiments, the agent of the invention may be prepared by a process comprising:
(a) admixing a first composition comprising a population of recombinant cells expressing dectin-1 or dectin-2 with a second composition comprising a population of T cells;
(b) incubating the admixture with a candidate substance;
(c) testing said admixture for T cell adhesion to dectin-1 or dectin-2 expressing cell; and
(d) identifying a candidate substance that inhibits, or stimulates, T cell adhesion.

The same methods may be employed to search for agents that augment DC-induced activation of T cells or DC-T cell adhesion.

The present invention further provides a method for purifying T cells. Preferably, the method comprises the steps of:
(a) preparing an immobilized dectin-1 or dectin-2 composition comprising a dectin-1 or dectin-2 protein or polypeptide linked to a solid support;
(b) contacting said immobilized dectin-1 or dectin-2 composition with a test composition suspected of containing T cells under conditions effective to allow T cell binding to said dectin-1 or dectin-2;
(c) removing unbound components from said test composition; and
(d) releasing bound T cells from said immobilized dectin-1 or dectin-2 composition.

Likewise, DC may be purified in a similar manner by using antibodies against dectin-1 or dectin-2.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A and FIG. 1B Deduced amino acid sequence of dectin-1 and its homology with members of the C-type lectin family. FIG. 1A. Deduced amino acid sequence of dectin-1 is shown, segmented into a cytoplasmic domain, a transmembrane domain, and an extracellular domain containing a putative CRD sequence. Asterisks indicate the invariant residues of C-type lectins proposed by Spiess (1990). Open and closed triangles indicate a tyrosine residue and putative N-glycosylation sites, respectively. FIG. 1B. A putative CRD sequence was aligned with members of the C-type lectin family, including HL-1 and HL-2, CD23 and CD69 in mice (m), rats (r), and humans (h).

FIG. 2A. Total RNA was isolated from XS52 DC, J774 and Raw macrophages, 7-17 dendritic epidermal T cells (DETC), HDK-1 Th1 cells, D10 Th2 cells, 5C5 B cell hybridoma, Pam 212 keratinocytes, and NS01 fibroblasts (a) or from the indicated tissues in adult BALB/c mice (c). FIG. 2B. XS52 cells and J774 cells were cultured for 24 hours in the presence or absence of GM-CSF (10 ng/ml) or CSF-1 (10 ng/ml) before isolation of RNA. These RNA samples (10 μg/lane) were then examined by northern blotting for dectin-1 or GAPDH. FIG. 2C. Epidermal cells isolated from adult BALB/c mice were examined for dectin-1 mRNA expression by RT-PCR™. Some samples were treated with anti-Ia monoclonal antibody (MAb) plus complement to deplete Langerhans cells (DC in skin), (Ariizumi 1995; Matsue 1992) and the extent of this depletion was assessed by measuring IL-1β mRNA, which is known to be expressed exclusively by Langerhans cells within murine epidermal cells.

FIG. 3B shows the results for XS52 DC. FIG. 3C shows the results for J774. FIG. 3D shows the results for 7–17 DETC. FIG. 3E shows the results for PAM 212.

(FIG. 3F). Dectin-1 expression was examined in the FL-1 channel with affinity purified anti-dectin-1 antibodies (BAD1-Pep). About 20–40% of the CD11c-positive cells (i.e., DC) exhibited significant label with anti-dectin-1. (FIG. 3G). No significant dectin-1 immunolabeling was observed in the CD11c-negative population. These results indicate that dectin-1 protein is expressed at detectable levels and on cell surfaces by a subpopulation of splenic DC and that dectin-1 protein expression occurs almost exclusively within the DC population.

FIG. 4A is a histogram showing the incubation of splenic T cells with mAb against the His tag or an isotype-matched control mouse IgG without recombinant His-dectin-1. FIG. 4B is a histogram showing the same with the addition of the recombinant His-dectin-1. FIG. 4C shows the CD4$^+$ HDK-1 T cell clone stained with anti-His tag or control IgG.

FIG. 4F shows $^3$H-thymidine uptake (cpm×10$^{-3}$) for HDK-1 T cell clone (KLH specific). FIG. 4G shows $^3$H-thymidine uptake (cpm×10$^{-3}$) for in vivo primed T cells (KLH specific). FIG. 4H shows $^3$H-thymidine uptake (cpm×10$^{-3}$) for 5S8 T cell clone (DNBS specific). FIG. 4I shows $^3$H-thymidine uptake (cpm×10$^{-3}$) for allogeneic T cells. Data shown are the mean±SD (n=3) of $^3$H-thymidine, representing at least three independent studies.

FIG. 4K shows the profile for cells having neither anti-dectin-1 mAb nor the control mAb. FIG. 4L shows the profile for cells cultured with anti-dectin-1. FIG. 4M shows the profile for cells cultured with control IgG.

FIG. 5A: 5'-UTR dectin-1 cDNA was analyzed for sequences that are known to serve as transcriptional regulatory motifs. The transcription initiation site as determined by primer extension assay is shown with an arrow. Note that there exist in the upstream from the transcription initiation site a conserved TATA box and several sequences known to bind typical transcription regulatory proteins. A 3.5 kb fragment isolated from the 5'-flanking region of the dectin-2 gene was inserted in the upstream of the reporter gene, luciferase. This construct was then introduced into the XS52 DC, J774 macrophages, Pam 212 keratinocytes, or NS47 fibroblasts. Two days after transfection, cell extracts were examined for luciferase activity. Data shown are transcriptional activities of this construct (FIG. 5C) and a control construct containing only the luciferase gene (FIG. 5B), expressed as % of luciferase activities compared with samples transfected with a positive construct containing SV40 promoter-driven luciferase gene.

FIG. 6A: cDNA encoding dectin-1 and dectin-2 isoforms have been cloned from the cDNA library from XS52 DC. Sequencing of these clones have revealed that they contain one or two deletions in the nucleotide sequences of the original, full-length dectin-1 or dectin-2 cDNA and that they encode polypeptides lacking one or two amino acid stretches. Data shown are schematic illustration of deduced amino acid structures of different isoforms. FIG. 6B: Genomic DNA fragments for dectin-2 have been cloned and sequenced. Data shown are the exon-intron organization of the dectin-2 gene (top). Based on this sequence, it has been identified that truncated mRNAs for dectin-2 represent the transcripts from which one or two exons are deleted entirely or partially (bottom).

DESCRIPTION OF ILLUSTRATIVE EMBODIMENTS

A. Introduction

Figure 2A:
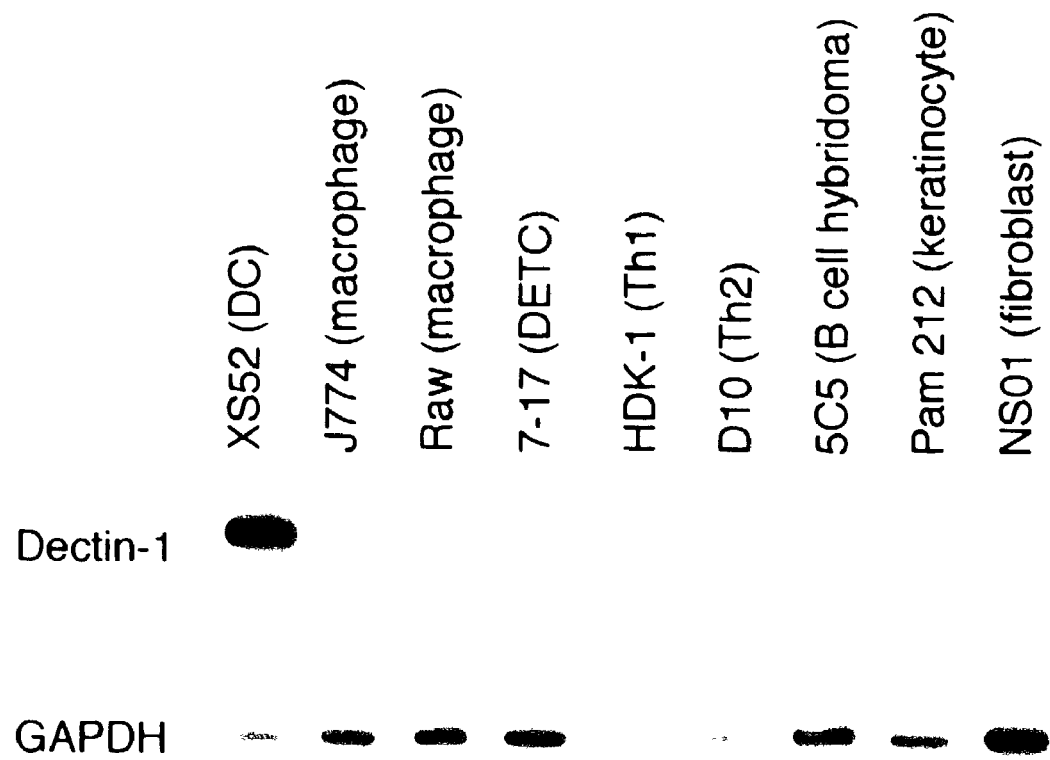
FIG. 2A, FIG. 2B and FIG. 2C. Scanned images of cell and tissue specific expression of dectin-1.

It has been known for some time that DC possess a potent capacity to activate naive T cells. Nevertheless, T cell-mediated inflammatory diseases have traditionally been difficult to treat partially due to the fact that adhesion molecules on DC known to activate T cells are also expressed by other antigen presenting cells (APC). These other APC are substantially less competent in activating naive T cells. This made producing vaccines or immunogens difficult because no molecule or protein was known which was unique to a specific APC and which possessed a significant capacity to activate T cells. The present inventors have shown that DC express molecules that are undetectable in other APC, that contain single carbohydrate recognition domains in their extracellular domains, and that play a functional role during the activation of naive T cells. More specifically, dectin-1 and/or dectin-2 operate to mediate the physical contact of DC with T cells. It is also contemplated that dectin-1 and/or dectin-2 mediate the physical contact of DC with B cells and other cell types, such as NK cells, endothelial cells, keratinocytes, and even DC themselves.

The inventors have characterized these molecules as comprising, respectively, 244 amino acids, as defined in SEQ ID NO:2, and 209 amino acids, as defined in SEQ ID NO:4. Further, the identified molecules each consist of a cytoplasmic domain; a putative transmembrane domain; and extracellular domains comprising a carbohydrate recognition domain (CRD) and a non-CRD ("connecting") domain. Due to their similarities with the type II membrane-integrated C-type (calcium-dependent) lectin proteins, the inventors have labeled the identified 244 amino acid molecule "dectin-1" and the 209 amino acid molecule "dectin-2."

The extracellular domains of dectin-1 may be further characterized as comprising a region, defined by amino acids 119–244 of SEQ ID NO:2 or SEQ ID NO:8, that exhibits significantly homology (up to 35.6% similarity) with CRDs of currently recognized C-type lectins, such as the phospholipase A2 receptor (PA2R), asiaglycoprotein receptors or hepatic lectin (HL-1 and HL-2), CD23 (low affinity IgE receptor: FcεRII), and CD69 (early activation marker). Similarly, the CRD domains of dectin-2 may be further characterized as comprising a region, defined by amino acids 79–209 of SEQ ID NO:4 or SEQ ID NO:21.

After comparing CRD sequences, Spiess has postulated that 13 amino acids are relatively well conserved in many C-type lectins. These invariant residues include six cysteines, which appear to play a critical role in forming disulfide bridge frameworks (Spiess 1990). While the putative CRD sequence of dectin-1 showed only limited similarity with that of dectin-2, both exhibited significant homologies with CRD sequences of hepatic lectin (HL1) and HL2, macrophage galactose and GluNac-specific lectin (MGL), CD23, and CD69 (early activation marker). Importantly, the putative CRD sequence in dectin-1 contains 10 out of 13 of these invariant residues, including all six cysteine residues (SEQ ID NO:10). Additionally, the putative CRD sequence in dectin-2 contains all 13 of these invariant residues (SEQ ID NO:23).

One or more truncated forms of dectin-1 and dectin-2 transcripts have also been observed. Using methods similar to those developed and employed in previous studies, the inventors have determined the identities of the truncated dectin-1 and dectin-2 mRNAs. The truncated form of dectin-1, termed "Tβ isoform," (SEQ ID NO:13) was found to contain a 45 amino acid deletion in the connecting domain, compared with the full-length dectin-1 (Tα) (SEQ ID NO:2). The inventors have also identified, in addition to the full length dectin-2 (Tα) (SEQ ID NO:4), four isoforms: a) Tβ with a 65 amino acid deletion primarily in the transmembrane and connecting domains (SEQ ID NO:14); b) Tγ with a 34 amino acid deletion primarily in the connecting domain (SEQ ID NO:15); c) Tδ with a 41 amino acid deletion in the C-terminus of the CRD domain, in addition to the same 34 amino acid deletion seen in Tγ (SEQ ID NO:16); and d) Tε with a 43 amino acid deletion within the CRD domain (SEQ ID NO:17). These truncated forms of dectin-1 or dectin-2 transcripts have been detected not only in the XS52 DC line, but also in spleen cells and epidermal cells. Therefore, it is contemplated that DC in normal tissues express mRNA for different isoforms of dectin-1 and dectin-2.

The inventors have identified by western blotting that anti-dectin-1 antibodies (BAD1-Pep and BAD1-Rhi) detect multiple bands, ranging from 33 kD to 41 kD, in the XS52 DC extract. The inventors have also identified with anti-dectin-2 monoclonal antibodies (MAD2-Rh1) multiple bands from 19 kD to 32 kD in this extract. These results suggest that DC produce different isoforms of dectin-1 and dectin-2 at protein levels.

Figure 6A:
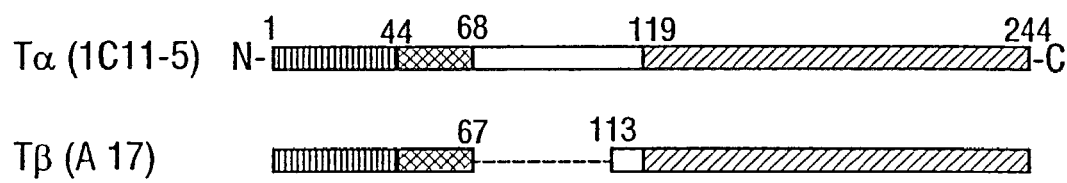
FIG. 6A and FIG. 6B: Molecular structures of dectin-1 and dectin-2 isoforms.
Figure 6A:
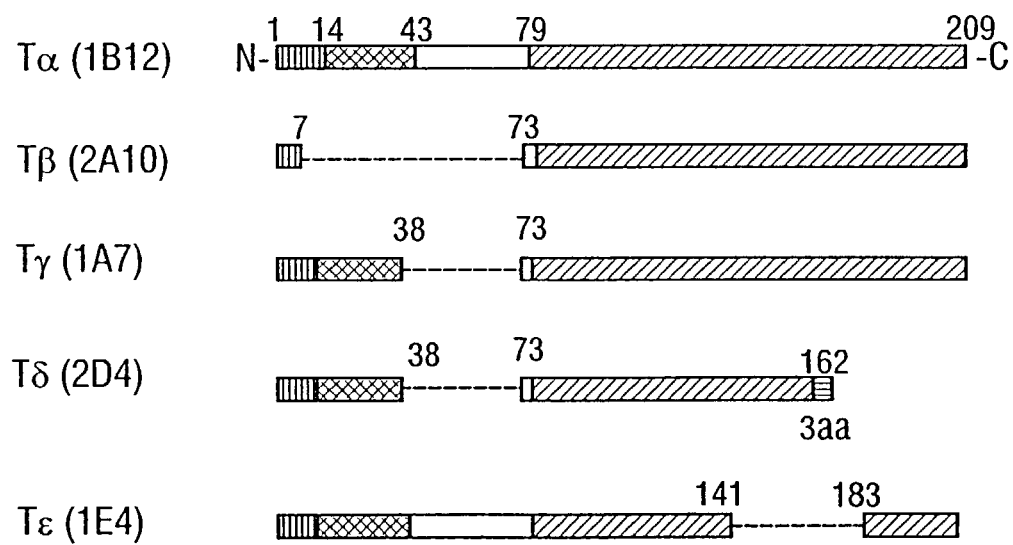
Figure 6B:
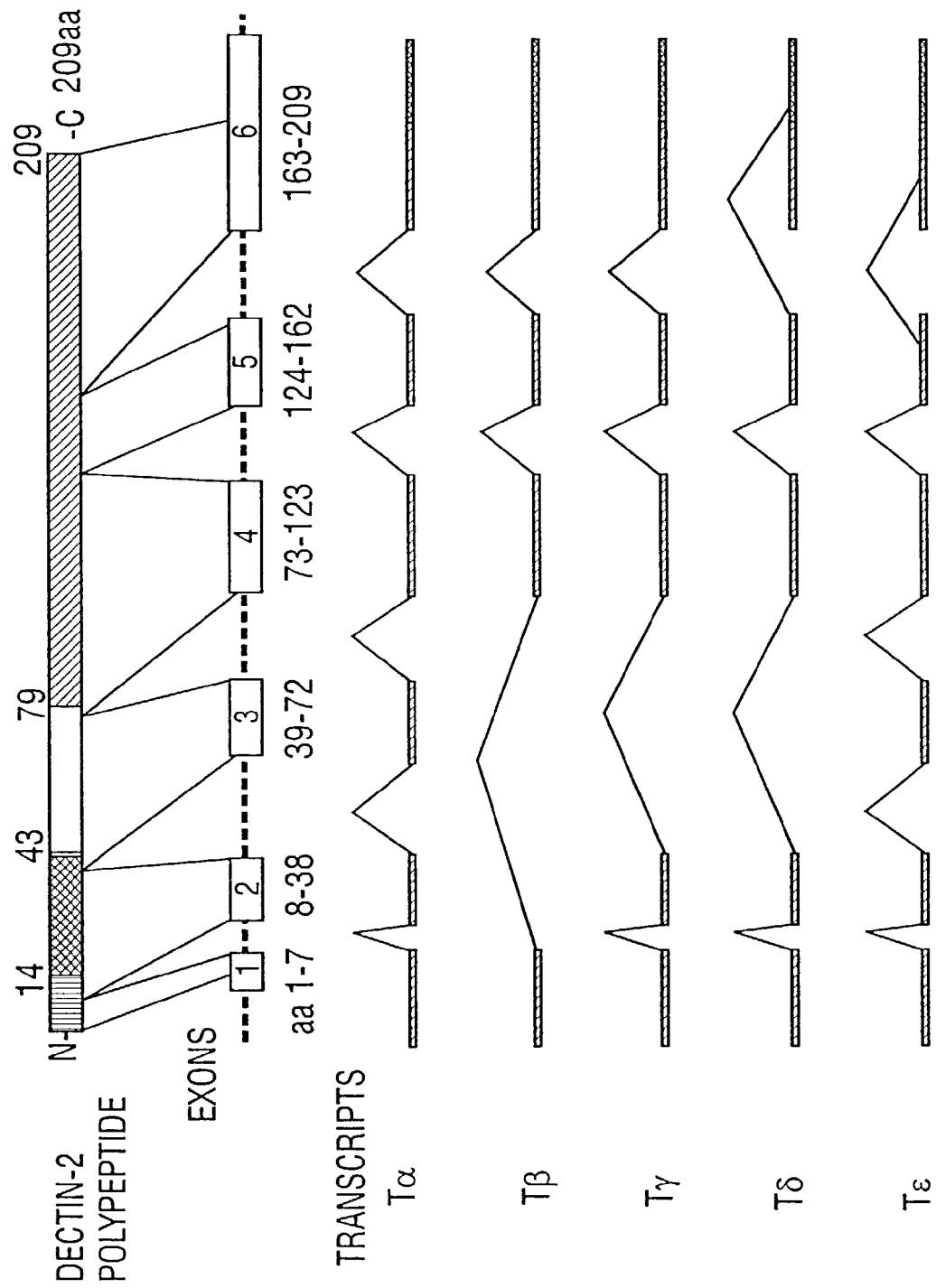

The inventors have observed that different dectin-2 isoforms are produced by a mechanism known as alternative splicing. The genomic DNA (SEQ ID NO:35) for dectin-2 contains six exons with exon 1 (SEQ ID NO:37) encoding primarily the cytoplasmic domain (SEQ ID NO:37), exon 2 (SEQ ID NO:38) encoding primarily the transmembrane domain, exon 3 (SEQ ID NO:39), encoding primarily the connecting domain, and exons 4, 5, and 6 (SEQ ID NO:40, SEQ ID NO:41 and SEQ ID NO:42, respectively) encoding the CRD (SEQ ID NO:35). Importantly, the truncated dectin-2 mRNAs described above have been identified to contain total or partial deletion of one or two of these exons (see FIG. 6B).

As used hereinbelow, the terms dectin-1 and/or dectin-2 should be interpreted to include not only the full length molecules but also the isoforms described herein, glycosylated forms as well as non-glycosylated forms of the molecules, and other members of the dectin family.

Different isoforms may be purified from extracts of DC preparations (e.g., XS52 DC line) by immunoprecipitation using polyclonal anti-dectin-1 or anti-dectin-2 antibodies or monoclonal antibodies (MAb) against different domains of dectin-1 or dectin-2. Different isoforms may also be produced in recombinant forms. For this aim, cDNA encoding each isoform will be expressed in bacteria, yeasts, insect cells, or mammalian cells and the expressed proteins purified using antibodies against dectin-1 or dectin-2. In fact, the inventors have cloned and sequenced several different cDNA that encode different isoforms (SEQ ID NO: 13 through SEQ ID NO:17).

The inventors contemplate that the dectin-1 and/or dectin-2 proteins and/or polypeptides described herein not only function to mediate the physical contact of DC with T cells, but that they also mediate effective recognition and uptake of specific antigens (e.g., carbohydrate moieties or peptide moieties of antigens). Further, the proteins and/or polypeptides described herein may serve as receptors of soluble molecules (e.g., cytokines, growth factors, chemical mediators); as homing/adhesion/rolling receptors mediating the migration of DC; as signaling receptors, thereby regulating the function of DC (e.g., secretion of cytokines, expression of other adhesion/costimulatory molecules); as ligands of signaling receptors on T cells, thereby regulating their function (e.g., clonal activation versus clonal anergy/apoptosis, differentiation into Th 1 versus Th 2 subsets); and/or as soluble factors that modulate the immune reactions. Additionally, the proteins and/or polypeptides of the invention may transduce activation signals into non-T cell populations, e.g., B cells or other cell types, which also recognize dectin-1 and/or dectin-2.

B. DNA and RNA Segments for Dectin-1 or Dectin-2
1. DNA Segments

Important aspects of the present invention concern isolated DNA segments and recombinant vectors encoding dectin-1 and/or dectin-2, and the creation and use of recombinant host cells through the application of DNA technology that express dectin-1 and/or dectin-2.

More specifically, the present invention concerns mammalian DNA segments, isolated away from other mammalian genomic DNA segments or total chromosomes. Preferred sources for the dectin-1 or dectin-2 DNA segments of the invention are human gene sequences. In cloning a dectin sequence of the invention, one may advantageously choose an established DC line. But other sources will be equally appropriate, such as cDNA or genomic libraries including at least some DC. In particular, the DNA segments of the invention have been found to be isolatable from a long-term DC line established from the epidermis of newborn BALB/c mice, termed XS52. The DNA segments of the invention are capable of conferring dectin-1-like activity or properties, such as defined herein below, in to the recombinant host cell when incorporated As used herein, the term "DNA segment" refers to a DNA molecule that has been isolated substantially free of total genomic DNA and chromosomes of a particular species. Therefore, a DNA segment encoding dectin-1 or dectin-2 refers to a DNA segment that contains dectin-1 or dectin-2 coding sequences yet is isolated away from, or purified free from, total genomic DNA of the spleen or thymus tissues known to contain relatively large numbers of DC, or of the XS52 line. Included within the term "DNA segment", are DNA segments and smaller fragments of such segments, and also recombinant vectors, including, for example, plasmids, cosmids, phage, viruses, and the like.

The inventors have cloned and sequenced not only the cDNA for the coding sequences of dectin-1 and dectin-2, but also 5' untranslated region (5'UTR) and 3'UTR. Moreover, the inventors have also cloned and sequenced the genomic DNA for dectin-2 (SEQ ID NO:35) of about 13 kb in total size. The 5'-flanking and 3'-flanking sequences are of particular importance in terms of regulating DC-specific transcription of the dectin-1 or dectin-2 gene. In this respect, the 5'-flanking sequences may be linked to a heterologous gene or to a DNA segment that encodes a selected protein and contacted with DC such that the heterologous gene or DNA segment encoding a selected protein will be expressed in the DC. As used herein, the term "heterologous gene" refers to genes other than the dectin-1 or dectin-2 genes. Examples of genes contemplated for use in the present invention are listed in Table 4 at pages 60–66. In fact, the inventors have isolated a putative promoter fragment (about 3.2 kb) of the dectin-2 gene (SEQ ID NO:34), a fragment that has been proven to drive transcription of the luciferase gene in the XS52 DC line, but not in other cell types. The 5'-flanking and 3'-flanking sequences will, therefore, be used to target gene expression to DC in the genetic vaccines and gene therapies.

Similarly, a DNA segment comprising an isolated or purified dectin-1 or dectin-2 gene refers to a DNA segment including dectin-1 and/or dectin-2 coding sequences and, in certain aspects, regulatory sequences, isolated substantially away from other naturally occurring genes or protein encoding sequences. In this respect, the term "gene" is used for simplicity to refer to a DNA segment that encodes a polypeptide or a functional protein. As will be understood by those in the art, this functional term includes both genomic sequences, cDNA sequences and smaller engineered gene segments that express, or may be adapted to express, proteins, polypeptides or peptides.

"Isolated substantially away from other coding sequences" means that the gene of interest, in this case dectin-1 or dectin-2, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode a dectin-1 protein or polypeptide that includes within its amino acid sequence an amino acid sequence in accordance with SEQ ID NO:2, corresponding to human or mammalian dectin-1. In other embodiments, the invention concerns isolated DNA segments and recombinant vectors incorporating DNA sequences that encode a dectin-2 protein or polypeptide that includes within its amino acid sequence an amino acid sequence in accordance with SEQ ID NO:4, corresponding to human or mammalian dectin-2.

In certain embodiments, the invention concerns isolated DNA segments and recombinant vectors that encode a protein or polypeptide that includes within its amino acid sequence an amino acid sequence essentially as set forth in SEQ ID NO:2 and/or SEQ ID NO:4. Naturally, where the DNA segment or vector encodes a full length dectin-1 or dectin-2 protein, or is intended for use in expressing the dectin-1 or dectin-2 protein, the most preferred sequences are those that are essentially as set forth in SEQ ID NO: 2 and SEQ ID NO:4, respectively, and that encode proteins that retain T cell binding activity, e.g., as may be determined by any suitable assay, as disclosed herein. However, it is also contemplated that, where the DNA segment or vector encodes a mutated, truncated, or elongated form of the dectin-1 or dectin-2 proteins described herein, or is intended for use in expressing the mutated, truncated or elongated forms of the dectin-1 or dectin-2 proteins described herein, the most preferred sequences are those that are essentially as set forth in SEQ ID NO:13, SEQ ID NO:14, SEQ ID NO:15, SEQ ID NO:16 and SEQ ID NO:17.

The term "a sequence essentially as set forth in SEQ ID NO:2" means that the sequence substantially corresponds to a portion of SEQ ID NO:2 and has relatively few amino acids that are not identical to, or a biologically functional equivalent of, the amino acids of SEQ ID NO: 2. The term "biologically functional equivalent" is well understood in the art and is further defined in detail herein, for example see pages 72 through 77. Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:2 will be sequences that are "essentially as set forth in SEQ ID NO:2."

In certain other embodiments, the invention concerns isolated DNA segments and recombinant vectors that include within their sequence a nucleic acid sequence essentially as set forth in SEQ ID NO: 1 and/or SEQ ID NO:3. The term "essentially as set forth in SEQ ID NO:1" is used in the same sense as described above and means that the nucleic acid sequence substantially corresponds to a portion of SEQ ID NO:1 and has relatively few codons that are not identical, or functionally equivalent, to the codons of SEQ ID NO:1.

Again, DNA segments that encode proteins exhibiting T cell binding activity will be most preferred. The term "functionally equivalent codon" is used herein to refer to codons that encode the same amino acid, such as the six codons for arginine or serine, and also refers to codons that encode biologically equivalent amino acids. Table 1 sets forth the amino acids and codons which encode each amino acid.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It is within the scope of the invention in certain aspects that high level protein production may be achieved by reducing criteria for T cell binding activity. In certain embodiments it is within the invention to produce proteins lacking activity. Such proteins might be useful in very high volume to raise antibodies to the protein. In other aspects, activity is desired and the detailed examples explain preferred methods for obtaining proteins and/or polypeptides retaining T cell binding activity.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of T cell binding activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have between about 65% and about 80%; or more preferably, between about 80% and about 90%; or even more preferably, between about 90% and about 99% of nucleotides that are identical to the nucleotides of SEQ ID NO:1 will be sequences that are "essentially as set forth in SEQ ID NO:1". Sequences that are essentially the same as those set forth in SEQ ID NO:1 may also be functionally defined as sequences that are capable of hybridizing to a nucleic acid segment containing the complement of SEQ ID NO:1 under relatively stringent conditions. Suitable relatively stringent hybridization conditions will be well known to those of skill in the art and are clearly set forth herein, for example see pages 34–36 which describe conditions such as relatively low salt and/or high temperature conditions, such as provided by 0.02M–0.15M NaCl at temperatures of 50° C. to 70° C., for applications requiring high selectivity. Such relatively stringent conditions tolerate little, if any, mismatch between the probe and the template or target strand, and would be particularly suitable for isolating dectin-1 or dectin-2 genes.

For example, the expression of dectin-1 mRNA and dectin-2 mRNA in mouse tissues (e.g., spleen and thymus) and cell lines (e.g., XS52 DC line) was readily detectable with full-length cDNA probes (i.e., SEQ ID NO:1 for dectin-1 and SEQ ID NO:3 for dectin-2) in northern blotting under a high stringent condition, 0.12 M NaCl at 65° C. Likewise, dectin-1 mRNA and dectin-2 mRNA were both detectable by RT-PCR™, under an equally stringent condition (Tm=–15° C.) in mouse tissues (e.g., spleen and skin) and in mouse Langerhans cells freshly isolated from skin. These results indicate that mouse dectin-1 and dectin-2 mRNA are detectable with nucleotide sequences, either as cDNA probes or primers, that are identical to or contain the nucleotides of SEQ ID NO:1 or SEQ ID NO:3. On the other hand, identification of other members of the dectin family required a lower stringency. When cDNA prepared from human peripheral blood DC were hybridized with a CRD sequence of murine dectin-1 (SEQ ID NO:9), the inventors detected strong hybridization in Southern blotting only under a relatively low stringent condition (1M NaCl, 30–45% formamide, 10% dextran sulfate, at 37° C.). These results indicate that murine dectin-1 and human dectin-1 show a nucleotide sequence homology that is high enough to be detectable with the nucleotide sequence of SEQ ID NO:1. It is expected that a human equivalent for mouse dectin-1 can also be identified in a similar manner using the nucleotide sequence of SEQ ID NO:1. In fact, a 172 bp DNA fragment of human equivalent dectin-1 has been isolated and, as expected, shows a similarity with mouse dectin-1 of about 71.5% (SEQ ID NO:33). This supports the inventors' belief that the nucleotide sequence of SEQ ID NO:3 is useful for isolating and identifying a human equivalent for mouse dectin-2. Moreover, the same methods are applicable to identify dectin-1 and dectin-2 equivalents in other species as well.

Naturally, the present invention also encompasses DNA segments that are complementary, or essentially complementary, to the sequences set forth in SEQ ID NO:1 and SEQ ID NO:3. Nucleic acid sequences that are "complementary" are those that are capable of base-pairing according to the standard Watson-Crick complementary rules. That is, that the larger purines will always base pair with the smaller pyrimidines to form only combinations of Guanine paired with Cytosine (G:C) and Adenine paired with either Thymine (A:T), in the case of DNA, or Adenine paired with Uracil (A:U) in the case of RNA.

As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 or SEQ ID NO:3 under relatively stringent conditions such as those described herein. As such, these complementary sequences are substantially complementary over their entire length and have very few base mismatches. For example, nucleic acid sequences of six bases in length may be termed complementary when they hybridize at five out of six positions with only a single mismatch. Naturally, nucleic acid sequences which are "completely complementary" will be nucleic acid sequences which are entirely complementary throughout their entire length and have no base mismatches. Equivalents will show preferential binding to T cells. This is one feature which will distinguish it from non-dectin-1 or non-dectin-2 nucleic acid sequences.

Antisense constructs are oligo- or polynucleotides comprising complementary nucleotides to the coding segment of a DNA molecule, such as a gene or cDNA, including both the exons, introns and exon:intron boundaries of a gene. Antisense molecules are designed to inhibit the transcription, translation or both, of a given gene or construct, such that the levels of the resultant protein product are reduced or diminished. Antisense RNA constructs, or DNA encoding such antisense RNAs, may be employed to inhibit gene transcription or translation or both within a host cell, either in vitro or in vivo, such as within a host animal, including a human subject.

2. Hybridization Probes

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. In addition to their use in directing the expression of the dectin-1 or dectin-2 protein, the nucleic acid sequences disclosed herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous sequence of SEQ ID NO:1, and/or SEQ ID NO:3 will find particular utility. Longer contiguous identical or complementary sequences, e.g., those of about 20, 30, 40, 50, 100, 200, 500, 1000 nucleotides (including all intermediate lengths), and even up to full length sequences of about 2.4 kb (for dectin-1) and 1.2 kb (for dectin-2) will also be of use in certain embodiments.

It will be readily understood that "intermediate lengths", in this context, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002 and the like.

The ability of such nucleic acid probes to specifically hybridize to dectin-1 or dectin-2 encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10, 20, 30, 50, or even of 100–200 nucleotides or so, identical or complementary to SEQ ID NO:1, and/or SEQ ID NO:3 are particularly contemplated as hybridization probes for use in, e.g., Southern and northern blotting. This would allow dectin-1 or dectin-2 structural or regulatory genes to be analyzed, both in tissues and cells. In fact, the inventors have detected mRNA for both dectin-1 and dectin-2 in spleen and thymus in mice and in XS52 DC line. The inventors have also identified by southern blotting a human equivalent (2.8 kb) of dectin-2 using a cDNA probe for mouse dectin-2 CRD sequence (SEQ ID NO:9) under a low stringency condition. Moreover, a 172 bp cDNA probe for human dectin-2 (SEQ ID NO:33) hybridized in northern blotting 2.8 and 4.0 kb band in mRNA isolated from human peripheral blood mononuclear cells. Both bands were also detected in mRNA from human spleen, thymus, lymph nodes, and bone marrow, and appendix. By contrast, no significant hybridization was detected in mRNA isolated from non-lymphoid tissues in human, including heart, brain, lung, liver, muscle, kidney, and pancreas. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 10 and about 100 nucleotides, but larger contiguous complementary stretches of up to about 2.4 kb (for dectin-1) or 1.2 kb (for dectin-2) may be used, according to the length complementary sequences one wishes to detect.

The use of a hybridization probe of about 10–14 nucleotides in length allows the formation of a duplex molecule that is both stable and selective. Molecules having contiguous complementary sequences over stretches greater than 10 bases in length are generally preferred, though, in order to increase stability and selectivity of the hybrid, and thereby improve the quality and degree of specific hybrid molecules obtained, one will generally prefer to design nucleic acid molecules having gene-complementary stretches of 15 to 20 contiguous nucleotides, or even longer where desired.

Hybridization probes may be selected from any portion of any of the sequences disclosed herein. All that is required is to review the sequence set forth in SEQ ID NO:1 or SEQ ID NO:3 and to select any continuous portion of the sequence, from about 10 nucleotides in length up to and including the full length sequence, that one wishes to utilize as a probe or primer. The choice of probe and primer sequences may be governed by various factors, such as, by way of example only, one may wish to employ primers from towards the termini of the total sequence, or from the ends of the functional domain-encoding sequences, in order to amplify further DNA; one may employ probes corresponding to the entire DNA, or to the extracellular region, or to the CRD sequence to clone dectin-1-type or dectin-2-type genes from other species or to clone further dectin-1-like or dectin-2-like or homologous genes from any species including human; and one may employ wild-type and mutant probes or primers with sequences centered around the extracellular domain or CRD sequence to screen DNA samples for dectin-1 or dectin-2. Moreover, one may employ probes or primers with sequences centered around the different dectin-1 and dectin-2 isoforms.

The process of selecting and preparing a nucleic acid segment that includes a contiguous sequence from within SEQ ID NO:1 or SEQ ID NO:3 may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 and U.S. Pat. No. 4,682,195 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of dectin-1 or dectin-2 genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating dectin-1 or dectin-2 genes.

Of course, for some applications, for example, where one desires to prepare mutants employing a mutant primer strand hybridized to an underlying template or where one seeks to isolate dectin-1 or dectin-2 encoding sequences from related species, functional equivalents, or the like, less stringent hybridization conditions will typically be needed in order to allow formation of the heteroduplex. In these circumstances, one may desire to employ conditions such as 0.15M–1.0M salt, at temperatures ranging from 20° C. to 55° C. Cross-hybridizing species can thereby be readily identified as positively hybridizing signals with respect to control hybridizations. In fact, the inventors have been able to detect a human equivalent for mouse dectin-1 (of about 2.8 kb) by Southern hybridization of human DC cDNA with a CRD sequence of mouse dectin-1 (SEQ ID NO:9) under a low stringency condition (1M NaCl, 30–45% formamide, 10% dextran sulfate, at 37° C.). In any case, it is generally appreciated that conditions can be rendered more stringent by decreasing NaCl concentrations or by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

It will also be understood that this invention is not limited to the particular nucleic acid and amino acid sequences of SEQ ID NOS:1, 2, 3 and 4. Recombinant vectors and isolated DNA segments may therefore variously include the dectin-1 or dectin-2 coding regions themselves, coding regions bearing selected alterations or modifications in the basic coding region, or they may encode larger polypeptides that nevertheless include dectin-1 or dectin-2 coding regions or may encode biologically functional equivalent proteins or polypeptides that have variant amino acids sequences.

The DNA segments of the present invention encompass biologically functional equivalent dectin-1 or dectin-2 proteins and polypeptides. Such sequences may arise as a consequence of codon redundancy and functional equivalency that are known to occur naturally within nucleic acid sequences and the proteins thus encoded. Alternatively, functionally equivalent proteins or polypeptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test dectin-1 or dectin-2 mutants in order to examine T cell binding activity at the molecular level.

If desired, one may also prepare fusion proteins and polypeptides, e.g., where the dectin-1 or dectin-2 coding regions are aligned within the same expression unit with other proteins or polypeptides having desired functions, such as for purification or immunodetection purposes (e.g., proteins that may be purified by affinity chromatography or identified by enzyme label coding regions, respectively).

3. Recombinant Vectors and Protein Expression

Recombinant vectors form important further aspects of the present invention. Particularly useful vectors are contemplated to be those vectors in which the coding portion of the DNA segment, whether encoding a full length protein or smaller polypeptide, is positioned under the control of a promoter. The promoter may be in the form of the promoter that is naturally associated with a dectin-1 or dectin-2 gene(s), e.g., in DC, as may be obtained by isolating the 5' non-coding sequences located upstream of the coding segment or exon, for example, using recombinant cloning and/or PCR™ technology, in connection with the compositions disclosed herein (PCR™ technology is disclosed in U.S. Pat. No. 4,683,202 and U.S. Pat. No. 4,682,195, each incorporated herein by reference). In this regard, the inventors have isolated a genomic DNA fragment (about 3.2 kb) from the 5'-flanking regions of the dectin-2 (SEQ ID NO:34). This fragment, indeed, contains a putative promoter region, as indicated by its capacity to drive the transcription of the luciferase gene in a DC-specific manner.

a. Promoters and Enhancers

The promoters and enhancers that control the transcription of protein encoding genes in mammalian cells are composed of multiple genetic elements. The cellular machinery is able to gather and integrate the regulatory information conveyed by each element, allowing different genes to evolve distinct, often complex patterns of transcriptional regulation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator proteins. At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either cooperatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation.

Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities. They have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

Provided in Tables 2 and 3 are lists of viral promoters, cellular promoters/enhancers and inducible promoters/enhancers that could be used in combination with the present invention. Additionally any promoter/enhancer combination (as per the Eukaryotic Promoter Data Base EPDB) could also be used to drive expression of dectin-1 or dectin-2 or antisense constructs.

TABLE 2

REPRESENTATIVE PROMOTERS

| PROMOTERS | REFERENCES |
| --- | --- |
| Immunoglobulin Heavy Chain | Hanerji et al., 1983; Gilles et al., 1983; Grosschedl and Baltimore, 1985; Atchinson and Perry, 1986, 1987; Imler et al., 1987; Weinberger et al., 1988; Kiledjian et al., 1988; Porton et al., 1990 |
| Immunoglobulin Light Chain | Queen and Baltimore, 1983; Picard and Schaffner, 1984 |
| T-Cell Receptor | Luria et al., 1987, Winoto and Baltimore, 1989; -Redondo et al., 1990 |
| HLA DQ a and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987, Tronche et al., 1989, 1990 |
| a-Fetoprotein | Godbout et al., 1988; Campere and Tilghman, 1989 |
| t-Globin | Bodine and Ley, 1987; Perez-Stable and Constantini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| a$_1$-Antitrypain | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; -Dandolo et al., 1983; deVilliers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a, b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987, Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency Virus | Muesing et al., 1987; Hauber and Cullan, 1988; Jakobovits et al., 1988; Feng and Holland, 1988; Takebe et al., 1988; Rowen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and |

TABLE 2-continued

REPRESENTATIVE PROMOTERS

| PROMOTERS | REFERENCES |
|---|---|
| Gibbon Ape Leukemia Virus | Hofstetter, 1986<br>Holbrook et al., 1987; Quinn et al., 1989 |

TABLE 3

ENHANCERS AND INDUCERS

| | Inducer | References |
|---|---|---|
| MT II | Phorbol Ester (TFA)<br>Heavy metals | Palmiter et al., 1982; Haslinger and Karin, 1985; Searle et al., 1985; Stuart et al., 1985; Imagawa et al., 1987; Karin ®, 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Fonta et al., 1985; Sakai et al., 1986 |
| β-Interferon | poly(rI) × poly (rc) | Tavernier et al., 1983 |
| Adenovirus 5 E2 | Ela | Imperiale and Nevins, 1984 |
| Collagenase | Phorbol Ester (TPA) | Angle et al., 1987a |
| Stromelysin | Phorbol Ester (TPA) | Angle et al., 1987b |
| SV40 | Phorbol Ester (TFA) | Angel et al., 1987b |
| Murine MX Gene | Interferon, Newcastle Disease Virus | |
| GRP78 Gene | A23187 | Resendez et al., 1988 |
| a-2-Macroglobulin | IL-6 | Kunz et al., 1989 |
| Vimentin | Serum | Rittling et al., 1989 |
| MHC Class I Gene H-2kb | Interferon | Blanar et al., 1989 |
| HSP70 | Ela, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | FMA | Hensel et al., 1989 |
| Thyroid Stimulating Hormone a Gene | Thyroid Hormone | Chatterjee et al., 1989 |

It is understood in the art that to bring a coding sequence under the control of a promoter, one positions the 5' end of the transcription initiation site of the transcriptional reading frame of the protein between about 1 and about 50 nucleotides "downstream" of (i.e., 3' of) the chosen promoter. In addition, where eukaryotic expression is contemplated, one will also typically desire to incorporate into the transcriptional unit which includes the cotransporter protein, an appropriate polyadenylation site (e.g., 5'AATAAA-3') if one was not contained within the original cloned segment. Typically, the poly A addition site is placed about 30 to 2000 nucleotides "downstream" of the termination site of the protein at a position prior to transcription termination.

There are two basic procedures for studying the in vivo expression of cloned genes and their promoters. In transient systems, the gene of interest is introduced into a population of cultured cells, and its activity is assayed within a few hours to a few days. The original transient expression studies utilized encapsidated SV40 recombinants. Although only a small fraction of the cells take up and express the recombinant genes, transcription of the foreign gene can be readily detected. Alternatively, if the promoter (control region) of the recombinant gene is under study, the promoter and enhancer can be cloned with the coding region of a gene such as Herpes Simplex thymidine kinase (tk), E. coli chloramphenicol acetyltransferase (CAT), or luciferase (Luc). The activity of the promoter can be monitored by an assay for the presence of the appropriate gene product.

The second method for studying cloned genes and their control regions is stable transfection. Stable transfection is the preferred method for obtaining moderate expression levels from a transfected gene in a long term continuous culture. In this method the recombinant DNA molecule is introduced by DNA-mediated gene transfer techniques via viral infection. Identification of the recombinant stable transfectant among the population of untransformed cells requires a change in phenotype. Usually the inclusion of a drug selection marker aids in the discovery and selection of the stable transformants. Plasmids that are suitable for subcloning an expression cassette containing the target sequence and any of the promoter/enhancer combinations listed are well known to those of skill in the art. Such plasmids containing the target sequence and promoter/enhancer can be used in a stable transfection protocol or transient transfection procedure.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a dectin-1 or dectin-2 gene in its natural environment. Such promoters may include CMV, SV40, RSV, LacZ, LTR, TK, POLH, and MMTV or other promoters normally associated with other genes, and/or promoters isolated from any other bacterial, viral, eukaryotic, or mammalian cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. (1989). The promoters employed may be constitutive, or inducible, and can be used under the appropriate conditions to direct high level expression of the introduced DNA segment, such as is advantageous in the large-scale production of recombinant proteins or polypeptides. Appropriate promoter systems contemplated for use in high-level expression include, but are not limited to, CMV and SV40.

b. Expression Vectors

As mentioned above, in connection with expression embodiments to prepare recombinant dectin-1 or dectin-2 proteins and polypeptides, it is contemplated that longer DNA segments will most often be used, with DNA segments encoding the entire dectin-1 or dectin-2 protein or their extracellular domains, respectively, being most preferred. However, it will be appreciated that the use of shorter DNA segments to direct the expression of dectin-1 or dectin-2 polypeptides or epitopic core regions, such as may be used to generate anti-dectin-1 or anti-dectin-2 antibodies, also falls within the scope of the invention.

DNA segments that encode polypeptide antigens from about 15 to about 50 amino acids in length, or more preferably, from about 15 to about 30 amino acids in length are contemplated to be particularly useful. The polypeptides may, of course, be of any length in this range, such as 16, 17, 18, 19 or 20 amino acids in length. This is the meaning of "about" in about 15, about 20, about 25, about 30, about 35, about 40, about 45 or about 50 amino acids in length, with "about", in this one context meaning a range of from 1 to 4 amino acids longer or shorter than the stated length, with 14 or 15 or so still being the minimum length. DNA segments encoding polypeptides will generally have a minimum coding length in the order of about 45 to about 150, or to about 90 nucleotides. DNA segments encoding full length proteins may have a minimum coding length in the order of about 648 nucleotides for a protein in accordance with SEQ ID NO:2, or about 630 nucleotides for a protein in accordance with SEQ ID NO:4.

Turning to the expression of the dectin-1 or dectin-2 protein or polypeptides of the invention, once a suitable (full length if desired) clone or clones have been obtained, whether they be cDNA based or genomic, one may proceed to prepare an expression system for the recombinant preparation of dectin-1 or dectin-2. The engineering of DNA segment(s) for expression in a prokaryotic or eukaryotic system may be performed by techniques generally known to those of skill in recombinant expression. It is believed that virtually any expression system may be employed in the expression of dectin-1 or dectin-2.

It is proposed that transformation of host cells with DNA segments encoding the dectin-1 or dectin-2 protein will provide a convenient means for obtaining active dectin-1 or dectin-2. However, separate expression followed by reconstitution is also certainly within the scope of the invention.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

In addition, it is possible to express partial sequences, e.g., for the generation of antibodies against discrete portions of a gene product, even when the entire sequence of that gene product remains unknown. As noted herein, computer programs are available to aid in the selection of regions which have potential immunologic significance. For example, software capable of carrying out this analysis is readily available commercially, for example MacVector (IBI, New Haven, Conn.). The software typically uses standard algorithms such as the Kyte/Doolittle or Hopp/Woods methods for locating hydrophilic sequences which are characteristically found on the surface of proteins and are, therefore, likely to act as antigenic determinants.

In the recombinant production of large amounts of proteins or polypeptides, it may be advisable to analyze the protein to detect putative transmembrane sequences. Such sequences are typically very hydrophobic and are readily detected by the use of standard sequence analysis software, such as MacVector (IBI, New Haven, Conn.). The presence of transmembrane sequences is often deleterious when a recombinant protein is synthesized in many expression systems, especially E. coli, as it leads to the production of insoluble aggregates that are difficult to renature into the native conformation of the protein. Deletion of transmembrane sequences typically does not significantly alter the conformation of the remaining protein structure.

Moreover, transmembrane sequences, being by definition embedded within a membrane, are inaccessible. Antibodies to these sequences will not, therefore, generally prove useful in in vivo or in situ studies. Deletion of transmembrane-encoding sequences from the genes used for expression can be achieved by standard techniques. For example, fortuitously-placed restriction enzyme sites can be used to excise the desired gene fragment, or PCR™-type amplification can be used to amplify only the desired part of the gene.

The inventors have discovered that the transmembrane sequence of the dectin-1 protein of the present invention comprises the amino acid sequence from about position 45 to about position 68 of the full length dectin-1 protein. Similarly, the transmembrane sequence of the dectin-2 protein of the present invention comprises the amino acid sequence from about position 14 to about position 42 of the full length dectin-2 protein. Additionally, deletion of this sequence has been shown not to affect the T cell binding ability of the proteins. Thus, it is contemplated that the expressed proteins of the invention may lack these transmembrane sequences and yet retain their activity.

As used herein, the terms "engineered" and "recombinant" cells are intended to refer to a cell into which an exogenous DNA segment or gene, such as a cDNA or gene encoding a dectin-1 or dectin-2 protein or polypeptide has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant dectin-1 or dectin-2 protein or polypeptide, whether mutant or wild-type, in accordance with the present invention one would prepare an expression vector that comprises a dectin-1 or dectin-2 protein or polypeptide-encoding nucleic acid segment under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or polypeptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium*, *Serratia marcescens*, and various *Pseudomonas* species.

In general, plasmid vectors containing replicon and control sequences which are derived from species compatible with the host cell are used in connection with these hosts. The vector ordinarily carries a replication origin, as well as marking sequences which are capable of providing phenotypic selection in transformed cells. For example, *E. coli* is often transformed using pBR322, a plasmid derived from an *E. coli* species. pBR322 contains genes for ampicillin and tetracycline resistance and thus provides EASY means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, mannose binding protein (MBP) and the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

The following details concerning recombinant protein production in bacterial cells, such as *E. coli*, are obtained from exemplary information on recombinant protein production in general, the adaptation of which to a particular recombinant expression system will be known to those of skill in the art.

Bacterial cells, for example, *E. coli*, containing the expression vector are grown in any of a number of suitable media, for example, LB. The expression of the recombinant protein may be induced, e.g., by adding IPTG to the media or by switching incubation to a higher temperature. After culturing the bacteria for a further period, generally of between 2 and 24 hours, the cells are collected by centrifugation and washed to remove residual media.

The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents, such as β-mercaptoethanol or DTT (dithiothreitol).

Under some circumstances, it may be advantageous to incubate the protein for several hours under conditions suitable for the protein to undergo a refolding process into a conformation which more closely resembles that of the native protein. Such conditions generally include low protein concentrations, less than 500 μg/ml, low levels of reducing agent, concentrations of urea less than 2 M and often the presence of reagents such as a mixture of reduced and oxidized glutathione which facilitate the interchange of disulfide bonds within the protein molecule.

The refolding process can be monitored, for example, by SDS-PAGE, or with antibodies specific for the native molecule (which can be obtained from animals immunized with the native molecule or smaller quantities of recombinant protein). Following refolding, the protein can then be purified further and separated from the refolding mixture by chromatography on any of several supports including ion exchange resins, gel permeation resins or on a variety of affinity columns.

In addition to prokaryotes, eukaryotic microbes, such as yeast cultures, may also be used. *Saccharomyces cerevisiae*, or common baker's yeast, is the most commonly used among eukaryotic microorganisms, although a number of other strains are commonly available. For expression in *Saccharomyces*, the plasmid YRp7, for example, is commonly used (Stinchcomb et al., 1979; Kingsman et al., 1979; Tschemper et al., 1980). This plasmid already contains the trp1 gene which provides a selection marker for a mutant strain of yeast lacking the ability to grow in tryptophan, for example ATCC No. 44076 or PEP4-1 (Jones, 1977). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more dectin-1 or dectin-2 protein or polypeptide coding sequences.

In a useful insect system, *Autograph californica* nuclear polyhidrosis virus (AcNPV) is used as a vector to express foreign genes. The virus grows in *Spodoptera frugiperda* cells. The dectin-1 or dectin-2 protein or polypeptide coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051 (Smith)).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein.

Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for glycosylation, intracellular transport, high expression and DNA replication may be used if desired, with a cell that allows for high expression being preferred.

Expression vectors for use in mammalian such cells ordinarily include an origin of replication (as necessary), a promoter located in front of the gene to be expressed, along with any necessary ribosome binding sites, RNA splice sites, polyadenylation site, and transcriptional terminator sequences. The origin of replication may be obtained from either construction of the vector to include an exogenous origin, such as may be derived from SV40 or other viral (e.g., Polyoma, Adeno, VSV, BPV) source, or may be obtained from the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired dectin-1 or dectin-2 gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication. Further, it is also possible and often desirable to utilize promoter or control sequences normally associated with the desired gene sequence, provided such control sequences are compatible with the host cell systems.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing dectin-1 or dectin-2 proteins in infected hosts.

Specific initiation signals may also be required for efficient translation of dectin-1 or dectin-2 coding sequences. These signals include the ATG initiation codon and adjacent Kosak sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators (Bittner et al., 1987).

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination codon of the protein at a position prior to transcription termination.

For long-term, high-yield production of recombinant dectin-1 or dectin-2 proteins, stable expression is preferred. For example, cell lines that stably express constructs encoding dectin-1 or dectin-2 proteins or polypeptides may be engineered. Rather than using expression vectors that contain viral origins of replication, host cells can be transformed with vectors controlled by appropriate expression control elements (e.g., promoter, enhancer, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus thymidine kinase (Wigler et al., 1977), hypoxanthine-guanine phosphoribosyltransferase (Szybalska et al., 1962) and adenine phosphoribosyltransferase genes (Lowry et al., 1980), in tk-, hgprt- or aprt cells, respectively. Also, antimetabolite resistance can be used as the basis of selection for dhfr, that confers resistance to methotrexate (Wigler et al., 1980; O'Hare et al., 1981); gpt, that confers resistance to mycophenolic acid (Mulligan et al., 1981); neo, that confers resistance to the aminoglycoside G-418 (Colberre-Garapin et al., 1981); and hygro, that confers resistance to hygromycin (Santerre et al., 1984).

It is contemplated that the dectin-1 or dectin-2 of the invention may be "overexpressed", i.e., expressed in increased levels relative to its natural expression in dendritic cells, or even relative to the expression of other proteins in the recombinant host cell. Such overexpression may be assessed by a variety of methods, including radio-labeling and/or protein purification. However, direct methods are preferred, for example, those involving SDS/PAGE and protein staining or western blotting, followed by quantitative analyses, such as densitometric scanning of the resultant gel or blot. A specific increase in the level of the recombinant protein or polypeptide in comparison to the level in natural DC is indicative of overexpression, as is a relative abundance of the specific protein in relation to the other proteins produced by the host cell and, e.g., visible on a gel.

Also contemplated as within the scope of the invention are animals which have been engineered to overexpress the dectin-1 and/or dectin-2 proteins or polypeptides described herein. For example, animals expressing transgenes for dectin-1 and/or dectin-2 are within the scope of the invention. Such transgenes may be of mouse origin, or may be from other species such as human. Expression of transgenes may be targeted to selected tissues and cell types by the use of different promoters. For example, one may use immunoglobulin promoter to target the expression to B cells, T cell receptor promoter to T cells, and keratin promoter to keratinocytes. It is further contemplated that such transgenes may be incorporated at the levels of eggs as well as animals. Additionally, altered expression may occur at the levels of DNA, RNA, proteins and/or functions.

As indicated above, the present invention relates to the use of cells as cellular vehicles for gene transfer, in particular, for the overexpression of dectin-1 or dectin-2 in animals. Preferably, the cells are DC.

In one embodiment, the invention is directed to a method of causing overexpression of dectin-1 or dectin-2 in animals, comprising: (i) inserting into the cells a DNA (RNA) segment encoding dectin-1 or dectin-2; and (ii) introducing cells resulting from step (i) into the animal. The gene can be inserted into the cells using any gene transfer procedure, for example, retroviral-mediated gene transfer, electroporation, calcium phosphate mediated transfection, microinjection or proteoliposomes. Other vectors can be used besides retroviral vectors, including those derived from DNA viruses and other RNA viruses. As should be apparent when using an RNA virus, such virus includes RNA which encodes dectin-1 or dectin-2, with the cells which are genetically engineered with such RNA virus thus being provided with DNA encoding the dectin-1 or dectin-2.

More specifically, there is provided a method of enhancing the expression of dectin-1 or dectin-2 in cells that are infused in an animal, comprising (i) inserting into the cells of an animal a DNA (RNA) segment encoding dectin-1 or dectin-2; and (ii) introducing cells resulting from step (i) into the animal under conditions such that the cells resulting from step (i) "target" to a tissue site.

Alternatively, DNA (RNA) may be inserted into the DC of an animal in vivo, by administering such DNA (RNA) in a vehicle which targets such DC.

The inventors also contemplate that animals in which expression of endogenous dectin-1 and/or dectin-2 are upregulated by exogenous stimuli, and animals expressing foreign genes under the control of promoter sequences of dectin-1 and/or dectin-2 are within the scope of the invention. In such animals expressing foreign genes under the control of promoter sequences of dectin-1 and/or dectin-2, gene expression may be targeted to DC or non-DC by the use of sequences in the 5'-flanking regions. It is contemplated that the foreign genes to be expressed may be of bacterial, yeast or mammalian origin. Moreover, the use of dectin-1 and/or dectin-2 promoter sequences to cause expression of foreign genes may provide an ideal method to deliver foreign genes in a DC-specific manner. This gene delivery system may be useful in "gene vaccine therapies" against infectious pathogens and tumor-associated antigens.

Also contemplated as being within the scope of the invention are cells engineered not to express dectin-1 and/or dectin-2 and animals engineered not to express dectin-1 and/or dectin-2. Cells may be engineered not to express dectin-1 and/or dectin-2 by anti-sense DNA or RNA or by exogenous stimuli. Such cells may be DC, as well as other cell types, including those isolated or cultured from gene knock-out animals, as well as animals and human patients with genetic mutations. Additionally, such cells may lack the expression of particular isoforms and/or may lack the expression at the levels of DNA, RNA, proteins and/or function.

Animals engineered not to express dectin-1 and/or dectin-2 may be produced by homologous recombination, as well as by anti-sense RNA or DNA insertion. It is contemplated that expression may be inhibited by exogenous stimuli and may be inhibited at the levels of DNA, RNA, proteins and/or functions.

Currently preferred methods for producing dectin-1 or dectin-2 proteins or polypeptides by recombinant expression are described herein. For example, Example 5 provides that dectin-1 or dectin-2 proteins or polypeptides may be obtained by recombinant expression in E. coli.

4. Molecular Heterogeneity of Dectin-1 or Dectin-2 mRNA

As described above, the inventors have determined the identities of truncated dectin-1 and dectin-2 mRNAs using methods similar to those developed and employed in previous studies. The truncated form of dectin-1, termed "Tβ isoform," (SEQ ID NO:13) was found to contain a 45 amino acid deletion in the connecting domain, compared with the full-length dectin-1 (Tα) (SEQ ID NO:2). The inventors have also identified, in addition to the full length dectin-2 (Tα) (SEQ ID NO:4), four isoforms: a) Tβ with a 65 amino acid deletion primarily in the transmembrane and connecting domains (SEQ ID NO:14); b) Tγ with a 34 amino acid deletion primarily in the connecting domain (SEQ ID NO:15); c) Tδ with a 41 amino acid deletion in the C-terminus of the CRD domain, in addition to the same 34 amino acid deletion seen in Tγ (SEQ ID NO:16); and d) Tε with a 43 amino acid deletion within the CRD domain (SEQ ID NO:17). These different isoforms of dectin-2 are produced by alternative splicing. More specifically, truncated dectin-2 mRNAs have been identified to contain total or partial deletion of one or two of the six exons in the dectin-2 gene. The inventors have also identified in western blotting multiple bands of dectin-1 or dectin-2, some of which may correspond to different protein isoforms.

As used herein, the terms dectin-1 and/or dectin-2 include not only the full length molecules but also the isoforms described above, glycosylated forms as well as non-glycosylated forms of the molecules, and other members of the dectin family.

5. 3'- and 5'-Flanking Regions of Dectin-1 or Dectin-2 Gene

The inventors have cloned and sequenced not only the cDNA for the coding sequences of dectin-1 and dectin-2, but also 5' untranslated region (5'UTR) and 3'UTR. Moreover, the inventors have also cloned and sequenced the genomic DNA for dectin-2 of about 13 kb in total size. The 5'-flanking and 3'-flanking sequences are of particular importance in terms of regulating DC-specific transcription of the dectin-1 or dectin-2 gene. In fact, the inventors have isolated a putative promoter fragment (about 3.2 kb) of the dectin-2 gene, a fragment that has been proven to drive transcription of the luciferase gene in the XS52 DC line, but not in other cell types. The 5'-flanking and 3'-flanking sequences will, therefore, be used to target gene expression to DC in the genetic vaccines and gene therapies.

Figure 5A:
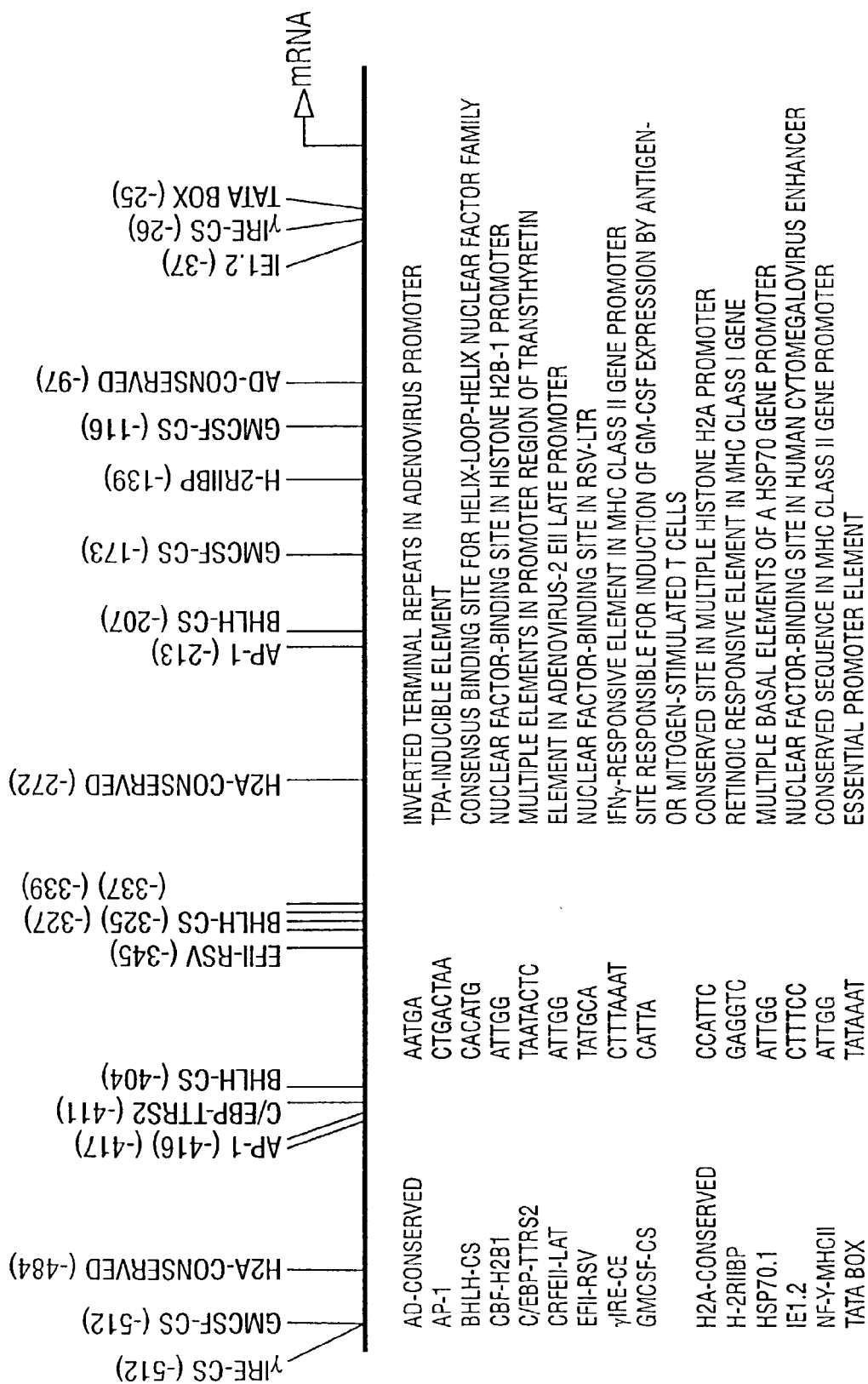
FIG. 5A, FIG. 5B and FIG. 5C. Transcriptional regulation of dectin-2 gene.

When employed in the context of heterologous structural genes, the precise location of the control sequences of the invention with respect to transcription initiation site is not particularly crucial. For example, some benefit will generally be obtained when such control sequences are located up to about 300 nucleotides or more from a transcription initiation site. However, in more preferred embodiments, control sequences are most advantageously employed when disposed within 50 nucleotides of transcription initiation. Thus, in general, the closer the control sequences are to transcript initiation, the more pronounced and effective the control obtained. The inventors have, in fact, identified the transcription initiation site for the dectin-2 gene at 220 bp upstream from the coding sequence (ATG) (see FIG. 5A).

Therefore, to employ the foregoing regulatory elements in the context of heterologous genes, one obtains the structural gene and locates one or more of such control sequences upstream of a transcription initiation site. Additionally, as is known in the art, it is generally desirable to include TATA-box sequences upstream of and proximal to a transcription initiation site of the heterologous structural gene. Such sequences may be synthesized and inserted in the same manner as the novel control sequences. Alternatively, one may desire to employ the TATA sequences normally associated with the heterologous gene. In any event, TATA sequences are most desirably located between about 20 and 30 nucleotides upstream of transcription initiation. The inventors have, in fact, identified a highly conserved TATA box sequence 31 bp upstream from the transcription initiation site (see FIG. 5A).

Numerous methods are known in the art for precisely locating selected sequences at selected points within larger sequences. Most conveniently, the desired control sequence or sequences, or combinations of sequences, are synthesized and restriction site linker fragments added to the control sequence termini. This allows for ready insertion of control sequences into compatible restriction sites within upstream regions. Alternatively, synthesized control sequences may be ligated directly to selected regions. Moreover, site specific mutagenesis may be employed to fashion restriction sites into which control sequences may be inserted in the case where no convenient restriction sites are found at a desired insertion site.

As noted, it is believed that the control sequences of the present invention may be beneficially employed in the context of any heterologous structural gene, with or without additional homologous or heterologous control or promotion sequences. The following table, Table 4, lists a number of known defined structural genes, along with descriptive references, which may be employed in the context of the control sequences of the present invention. It should, however, be appreciated that this table is in no way intended to be an exhaustive or all-inclusive listing, and it is included herein for the convenience of the reader. For a more extensive listing, one may wish to refer to Beaudet (1985).

TABLE 4

| Selected Cloned Structural Genes | | |
|---|---|---|
| Gene | Clone Type* | Reference |
| activin | porcine-cDNA | Mason, Nature, 318: 659, 1985. |
| adenosine deaminase | h-cDNA | Wiginton, Proc. Natl. Acad. Sci., 80: 7481, 1983. |
| angiotensinogen I | r-cDNA | Ohkubo, Proc. Natl. Acad. Sci., 80: 2196, 1983. |
| | r-gDNA | Tanaka, J. Biol. Chem., 259: 8063, 1984. |
| antithrombin III | h-cDNA | Bock, Nucleic Acids Research, 10: 8113, 1982. |
| | h-cDNA and gDNA | Prochownik, J. Biol. Chem., 258: 8389, 1983. |
| antitrypsin, αI | h-cDNA | Kurachi, Proc. Natl. Acad. Sci., 78: 6826, 1981. |
| | h-gDNA | Leicht, Nat, 297: 655, 1982. |
| | RFLP | Cox, Am. J. Hum. Gen., 36: 134S, 1984. |
| apolipoprotein A-I | h-cDNA, h-gDNA | Shoulders, Nucleic Acids Research, 10: 4873, 1982. |
| | RFLP | Karathanasis, Nature, 301: 718, 1983. |
| | h-gDNA | Karathanasis, Proc. Natl. Acad. Sci., 80: 6147, 1983. |

TABLE 4-continued

| | | |
|---|---|---|
| apolipoprotein A-II | h-cDNA | Sharpe, Nucleic Acids Research, 12: 3917, 1984. |
| | Chr | Sakaguchi, Am. J. Hum. Gen., 36: 207S, 1984. |
| | h-cDNA | Knott, Biochem. Biophys. Res. Comm., 120: 734, 1984. |
| apolipoprotein C-I | h-cDNA | Knott, Nucleic Acids Research, 12: 3909, 1984. |
| apolipoprotein C-II | h-cDNA | Jackson, Proc. Natl. Acad. Sci., 81: 2945, 1984. |
| | h-cDNA | Mykelbost, J. Biol. Chem., 259: 4401, 1984. |
| | h-cDNA | Fojo, Proc. Natl. Acad. Sci., 81: 6354, 1984. |
| | RFLP | Humphries, C Gen, 26: 389, 1984. |
| apolipoprotein C-III | h-cDNA and gDNA | Karanthanasis, Nature, 304: 371, 1983. |
| | h-cDNA | Sharpe, Nucleic Acids Research, 12: 3917, 1984. |
| apolipoprotein E | h-cDNA | Breslow, J. Biol. Chem., 257: 14639, 1982. |
| atrial natriuretic factor | h-cDNA | Oikawa, Nature, 309: 724, 1984. |
| | h-cDNA | Nakayama, Nature, 310: 699, 1984. |
| | h-cDNA | Zivin, Proc. Natl. Acad. Sci., 81: 6325, 1984. |
| | h-gDNA | Seidman, Science, 226: 1206, 1984. |
| | h-gDNA | Nemer, Nature, 312: 654, 1984. |
| | h-gDNA | Greenberg, Nature, 312: 656, 1984. |
| chorionic gonadotropin, α chain | h-cDNA | Fiddes, Nature, 281: 351, 1981. |
| | RFLP | Botheby, J. Biol. Chem., 256: 5121, 1981. |
| chorionic gonadotropin, β chain | h-cDNA | Fiddes, Nature, 286: 684, 1980. |
| | h-gDNA | Boorstein, Nature, 300: 419, 1982. |
| | h-gDNA | Talmadge, Nature, 307: 37, 1984 |
| chymosin, pro (rennin) | bovine-cDNA | Harris, Nucleic Acids Research, 10: 2177, 1982. |
| complement, factor B | h-cDNA | Woods, Proc. Natl. Acad. Sci., 79: 5661, 1982. |
| | h-cDNA and gDNA | Duncan, Proc. Natl. Acad. Sci., 80: 4464, 1983. |
| complement C2 | h-cDNA | Bentley, Proc. Natl. Acad. Sci., 81: 1212, 1984. |
| | h-gDNA (C2, C4, and B) | Carroll, Nature, 307: 237, 1984. |
| complement C3 | m-cDNA | Domdey, Proc. Natl. Acad. Sci., 79: 7619, 1983. |
| | h-gDNA | Whitehead, Proc. Natl. Acad. Sci., 79: 5021, 1982. |
| complement C4 | h-cDNA and gDNA | Carroll, Proc. Natl. Acad. Sci., 80: 264, 1983. |
| | h-cDNA | Whitehead, Proc. Natl. Acad. Sci., 80: 5387, 1983. |
| complement C9 | h-cDNA | DiScipio, Proc. Natl. Acad. Sci., 81: 7298, 1984. |
| corticotropin releasing factor | sheep-cDNA | Furutani, Nature, 301: 537, 1983. |
| | h-gDNA | Shibahara, EMBO J., 2: 775, 1983. |
| epidermal growth factor | m-cDNA | Gray, Nature, 303: 722, 1983. |
| | m-cDNA | Scott, Science, 221: 236, 1983. |
| | h-gDNA | Brissenden, Nature, 210: 781, 1984. |
| epidermal growth factor receptor, oncogene c-erb B | h-cDNA and Chr | Lan, Science, 224: 843, 1984. |
| epoxide dehydratase | r-cDNA | Gonzalez, J. Biol. Chem. 256: 4697, 1981. |
| erythropoietin | h-cDNA | Lee-Huang, Proc. Natl. Acad. Sci., 81: 2708, 1984. |
| esterase inhibitor, C1 | h-cDNA | Stanley, EMBO J., 3: 1429, 1984. |
| factor VIII | h-cDNA and gDNA | Gitschier, Nature, 312: 326, 1984. |
| | h-cDNA | Toole, Nature, 312: 342, 1984. |
| factor IX, Christmas factor | h-cDNA | Kutachi, Proc. Natl. Acad. Sci., 79: 6461, 1982. |
| | h-cDNA | Choo, Nature, 299: 178, 1982. |
| | RFLP | Camerino, Proc. Natl. Acad. Sci., 81: 498, 1984. |
| | h-gDNA | Anson, EMBO J., 3: 1053, 1984. |
| factor X | h-cDNA | Leytus, Proc. Natl. Acad. Sci., 81: 3699, 1984. |
| fibrinogen A α, B β, γ | h-cDNA | Kant, Proc. Natl. Acad. Sci., 80: 3953, 1983. |
| | h-gDNA (γ) | Fornace, Science, 224: 161, 1984. |

TABLE 4-continued

| | h-cDNA (α γ) | Imam, Nucleic Acids Research, 11: 7427, 1983. |
|---|---|---|
| | h-gDNA (γ) | Fornace, J. Biol. Chem., 259: 12826, 1984. |
| gatrin releasing peptide | h-cDNA | Spindel, Proc. Natl. Acad. Sci., 81: 5699, 1984. |
| glucagon, prepro | hamster-cDNA | Bell, Nature, 302: 716, 1983. |
| | h-gDNA | Bell, Nature, 304: 368, 1983. |
| growth hormone | h-cDNA | Martial, Science, 205: 602, 1979. |
| | h-gDNA | DeNoto, Nucleic Acids Research, 9: 3719, 1981. |
| | GH-like gene | Owerbach, Science, 209: 289, 1980. |
| growth hormone RF | h-cDNA | Gubler, Proc. Natl. Acad. Sci., 80: 4311, 1983. |
| somatocrinin | h-cDNA | Mayo, Nature, 306: 86, 1983. |
| hemopexin | h-cDNA | Stanley, EMBO J., 3: 1429, 1984. |
| inhibin | porcine-cDNA | Mason, Nature, 318: 659, 1985. |
| insulin, prepro | h-gDNA | Ullrich, Science, 209: 612, 1980. |
| insulin-like growth factor I | h-cDNA | Jansen, Nature, 306: 609, 1983. |
| | h-cDNA | Bell, Nature, 310: 775, 1984. |
| | Chr | Brissenden, Nature, 310: 781, 1984. |
| insulin-like growth factor II | h-cDNA | Bell, Nature, 310: 775, 1984. |
| | h-gDNA | Dull, Nature, 310: 777, 1984. |
| | Chr | Brissenden, Nature, 310: 781, 1984. |
| interferon, α | h-cDNA | Maeda, Proc. Natl. Acad. Sci., 77: 7010, 1980. |
| (leukocyte), multiple | h-cDNA (8 distinct) | Goeddel, Nature, 290: 20, 1981. |
| | h-gDNA | Lawn, Proc. Natl. Acad. Sci., 78: 5435, 1981. |
| | h-gDNA | Todokoro, EMBO J., 3: 1809, 1984. |
| | h-gDNA | Torczynski, Proc. Natl. Acad. Sci., 81: 6451, 1984. |
| interferon, β (fibroblast) | h-cDNA | Taniguchi, Gene, 10: 11, 1980. |
| | h-gDNA | Lawn, Nucleic Acids Research, 9: 1045, 1981. |
| | h-gDNA (related) | Sehgal, Proc. Natl. Acad. Sci., 80: 3632, 1983. |
| | h-gDNA (related) | Sagar, Science, 223: 1312, 1984. |
| interferon, γ (immune) | h-cDNA | Gray, Nature, 295: 503, 1982. |
| | h-gDNA | Gray, Nature, 298: 859, 1982. |
| interleukin-1 | m-cDNA | Lomedico, Nature, 312: 458, 1984. |
| interleukin-2, T-cell | h-cDNA | Devos, Nucleic Acids Research, 11: 4307, 1983. |
| growth factor | h-cDNA | Taniguchi, Nature, 302: 305, 1983. |
| growth factor (cont'd) | h-gDNA | Hollbrook, Proc. Natl. Acad. Sci., 81: 1634, 1984. |
| | Chr | Siegel, Science, 223: 175, 1984. |
| interleukin-3 | m-cDNA | Fung, Nature, 307: 233, 1984. |
| kininogen, two forms | bovine-cDNA | Nawa, Proc. Natl. Acad. Sci., 80: 90, 1983. |
| | bovine-cDNA and gDNA | Kitamura, Nature, 305: 545, 1983. |
| luteinizing hormone, β subunit | h-gDNA and Chr | Talmadge, Nature, 207: 37, 1984. |
| luteinizing hormone releasing hormone | h-cDNA and gDNA | Seeburg, Nature, 311: 666, 1984. |
| lymphotoxin | h-cDNA and gDNA | Gray, Nature, 312: 721, 1984. |
| mast cell growth factor | m-cDNA | Yokoya, Proc. Natl. Acad. Sci., 81: 1070, 1984. |
| nerve growth factor, β subunit | m-cDNA | Scott, Nature, 302: 538, 1983. |
| | h-gDNA | Ullrich, Nature, 303: 821, 1983. |
| | Chr | Franke, Science, 222: 1248, 1983. |
| oncogene, c-sis, PGDF chain A | h-gDNA | Dalla-Favera, Nature, 295: 31, 1981. |
| pancreatic polypeptide | h-cDNA | Clarke, Nature, 208: 464, 1984. |
| and icosapeptide | h-cDNA | Boel, EMBO J., 3: 909, 1984. |
| parathyroid hormone, prepro | h-cDNA | Hendy, Proc. Natl. Acad. Sci., 78: 7365, 1981. |
| | h-gDNA | Vasicek, Proc. Natl. Acad. Sci., 80: 2127, 1983. |
| plasminogen | h-cDNA and gDNA | Malinowski, Fed P., 42: 1761, 1983. |
| plasminogen activator | h-cDNA | Edlund, Proc. Natl. Acad. Sci., 80: 349, 1983. |
| | h-cDNA | Pennica, Nature, 301: 214, 1983. |
| | h-gDNA | Ny, Proc. Natl. Acad. Sci., 81: 5355, 1984. |
| prolactin | h-cDNA | Cook, J. Biol. Chem., 256: 4007, 1981. |
| | r-gDNA | Cooke, Nature, 297: 603, 1982. |
| proopiomelanocortin | h-cDNA | DeBold, Science, 220: 721, 1983. |

TABLE 4-continued

| | h-gDNA | Cochet, Nature, 297: 335, 1982. |
|---|---|---|
| protein C | h-cDNA | Foster, Proc. Natl. Acad. Sci., 81: 4766, 1984. |
| prothrombin | bovine-cDNA | MacGillivray, Proc. Natl. Acad. Sci., 77: 5153, 1980. |
| relaxin | h-gDNA | Hudson, Nature, 301: 628, 1983. |
| | h-cDNA (2 genes) | Hudson, EMBO J., 3: 2333, 1984. |
| | Chr | Crawford, EMBO J., 3: 2341, 1984. |
| renin, prepro | h-cDNA | Imai, Proc. Natl. Acad. Sci., 80: 7405, 1983. |
| | h-gDNA | Hobart, Proc. Natl. Acad. Sci., 81: 5026, 1984. |
| | h-gDNA | Miyazaki. Proc. Natl. Acad. Sci., 81: 5999, 1984. |
| | Chr | Chirgwin, SCMG, 10: 415, 1984. |
| somatostatin | h-cDNA | Shen, Proc. Natl. Acad. Sci., 79: 4575, 1982. |
| | h-gDNA and Ri-IP | Naylot, Proc. Natl. Acad. Sci., 80: 2686, 1983. |
| tachykinin, prepro | bovine-cDNA | Nawa, Nature, 306: 32, 1983. |
| substances P and K | bovine-gDNA | Nawa, Nature, 312: 729, 1984. |
| urokinase | h-cDNA | Verde, Proc. Natl. Acad. Sci., 81: 4727, 1984. |
| vasoactive intestinal peptide, prepro | h-cDNA | Schmale, EMBO J., 2: 763, 1983. |
| vasopressin | r-cDNA | Itoh, Nature, 304: 547, 1983. |

*cDNA complementary DNA
Chr chromosome
gDNA genomic DNA
RFLP restriction fragment polymorphism
h human
m mouse
r rat C. Dectin-1 or Dectin-2 Proteins or Polypeptides 1. Purification of Dectin-1 or Dectin-2 Proteins Further aspects of the present invention concern the purification, and in particular embodiments, the substantial purification, of a dectin-1 or dectin-2 protein or polypeptide. The term "purified protein" as used herein, is intended to refer to a dectin-1 or dectin-2 composition, isolatable from DC, XS52 cells, or recombinant host cells, wherein the dectin-1 or dectin-2 is purified to any degree relative to its naturally-obtainable state, i.e., in this case, relative to its purity within a DC or XS52 cell extract. A purified dectin-1 or dectin-2 protein therefore also refers to a protein, free from the environment in which it may naturally occur in intact cells.

It is contemplated that the purified dectin-1 or dectin-2 proteins or polypeptides of the invention will generally possess dectin-1 or dectin-2 activity. That is, they will have the capacity to bind to putative ligands expressed by T cells and modulate DC-T cell interaction during antigen presentation.

Generally, "purified" will refer to a dectin-1 or dectin-2 composition which has been subjected to fractionation to remove various non-dectin-1 or non-dectin-2 components such as other cell components. Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques. A specific example presented herein is the purification of dectin-1 using immunoprecipitation with anti-dectin-1 antibodies (BAD1-Pep). Briefly, whole extracts prepared from either the XS52 DC line or splenic DC of BALB/c mice were incubated with Protein A-sepharose beads that had been conjugated with rabbit anti-dectin-1. After extensive washing to remove unbound molecules, dectin-1 was eluted in SDS sample buffer. The resulting preparations were >70% pure, as assessed by SDS-PAGE and western blot analyses. Similar methods may be used to purify native dectin-2 proteins. Another example is the purification of His-tagged dectin-1 and His-tagged dectin-2 from recombinant host cells. The inventors have purified recombinant His-dectin-1 (extracellular domains) and His-dectin-2 (extracellular domains) from *E. coli* or from Sf-9 insect cells by nickel-affinity chromatography. The resulting preparations were >90% pure, as assessed by SDS-PAGE and western blotting.

Where the term "substantially purified" is used, this will refer to a composition in which dectin-1 or dectin-2 forms the major component of the composition, such as constituting about 50% of the proteins in the composition or more. In preferred embodiments, a substantially purified protein will constitute more than 60% of the proteins in the composition.

A polypeptide or protein that is "purified to homogeneity," as applied to the present invention, means that the polypeptide or protein has a level of purity where the polypeptide or protein is substantially free from other proteins and biological components. For example, a purified polypeptide or protein will often be sufficiently free of other protein components so that degradative sequencing may be performed successfully.

Various methods for quantifying the degree of purification of the dectin-1 or dectin-2 protein will be known to those of skill in the art in light of the present disclosure. These include, for example, determining the specific activity of an active fraction, or assessing the number of polypeptides within a fraction by gel electrophoresis. Assessing the number of polypeptides within a fraction by SDS/PAGE analysis will often be preferred in the context of the present invention, e.g., in assessing protein purity.

A preferred method for assessing the purity of a dectin-1 or dectin-2 fraction is to calculate the specific activity of the fraction, to compare it to the specific activity of the initial dendritic cell or XS52 extract, and to thus calculate the degree of purity, herein assessed by a "-fold purification number".

The actual units used to represent the amount of T cell binding activity will, of course, be dependent upon the particular assay technique chosen to follow the purification. As discussed above, the present inventors prefer to use SDS-PAGE and western blotting to examine the relative amounts of dectin-1 or dectin-2 proteins. For this purpose, it is preferred to use polyclonal antibodies against dectin-1 or dectin-2, antibodies that recognize several epitopes of these molecules. The inventors currently have rabbit polyclonal antibodies against synthetic polypeptide of dectin-1 (BAD1-Pep), rabbit and rat polyclonal antibodies against His-dectin-1 (BAD1-Rhi and TAD1-Rhi), rabbit and rat polyclonal antibodies against His-dectin-2 (BAD2-Rhi and TAD2-Rhi), and rat monoclonal antibodies against His-dectin-2 (MAD2-Rhi). In these assays, the test samples will be examined for protein concentration, separated by SDS-PAGE, and stained by coomassie blue. An additional SDS-PAGE gel that will be run in parallel will then be examined by western blotting with polyclonal antibodies to identify the putative band for dectin-1 or dectin-2. The amounts of dectin-1 or dectin-2 proteins will then be calculated by multiplying the total protein concentration with the relative purity that will be determined by densitometric analysis of the coomassie-stained SDS-PAGE gel. For example, if one fraction contains 1 mg/ml protein and contains dectin-1 70% purity, this fraction is calculated to contain 0.7 mg/ml dectin-1 protein. An advantage of this system will be that one can test simultaneously the protein profile of dectin-1 or dectin-2, so that one can eliminate contamination problems of degraded dectin-1 or dectin-2.

For a more rapid and routine analysis, the inventors will employ a double sandwich ELISA assay in which ELISA plates were first coated with a MAb against dectin-1 or dectin-2, incubated with test samples, and finally incubated with polyclonal antibodies against dectin-1 or dectin-2. The amounts of dectin-1 or dectin-2 in the test samples will be determined based on the amounts of polyclonal antibodies binding to the plates. Purified His-dectin-1 or His-dectin-2 proteins will serve as a standard in these assays. In this regard, the inventors have already developed MAb against dectin-2 (MAD2-Rhi) that recognize both recombinant His-dectin-2 and native forms of dectin-2.

Relative protein amounts of dectin-1 or dectin-2 may not necessarily represent relative biological activities. This is especially the case when dectin-1 or dectin-2 proteins are degraded and/or denatured during purification procedures or if different isoforms of dectin-1 or dectin-2 protein exhibit different degrees of biological activity. Therefore, it will be important to measure relative biological activity. The present inventors prefer to determine the biological activity based on the capacity to bind to T cell surfaces. His-tagged dectin-1 or His-tagged dectin-2 protein will be radiolabeled with $^{125}$I or $^{35}$S or labeled in other ways (e.g., fluorescence-labeled or biotinylated) and then examined for binding to the surface of splenic T cells or T cell lines in the presence or absence of each test sample. If the sample inhibits the binding of His-tagged dectin-1 or His-tagged dectin-2, it will indicate the biological activity. One unit of activity will be defined as the activity required for causing 50% inhibition of the binding of His-tagged dectin-1 or His-tagged dectin-2. However, using other assays, the definition of a unit of activity naturally vary. It may be assessed as, for example, the activity to block DC-induced activation of T cells (in antigen presentation assay) or to block the binding of T cells to DC (in cell adhesion assays).

As is generally known in the art, to determine the specific activity, one would calculate the number of units of activity per milligram of total protein. In the purification procedure, the specific activity of the starting material, i.e., tissue extract, would represent the specific activity of the dectin-1 or dectin-2 in its natural state. At each step, one would generally expect the specific activity of the dectin-1 or dectin-2 to increase above this value, as it is purified relative to its natural state. In preferred embodiments, it is contemplated that one would assess the degree of purity of a given dectin-1 or dectin-2 fraction by comparing its specific activity to the specific activity of the starting material, and representing this as X-fold purification. The use of "fold purification" is advantageous as the purity of an inhibitory fraction can thus be compared to another despite any differences which may exist in the actual units of activity or specific activity.

It is contemplated that the dectin-1 or dectin-2 of the present invention be purified to between about 10-fold and about 30-fold, and preferably, of between about 30-fold and about 100-fold, and even more preferably, to about 300-fold, relative to its natural state.

The preferred purification method disclosed hereinbelow contains several steps and represents the best mode presently known by the inventors to prepare a substantially purified dectin-1 or dectin-2 protein. This method is currently preferred as it results in the substantial purification of the protein or polypeptide, as assessed by western blotting, in yields sufficient for further characterization and use. This preferred mode of dectin-1 or dectin-2 protein or polypeptide purification involves the execution of certain purification steps in the order described hereinbelow. However, as is generally known in the art, it is believed that the order of conducting the various purification steps may be changed, or that certain steps may be omitted, and still result in a suitable method for the preparation of a substantially purified dectin-1 or dectin-2 protein or polypeptide As mentioned above, although preferred for use in certain embodiments, there is no general requirement that the dectin-1 or dectin-2 proteins or polypeptides always be provided in their most purified state. Indeed, it is contemplated that less substantially purified proteins or polypeptides, which are nonetheless enriched in dectin-1 or dectin-2 activity relative to the natural state, will have utility in certain embodiments. For example, less purified dectin-1 or dectin-2 preparations may contain molecules that are associated naturally with dectin-1 or dectin-2. If so, this may, ultimately, lead to the identification of unique molecules that associate with dectin-1 or dectin-2 on the cell surfaces (e.g., co-receptors) or in the cytoplasma (e.g., signaling components).

Methods exhibiting a lower degree of relative purification may have advantages in total recovery of protein product, or in maintaining the activity of an expressed protein. Inactive products also have utility in certain embodiments, such as, e.g., in antibody generation.

Partially purified dectin-1 or dectin-2 fractions for use in such embodiments may be obtained by subjecting DC or XS52 cell extract to one or a combination of the steps described. Substituting certain steps with improved equivalents is also contemplated to be useful. For example, it is appreciated that a cation-exchange column chromatography performed utilizing an HPLC apparatus will generally result in a greater-fold purification than the same technique utilizing a low pressure chromatography system.

However, it is known that the migration of a polypeptide can vary, sometimes significantly, with different conditions of SDS/PAGE (Capaldi et al., 1977, incorporated herein by reference). It will therefore be appreciated that under differing electrophoresis conditions, these molecular weights may vary.

2. Biologically Functional Equivalents and Structural Equivalents

As mentioned above, modification and changes may be made in the structure of dectin-1 or dectin-2 and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules, receptors, or T cells. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with countervailing (e.g., antagonistic) properties. It is thus contemplated by the inventors that various changes may be made in the sequence of dectin-1 or dectin-2 proteins or polypeptides (or underlying DNA) without appreciable loss of their biological utility or activity.

In terms of functional equivalents, it is also well understood by the skilled artisan that, inherent in the definition of a biologically functional equivalent protein or polypeptide, is the concept that there is a limit to the number of changes that may be made within a defined portion of the molecule and still result in a molecule with an acceptable level of equivalent biological activity. Biologically functional equivalent polypeptides are thus defined herein as those polypeptides in which certain, not most or all, of the amino acids may be substituted. Of course, a plurality of distinct proteins/polypeptides with different substitutions may be made and used in accordance with the invention.

It is also well understood that where certain residues are shown to be particularly important to the biological or structural properties of a protein or polypeptide, e.g., residues in active sites, such residues may not generally be exchanged.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine; and phenylalanine, tryptophan and tyrosine; are defined herein as biologically functional equivalents.

Conservative substitutions well known in the art include, for example, the changes of alanine to serine; arginine to lysine; asparagine to glutamine or histidine; aspartate to glutamate; cysteine to serine; glutamine to asparagine; glutamate to aspartate; glycogen to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein or polypeptide thereby created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented herein (at page 29) for use in such embodiments, as well as for other uses, such as in the design of probes and primers and the like.

Polypeptides corresponding to one or more antigenic determinants, or "epitopic core regions", of dectin-1 or dectin-2 can also be prepared. Such polypeptides should generally be at least five or six amino acid residues in length, and may contain up to about 35–50 residues or so.

Synthetic polypeptides will generally be about 35 residues long, which is the approximate upper length limit of automated polypeptide synthesis machines, such as those available from Applied Biosystems (Foster City, Calif.). Longer polypeptides may also be prepared, e.g., by recombinant means.

U.S. Pat. No. 4,554,101 (Hopp, incorporated herein by reference) teaches the identification and preparation of epitopes from primary amino acid sequences on the basis of hydrophilicity. Through the methods disclosed in Hopp, one of skill in the art would be able to identify epitopes from within an amino acid sequence such as the extracellular sequence(s) disclosed herein (SEQ ID NO:8 or SEQ ID NO:21).

Numerous scientific publications have also been devoted to the prediction of secondary structure, and to the identification of epitopes, from analyses of amino acid sequences (Chou and Fasman, 1974a,b; 1978a,b, 1979). Any of these may be used, if desired, to supplement the teachings of Hopp in U.S. Pat. No. 4,554,101.

Moreover, computer programs are currently available to assist with predicting antigenic portions and epitopic core regions of proteins. Examples include those programs based upon the Jameson-Wolf analysis (Jameson and Wolf, 1988; Wolf et al., 1988), the program PepPlot® (Brutlag et al., 1990; Weinberger et al, 1985), and other new programs for protein tertiary structure prediction (Fetrow and Bryant, 1993). Further commercially available software capable of carrying out such analyses is termed MacVector (IBI, New Haven, Conn.).

Using the above described methods, the inventors have identified a highly antigenic peptide sequence of dectin-1 (SEQ ID NO:11) and raised rabbit polyclonal antibodies against the synthetic peptides corresponding to this sequence. The antisera were then purified by affinity chromatography using the same peptides, and resulting antibodies (BAD1-Pep) showed monospecific recognition of both recombinant His-dectin-1 and native forms of dectin-1 proteins.

In further embodiments, major antigenic determinants of a polypeptide may be identified by an empirical approach in which portions of the gene encoding the polypeptide are expressed in a recombinant host, and the resulting proteins tested for their ability to elicit an immune response. For example, PCR™ can be used to prepare a range of polypeptides lacking successively longer fragments of the C-terminus of the protein. The immunoactivity of each of these polypeptides is determined to identify those fragments or domains of the polypeptide that are immunodominant. Further studies in which only a small number of amino acids are removed at each iteration then allows the location of the antigenic determinants of the polypeptide to be more precisely determined.

Once one or more such analyses are completed, polypeptides are prepared that contain at least the essential features of one or more antigenic determinants. The polypeptides are then employed in the generation of antisera against the polypeptide. Minigenes or gene fusions encoding these determinants can also be constructed and inserted into expression vectors by standard methods, for example, using PCR™ cloning methodology.

The use of such small polypeptides for vaccination typically requires conjugation of the polypeptide to an immunogenic carrier protein, such as hepatitis B surface antigen, keyhole limpet hemocyanin or bovine serum albumin. Methods for performing this conjugation are well known in the art.

In addition to the peptidyl compounds described herein, the inventors also contemplate that other sterically similar compounds may be formulated to mimic the key portions of the polypeptide structure. Such compounds, which may be termed peptidomimetics, may be used in the same manner as the polypeptides of the invention and hence are also functional equivalents.

Certain mimetics that mimic elements of protein secondary structure are described in Johnson et al. (1993). The underlying rationale behind the use of polypeptide mimetics is that the polypeptide backbone of proteins exists chiefly to orientate amino acid side chains in such a way as to facilitate molecular interactions, such as those of antibody and antigen. A polypeptide mimetic is thus designed to permit molecular interactions similar to the natural molecule.

Some successful applications of the polypeptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

The generation of further structural equivalents or mimetics may be achieved by the techniques of modeling and chemical design known to those of skill in the art. The art of receptor modeling is now well known, and by such methods a chemical that binds to the T cell dectin-1 or dectin-2 receptor can be designed and then synthesized. It will be understood that all such sterically similar constructs fall within the scope of the present invention.

3. Dectin-1 or Dectin-2 Isoforms

One or more truncated forms of dectin-1 and dectin-2 transcripts have also been observed. Using methods similar to those developed and employed in previous studies, the inventors have determined the identities of the truncated dectin-1 and dectin-2 mRNAs. The truncated form of dectin-1, termed "Tβ isoform," (SEQ ID NO:13) was found to contain a 45 amino acid deletion in the connecting domain, compared with the full-length dectin-1 (Tα) (SEQ ID NO:2). The inventors have also identified, in addition to the full length dectin-2 (Tα) (SEQ ID NO:4), four isoforms: a) Tβ with a 65 amino acid deletion primarily in the transmembrane and connecting domains (SEQ ID NO:14); b) Tγ with a 34 amino acid deletion primarily in the connecting domain (SEQ ID NO:15);

c) Tδ with a 41 amino acid deletion in the C-terminus of the CRD domain, in addition to the same 34 amino acid deletion seen in Tγ (SEQ ID NO:16); and d) Tβ with a 43 amino acid deletion within the CRD domain (SEQ ID NO:17).

These truncated forms of dectin-1 or dectin-2 transcripts have been detected not only in the XS52 DC line, but also in spleen cells and epidermal cells. Therefore, DC in normal tissues express mRNAs for different isoforms of dectin-1 and dectin-2.

Putative dectin-1 or dectin-2 isoforms have also been detected at protein levels. In western blotting, anti-dectin-1 antibodies (BAD1-Pep and BAD1-Rhi) detected multiple bands, ranging from 33 kD to 41 kD, in the XS52 DC extract. Likewise, anti-dectin-2 monoclonal antibodies (MAD2-Rh1) detected multiple bands from 19 kD to 32 kD in this extract.

With respect to molecular basis for the generation of different isoforms, the inventors have identified that alternative splicing is responsible. More specifically, the genomic DNA for dectin-2 contains six exons with exon 1 encoding primarily the cytoplasmic domain, exon 2 encoding primarily the transmembrane domain, exon 3, encoding primarily the connecting domain, and exons 4, 5, and 6 encoding the CRD (SEQ NO:33). Importantly, truncated dectin-2 mRNAs have been identified to contain total or partial deletion of one or two of these exons (see FIG. 6B). Sequences corresponding to the conserved donor site and the acceptor site have been detected in all intron-exon splicing junctions, including the splicing junctions that occur within a single exon.

As used hereinbelow, the terms dectin-1 and/or dectin-2 should be interpreted to include not only the full length molecules but also the isoforms described herein, glycosylated forms as well as non-glycosylated forms of the molecules, and other members of the dectin family.

In this regard, reduced amino acid sequences for dectin-1 or dectin-2 contain two or one putative N-glycosylation sites, respectively. The inventors have observed that treatment of native dectin-1 proteins with glycosidases results in the appearance of an additional dectin-1 species with a substantially reduced molecular weight, suggesting that native dectin-1 proteins are indeed glycosylated.

4. Production of Antibodies Against Dectin-1 or Dectin-2

Means for preparing and characterizing antibodies are well known in the art (See, e.g., Antibodies: A Laboratory Manual, Cold Spring Harbor Laboratory, 1988; incorporated herein by reference). The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention (either with or without prior immunotolerizing, depending on the antigen composition and protocol being employed) and collecting antisera from that immunized animal.

A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, µ-maleimidobencoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, toxins or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion. MHC antigens may even be used.

Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or down-regulate suppressor cell activity. Such BRMs include, but are not limited to, Cimetidine (CIM; 1200 mg/d) (Smith/Kline, PA); or low-dose Cyclophosphamide (CYP; 300 mg/m$^2$) (Johnson/Mead, NJ) and cytokines such as γ-interferon, IL-2, or IL-112 or genes encoding proteins involved in immune helper functions, such as CD80 (B7-1) and CD86 (B7-2).

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, may also be given. The process of boosting and titering is repeated until a suitable titer is achieved. When a desired level of immunogenicity is obtained, the immunized animal can be bled and the serum isolated and stored, and/or the animal can be used to generate monoclonal antibodies (MAbs).

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a polypeptide bound to a solid matrix, or by using, e.g., protein A or protein G chromatography.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified dectin-1 or dectin-2 protein, polypeptide or peptide (or any DC composition, if used after tolerization to common antigens). The immunizing composition is administered in a manner effective to stimulate antibody producing cells.

The methods for generating MAbs generally begin along the same lines as those for preparing polyclonal antibodies. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions. The inventors have generated the MAb against mouse dectin-2 in rats (MAD2-Rhi), which recognize both recombinant His-dectin-2 and native forms of dectin-2 proteins. This was primarily because it is technically difficult to immune mice with molecules of mouse origin. On the other hand, the inventors will prefer mice for the generation of MAb against human dectin-1 or human dectin-2.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is accessible.

Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis.

Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, rapid and easy to use, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways.

A sample of the hybridoma can be injected (often into the peritoneal cavity) into a histocompatible animal of the type that was used to provide the somatic and myeloma cells for the original fusion (e.g, a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration.

The individual cell lines could also be cultured in vitro, where the MAbs are naturally secreted into the culture medium from which they can be readily obtained in high concentrations. In this regard, the inventors have generated a panel of MAb against recombinant His-dectin-2 proteins (produced in *E. coli*). Rats were immunized with His-dectin-2 and hybridomas were screened in western blotting for their reactivity to His-dectin-1. Resulting MAb (MAD2-Rhi) recognize not only the His-dectin-1, but also native forms of dectin-2 proteins in the extract from XS52 DC.

In another embodiment, MAbs will be chimeric MAbs, including "humanized" MAbs. In such an approach, the chimeric MAb is engineered by cloning recombinant DNA containing the promoter, leader, and variable-region sequences from a mouse anti-dectin producing cell and the constant-region exons from a human antibody gene. That is, mouse complementary determining regions ("CDRs") are transferred from heavy and light V-chains of the mouse Ig into a human V-domain. This can be followed by the replacement of some human residues in the framework regions of their murine counterparts.

The antibody encoded by such recombinant genes is a mouse-human chimera. Its antibody specificity is determined by the variable region derived from mouse sequences. Its isotype, which is determined by the constant region, is derived from human DNA. These humanized anti-dectin antibodies are especially suitable for use in in vivo diagnostic and therapeutic methods. To produce humanized MAb as recombinant proteins, the nucleotide sequence encoding the variable domain of the light and heavy chains of mouse anti-human dectin-1 or mouse anti-human dectin-1 MAb will be first cloned by PCR™ and then inserted into the expression vector containing the human light and heavy chain constant regions. These expression vectors are used routinely by many investigators (Co et al., 1996; Co et al., 1992). It is contemplated that choosing a most appropriate human framework may be required. For example, designing antibodies with minimal positional templates is one way for this purpose (Caouto et al., 1995). Recombinant proteins may be produced in mammalian cells (e.g., mouse myeloma cell line S194) and then purified with protein A sepharose column.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

The MAbs of the invention will be useful in many ways. For example, they can be used to isolate and/or identify DC or the dectin-1 or dectin-2 protein in biological systems or they may be used to inhibit DC-mediated, T cell-induced inflammatory disease.

Figure 3A:
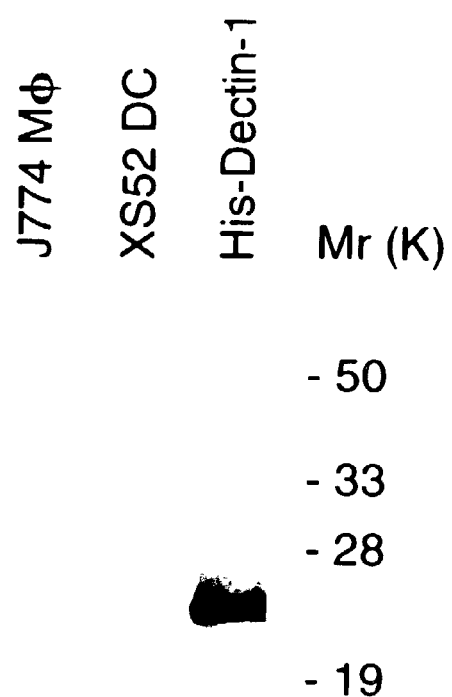
FIG. 3A Scanned images of Dectin-1 protein expression by DC. Cell extracts prepared from XS52 DC or J774 macrophages were examined by immunoblotting using affinity-purified, anti-dectin-1 polypeptide antiserum (BAD1-Pep).
Figure 3A:
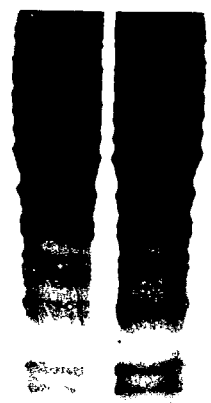
Figure 3B:
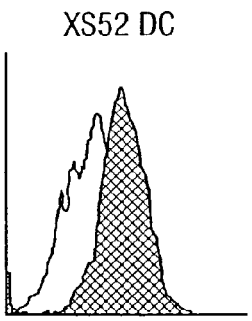
FIG. 3B, FIG. 3C, FIG. 3D, and FIG. 3E. Cell lines were examined by FACS for expression of dectin-1 using the above antibodies (filled histogram) or IgG control (open histograms).

The inventors raised affinity-purified antibodies (BAD1-Pep) against a synthetic polypeptide corresponding to amino acids 75–94 (SEQ ID NO:11). These antibodies were used to immunolabel a major band of 41 kD in an extract of XS52 DC, but not J744 macrophages (FIG. 3A). While this band was considerably larger than the predicted molecular weight (28 kD) for dectin-1, it is believed that the larger molecular weight reflects glycosylation at putative N-glycosylation sites at amino acids 185 and 233. In fact, the inventors have shown that treatment of XS52 DC extracts or purified dectin-1 with glycosidases results in significant reduction in the molecular size (by about 4 kD), as compared to the native form of dectin-1. These same anti-peptide antibodies revealed dectin-1 on the surface of XS52 DC (FIG. 3B).

The inventors also generated rat antibodies (TAD1-Rhi—as described in Example 4) against a fusion protein comprising a His tag and the extracellular domain (amino acids 73–244, SEQ ID NO:8) of dectin-1. This fusion protein, His-dectin-1, migrated as a single mass of 23 kD, corresponding to the predicted molecular size of 21 kD (FIG. 3A).

When splenic DC preparations (containing 80–90% DC and small numbers of other cell types) were double-stained with anti-CD11c MAb (HL3 purchased from PharMingen, San Diego, Calif.) and with rabbit polyclonal anti-dectin-1 antibodies (BAD1-Pep), about 20–40% of the CD11c-positive cells (i.e., DC) exhibited significant labeling with anti-dectin-1. No significant dectin-1 immunolabeling was observed in the CD11c-negative population. These results indicate that dectin-1 protein is expressed at detectable levels and on cell surfaces by a subpopulation of splenic DC and that dectin-1 protein expression occurs almost exclusively within the DC population. Thus, it is shown that antibodies raised to dectin-1 proteins or polypeptides can be used to isolate and/or identify dectin-1 and/or dendritic cells.

It is also contemplated that a molecular cloning approach may be used to generate MAbs. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

It is also contemplated that autoantibodies against dectin-1 or dectin-2 proteins and/or polypeptides may be generated in mice, as well as other species (e.g., humans), under pathological conditions. For example, such autoantibodies may be present in detectable levels in human patients with symptoms for immunodeficiency. Autoantibodies may be detected by ELISA using relevant antibodies that recognize dectin-1 or dectin-2 proteins or polypeptides. ELISA plates will be first coated with (rabbit) anti-dectin-1 or anti-dectin-2 antibodies and then coated with recombinant or native form of dectin-1 or dectin-2. These plates will be incubated with test samples (e.g., human serum) and then with antibodies against (human) immunoglobulin. Alternatively, recombinant or native forms of dectin-1 or dectin-2 may be immobilized directly on the ELISA plates. The amounts of autoantibodies will be determined by measuring the amounts of anti-immunoglobulin antibodies that bind to the plates. This and other assays to measure autoantibodies against dectin-1 or dectin-2 may be useful for diagnostic purposes.

As discussed above, anti-dectin-1 antibodies immunolabeled a subpopulation of CD11c-positive DC in mouse spleen. This implies that these and other antibodies against dectin-1 or dectin-2 may be used to identify one or more specific subsets of DC (by immunolabelling) and to purify such subsets (by a fluorescence-activated cell sorter or by magnetic bead separation).

5. Production of Soluble Forms of Dectin-1 or Dectin-2 Proteins

Additionally, the inventors have provided His-tagged recombinant proteins consisting of 6× histidine and extracellular domains of dectin-1 or dectin-2 (SEQ ID NO:8 and SEQ ID NO:21, respectively). These His-tagged recombinant proteins have been termed His-dectin-1 and His-dectin-2, respectively. Methods for producing these His-tagged proteins can be found in Example 5. It has been found that these His-tagged proteins are useful for the production of antibodies which will block the DC-T cell interaction by interfering with surface dectin-1 or dectin-2 (see Example 4).

These His-dectin-1 or His-dectin-2 proteins are typically solubilized in a biologically active form which will be useful to administer to block the DC-T cell interaction. His-dectin-1 and His-dectin-2 proteins may be produced in bacteria (e.g., *E. coli*), insect cells (e.g., SF-9 cell line), or mammalian cells (e.g., COS cells) and then purified using nickel-affinity chromatography. Preferentially, these proteins may be engineered in such a manner that they are secreted extracellularly. In fact, the inventors have been able to prepare a soluble and secreted form of dectin-1 or dectin-2 in COS cells by introducing a DNA fragment encoding the extracellular domain of dectin-1 (nucleotides 232–820 in SEQ ID NO:1) or dectin-2 (nucleotides 296–772 in SEQ ID NO:3) into the downstream of the immunoglobulin leader sequence (pSecTagB, purchased from Invitrogen, San Diego, Calif.). It is also desirable to establish permanent transfectants secreting soluble forms of His-dectin-1 or His-dectin-2 proteins. In this regard, the inventors have been able to transfect the mouse S1509a tumor line with the above dectin-1-secreting construct (pSTB-1C115) containing a selection marker, zeocin-resistant gene, and establish stable transfectants after selection with zeocin. To test the capacity of soluble dectin-1 or dectin-2 proteins to inhibit DC-T cell interaction, these preparations will be added to the coculture systems that contain DC, T cells (and antigen, if required). Samples that inhibit T cell activation, as assessed by proliferation or cytokine secretion by T cells, will be considered to have the capacity to block DC-T cell interaction.

An alternative approach was to produce chimeric proteins consisting of glutathione S-transferase (GST) (in the N-terminus) and extracellular domains of dectin-1 or dectin-2 (in the C-terminus). When these proteins were produced in *E. coli* and then extracted with high concentrations (8 M) of urea, they remained totally insoluble after dialysis against PBS. On the other hand, the investigators contemplate that the use of GST-fusion proteins may have an advantage over His-tagged proteins in the stability. Therefore, these GST-dectin-1 or GST-dectin-2 fusion proteins may prove useful as antigens for immunization.

As a third alternative strategy, a new vector system (pMAL-c2) that directs the production of fusion proteins in a soluble form to the periplasm of bacteria (New England Biolabs, Beverly, Mass.) may be employed. The fusion partner, maltose-binding protein, will be cleaved from the extracellular domain of dectin-2 by factor Xa protease.

Finally, soluble dectin-1 or dectin-2 may be produced as naturally occurring isoforms. For example, the inventors have identified a dectin-2 isoform (Tβ) (SEQ ID NO:14) that contains a 65 amino acid deletion primarily in the transmembrane and connecting domains. Therefore, it is feasible to purify selectively the dectin-2 Tβ isoform proteins from the DC culture supernatants using anti-dectin-2 antibodies. Alternatively, cDNA encoding the dectin-2 Tβ may be introduced into host cells to produce the Tβ isoform proteins more efficiently.

D. Down-Regulation or Suppression of Expression of Dectin-1 or Dectin-2 Genes

Further aspects of the present invention include the down-regulation or suppression of dectin-1 or dectin-2 genes so that dectin-1 or dectin-2 production is reduced or even eliminated. It is contemplated that the expression of dectin-1 or dectin-2 will be suppressed by the incorporation a DNA segment into the genome of recombinant host cells or animals such that the expression of the dectin-1 or dectin-2 gene is disrupted. Cells and animals that are designed to down-regulate or suppress, either partially or completely, the expression of dectin-1 or dectin-2 genes will be useful for the discovery of drugs which stimulate T cell activation, for research of the immune system and T cell activation, for treatment of diseases associated with or caused by hyper-immunity.

Four basic approaches are contemplated for blocking the expression of an endogenous dectin-1 or dectin-2 gene in recombinant host cells. First, constructs are designed to homologously recombine into particular endogenous gene locus, i.e. the dectin-1 or dectin-2 gene locus, in an antisense orientation rendering the endogenous dectin-1 or dectin-2 gene nonfunctional. Second, constructs are designed to randomly integrate throughout the genome, resulting in loss of expression of the endogenous dectin-1 or dectin-2 gene. Third, constructs are designed to introduce nucleic acids complementary to the target endogenous gene. Expression of RNAs corresponding to these complementary nucleic acids will interfere with the transcription and/or translation of the target sequences. An advantage of all three of these methods is that they may be targeted at any one of several steps in the metabolic pathway which regulates the expression of dectin-1 or dectin-2 genes. And fourth, constructs are designed to introduce nucleic acids encoding ribozymes—RNA-cleaving enzymes—that will specifically cleave a target mRNA corresponding to the endogenous gene.

1. Preparation of Antisense DNA

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. In fact, the investigators have identified that mouse dectin-2 polypeptide is encoded by six exons. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used.

The cDNA or a synthesized polynucleotide may provide more convenient restriction sites for the remaining portion of the construct and, therefore, would be used for the rest of the sequence.

2. Preparation of Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al, 1991; Sarver et al, 1990; Sioud et al., 1992). Recently, it was reported that ribozymes elicited genetic changes in some cell lines to which they were applied; the altered genes included the oncogenes H-ras, c-fos and genes of HIV. Most of this work involved the modification of a target mRNA, based on a specific mutant codon that is cleaved by a specific ribozyme.

3. Use of Homologous Recombination Events

Another approach for blocking of endogenous protein production involves the use of homologous recombination. Homologous recombination relies, like antisense, on the tendency of nucleic acids to base pair with complementary sequences. In this instance, the base pairing serves to facilitate the interaction of two separate nucleic acid molecules so that strand breakage and repair can take place. In other words, the "homologous" aspect of the method relies on sequence homology to bring two complementary sequences into close proximity, while the "recombination" aspect provides for one complementary sequence to replace the other by virtue of the breaking of certain bonds and the formation of others.

Put into practice, homologous recombination is used as follows. First, a target gene is selected within the host cell. Sequences homologous to the target gene are then included in a genetic construct, along with some mutation that will render the target gene inactive (stop codon, interruption, etc.). The homologous sequences flanking the inactivating mutation are said to "flank" the mutation. Flanking, in this context, simply means that target homologous sequences are located both upstream (5') and downstream (3') of the mutation. These sequences should correspond to some sequences upstream and downstream of the target gene. The construct is then introduced into the cell, thus permitting recombination between the cellular sequences and the construct.

As a practical matter, the genetic construct will normally act as far more than a vehicle to interrupt the gene. For example, it is important to be able to select for recombinants and, therefore, it is common to include within the construct a selectable marker gene. This gene permits selection of cells that have integrated the construct into their genomic DNA by conferring resistance to various biostatic and biocidal drugs. In addition, a heterologous gene that is to be expressed in the cell also may advantageously be included within the construct. The arrangement might be as follows:

. . . vector•5'-flanking sequence•heterologous gene•selectable marker gene•flanking sequence-3'•vector . . .

Thus, using this kind of construct, it is possible, in a single recombinatorial event, to (i) "knock out" an endogenous gene, (ii) provide a selectable marker for identifying such an event and (iii) introduce a heterologous gene for expression.

Another refinement of the homologous recombination approach involves the use of a "negative" selectable marker. This marker, unlike the selectable marker, causes death of cells which express the marker. Thus, it is used to identify undesirable recombination events. When seeking to select homologous recombinants using a selectable marker, it is difficult in the initial screening step to identify proper homologous recombinants from recombinants generated from random, non-sequence specific events. These recombinants also may contain the selectable marker gene and may express the heterologous protein of interest, but will, in all likelihood, not have the desired "knock out" phenotype. By attaching a negative selectable marker to the construct, but outside of the flanking regions, one can select against many random recombination events that will incorporate the negative selectable marker. Homologous recombination should not introduce the negative selectable marker, as it is outside of the flanking sequences.

For example, a target gene within a host cell is selected as the location into which a selected gene is to be transferred. Sequences homologous to the target gene are included in the expression vector, and the selected gene is inserted into the vector such that target gene homologous sequences are interrupted by the selected gene or, put another way, such the target gene homologous sequences "flank" the selected gene. In preferred embodiments, a drug selectable marker gene also is inserted into the target gene homologous sequences. Given this possibility it should be apparent that the term "flank" is used broadly herein, namely, as describing target homologous sequences that are both upstream (5') and downstream (3') of the selected gene and/or the drug selectable marker gene. In effect, the flanking sequences need not directly abut the genes they "flank."

Application of a drug which selects for the negative marker gene to such cells will permit isolation of recombinants. On the other hand, site-specific recombination, relying on the homology between the vector and the target gene, will result in incorporation of the selected gene and the drug selectable marker gene only; negative marker gene sequences will not be introduced in the homologous recombination event because they lie outside the flanking sequences. Thus these cells will be drug resistant but not acquire the negative marker sequences and remain insensitive to a drug. This double-selection procedure should yield recombinants that lack the target gene and express the selected gene. Further screens for these phenotypes, either functional or immunological, may be applied.

A modification of this procedure is one where no selected gene is included, i.e., only the selectable marker is inserted into the target gene homologous sequences. Use of this kind of construct will result in the "knock-out" of the target gene only. Again, proper recombinants are screened by drug resistance.

4. Random Integration Into the Genome

Though lacking the specificity of homologous recombination, there may be situations where random integration will be used as a method of knocking out a particular endogenous gene. Unlike homologous recombination, the recombinatorial event here is completely random, i.e., not reliant upon base-pairing of complementary nucleic acid sequences. Random integration is like homologous recombination, however, in that a gene construct, often containing a heterologous gene and a selectable marker, integrates into the target cell genomic DNA via strand breakage and reformation.

Because of the lack of sequence specificity, the chances of any given recombinant integrating into the target gene are greatly reduced. Also possible is integration into a second loci, resulting in the loss of expression of the gene of interest. This second locus could encode a transcription factor needed for expression of the first gene, a locus control region needed for the expression of the first gene, etc. As a result, it may be necessary to "brute force" the selection process. In other words, it may be necessary to screen hundreds of thousands of drug-resistant recombinants before a desired mutant is found. Screening can be facilitated, for example, by examining recombinants for expression of the target gene using immunologic or even functional tests; expression of the target gene indicate recombination elsewhere and, thus, lack of suitability.

E. Preparation and Use of Knockout Constructs and Knockout Animals

1. Preparation of Knockout Constructs

"Knockout constructs" typically refer to a nucleic acid sequence that is designed to decrease or suppress the expression of a protein, in this case dectin-1 or dectin-2, encoded by endogenous DNA sequences in a cell. These knockout constructs are generally designed following one of the basic approaches described above in Section D.

In some cases, it will be desirable to actually remove a portion or even all of one or more exons of the dectin-1 or dectin-2 gene to be suppressed so as to keep the length of the knockout construct comparable to the original genomic sequence when an antisense and/or marker gene is inserted in the knockout construct. In these cases, the genomic DNA is cut with appropriate restriction endonucleases such that a fragment of the proper size can be removed.

A marker gene, e.g. an antibiotic resistance gene such as neo, is usually operably linked to its own promoter or to another strong promoter from any source that will be active or can easily be activated in the cell into which it is inserted; however, the marker gene need not have its own promoter attached as it may be transcribed using the promoter of the dectin-1 or dectin-2 gene to be suppressed.

The DNA sequence encoding the marker gene is ligated into the genomic DNA sequence at an appropriate position such that the marker gene is operatively linked to a promoter using methods well known to the skilled artisan and described in Sambrook et al, 1989.

The resulting ligated knockout construct may be inserted directly into embryonic stem (ES) cells as discussed below, or it may first be placed into a suitable vector for amplification prior to insertion into ES cells.

2. Transfection of Embryonic Stem Cells

ES cells are typically selected to prepare knockout constructs because of their ability to integrate into and become part of the germ line of a developing embryo so as to create germ line transmission of the knockout construct. Thus, any ES cell line that is believed to have this capability is suitable for use herein.

Insertion of the knockout construct into the ES cells can be accomplished using a variety of methods well known in the art including for example, electroporation, microinjection, and calcium phosphate treatment (see Lovell-Badge, in Robertson, ed., 1987).

For insertion of the DNA sequence, the knockout construct DNA is added to the ES cells under appropriate conditions for the insertion method chosen. Where more than one construct is to be introduced into the ES cell, DNA encoding each construct can be introduced simultaneously or one at a time.

The cells are then screened for the presence of the knockout construct. Screening can be done using a variety of methods well known to those of skill in the art. For example, where the marker gene is an antibiotic resistance gene, the cells are cultured in the presence of an otherwise lethal concentration of antibiotic. Those cells that survive have presumably integrated the knockout construct. If the marker gene is other than an antibiotic resistance gene, a Southern blot of the ES cell genomic DNA can be probed with a sequence of DNA designed to hybridize only to the marker sequence. Alternatively, if the marker gene is a gene that encodes an enzyme whose activity can be detected (e.g., β-galactosidase), the enzyme substrate can be added to the cells under suitable conditions, and the enzymatic activity can be analyzed.

The desired location of the insertion of the knockout construct is in a complementary position to the DNA sequence to be knocked out. Typically, less than about 1–5 percent of the ES cells that take up the knockout construct will actually integrate the knockout construct in the desired location. To identify those cells with proper integration of the knockout construct, the DNA can be extracted from the cells using standard methods such as those described by Sambrook et al., 1989. The DNA can then be probed on a Southern blot with a probe or probes designed to hybridize in a specific pattern to genomic DNA digested with (a) particular restriction enzyme(s). Alternatively, or additionally, the genomic DNA can be amplified by PCR™ with probes specifically designed to amplify DNA fragments of a particular size and sequence.

3. Injection/Implantation of Embryos

After suitable ES cells containing the knockout construct in the proper location have been identified, the cells are inserted into an embryo. Insertion may be accomplished in a variety of ways, however, a preferred method is by microinjection. After the ES cell has been introduced into the embryo, the embryo is implanted into the uterus of a pseudopregnant foster mother.

4. Screening for Presence of Knockout Gene

Offspring may be screened for the presence of the knockout construct using Southern blots and/or PCR™ as described above. Other means of identifying and characterizing the knockout offspring are available. For example, northern blots can be used to probe the mRNA for the presence or absence of transcripts encoding either the gene knocked out, the marker gene, or both. In addition, western blots can be used to assess the level of expression of the gene knocked out in various tissues of these offspring by probing the western blot with an antibody against the protein(s) encoded by the gene knocked out (e.g., dectin-1 or dectin-2), or an antibody against the marker gene product, where this gene is expressed. Alternatively, in situ analysis (such as fixing the cells and labeling with antibody) and/or FACS (fluorescence activated cell sorting) analysis of various cells from the offspring can be conducted using suitable antibodies to look for the presence or absence of the knockout construct gene product (dectin-1 or dectin-2). In addition, the marker gene(s) utilized may express a phenotype, e.g. fur color, which can be used to visually determine the presence of the knockout construct.

5. Uses of Knockout Mammals

It is contemplated that the knockout mammals of the present invention will have several obvious utilities. For example, these animals may serve as a useful model for studying the function of dectin-1 or dectin-2, as well as their respective ligand(s). In this regard, the inventors will produce dectin-1/dectin-2 double knockout animals by crossbreeding the single knockout animals. These animals, either single knockout or double knockout animals, may also serve as a useful tool to search for molecules that substitute the function of dectin-1 or dectin-2. That is, if the dectin-1/dectin-2 knockout animals exhibit normal immunity, one should be able to identify, using such animals, the mechanisms by which DC deliver T cell activation signals in a dectin-independent manner.

Another utility is to search for candidate molecules (e.g., drugs, reagents, compounds, biological materials, extracts, peptides, carbohydrates, lipids) that modulate the expression or function of dectin-independent T cell activation pathways. For example, if the dectin-1/dectin-2 knockout mice may exhibit immunological deficiency, one may examine test samples for their capacity to improve such deficiency in those animals. It is envisioned that screening for useful drugs will involve administering the candidate drug over a range of doses and assaying for T cell activation at various time points in order to evaluate for the immunomodulatory effect(s) of the candidate drug.

If dectin-1 or dectin-2 mutation is found in human patients with immunological abnormalities, dectin-1 or dectin-2 knockout animals will serve as a model for such disease(s). More specifically, this model may be useful to develop rapid screening methods of the disease and to search for therapeutic substances or establish therapeutic modalities to treat the disease.

A knockout mammal of the present invention could be used to study the development of immune system. In this regard, if such animals are defective in T cell-mediated immunity, but not in B cell-mediated immunity, they may serve as useful experimental models to study the role of B cells in various immunological responses.

Methods described for the production of knockout mammals may be used to knockout the dectin-1 or dectin-2 gene in human patients. Such an approach could be potentially very useful for the treatment of human patients. For example, patients with hyperimmune responses to environmental antigens (allergic diseases) or autoantigens (autoimmune diseases) may be treated by abrogating dectin-1 or dectin-2 expression on the DC. Once again, it is expected that transient depletion of dectin-1 or dectin-2 would be sufficient to induce relative long-term, immunological unresponsiveness to undesirable antigens (through clonal anergy or clonal depletion). Although such strategies (knocking out a gene) have not yet been actually performed in humans, the dectin-1 or dectin-2 gene may serve as a reasonable candidate for this kind of a clinical approach.

Alternatively, in vitro gene knockout may be employed for clinical purposes. Dectin-1 or dectin-2 gene may be disrupted from the DC population isolated from human patients. Subsequently, these DC expressing no or lower levels of dectin-1 or dectin-2 may be pulsed in vitro with relevant antigens (either with native molecules or synthetic peptides, or through cDNA transfection) and then injected back to the same patients. Such an approach may also lead to relatively long-term, immunological unresponsiveness to unwanted antigens.

F. Development of Dectin-Related Agents and Assays

It is contemplated that the dectin-related agents described herein will be useful in many areas, for example in screening assays, immunoassays, immunodetection methods, suppressing immunity, augmenting immunity, examining immunological functions of DC and/or T cells, monitoring amounts and qualities of dectin-1 and/or dectin-2 in clinical samples or to target the expression of foreign genes into DC, all as described in more detail herein. As used herein, the term "dectin-related agents" refers to full length as well as partial DNA segments; full length, isoforms, mutated, truncated or elongated forms of dectin-1 and/or dectin-2 proteins and polypeptides; other members of the dectin family; isolated and purified native dectin-1 and/or dectin-2 as well as recombinantly produced dectin-1 and/or dectin-2; antibodies raised to any of the above forms; cells and animals engineered to overproduce dectin-1 or dectin-2; and cells and animals engineered not to produce dectin-1 or dectin-2.

The dectin-related agents described herein may, of course, additionally be used to search for molecules that modulate the expression and/or function of dectins (e.g., chemicals, synthetic peptides, carbohydrates, lipids, recombinant proteins, cell extracts, and supernatant, etc.). This may, for example, involve the use of dectin-1 and/or dectin-2 transfectants to search for molecules that block T cell activation, or the use of recombinant dectin-1 and/or dectin-2 for molecules that block the binding of His-dectin-1 to T cells, or the use of XS52 cells and antibodies against dectin-1 and/or dectin-2 for molecules that modulate dectin-1 or dectin-2 expression by DC.

Another contemplated use of the agents of the invention is their use to regulate cell differentiation toward DC, for example, to establish DC lines by introducing dectin promoters. This may be accomplished by using the 5'-flanking region of the dectin-1 and/or dectin-2 gene to drive cellular differentiation toward DC or by using oncogenes (e.g., c-myc) driven by DC-specific promoters.

The inventors also contemplate that the agents described herein may be used to upregulate as well as downregulate T cell-mediated immunity in vivo. To upregulate immunity, dectin-1 or dectin-2 will be introduced into individuals by means of cDNA transfection. For example, DC purified from a patient may be engineered to overexpress dectin-1 or dectin-2 proteins by transfection with respective cDNA that is driven by a strong promoter. These transfectants will then be injected back to the same patient. If it is desired to target a certain antigen, those DC expressing high levels of dectin-1 or dectin-2 will be labeled with such an antigen at a protein level (by pulsing with antigen in vitro) or at a DNA level (by cotransfecting with a cDNA encoding the desired antigen).

Another example for enhancing T cell-mediated immunity is the use of dectin-1 or dectin-2 promoters to target the expression of the gene to DC in the genetic immunization protocols. It is now feasible to deliver certain genes into living animals (including humans) by injecting DNA directly in a naked form or by delivering metal particles coated with DNA using high pressure apparatus ("gene guns"). This method has been used successfully to induce protective immunity against infectious pathogens or cancer development. However, it remains unknown which cell types incorporate the DNA, express the protein, and present its antigenic fragments to effector T cells. The present inventors have isolated a putative promoter region of dectin-2 gene. This 3.2 kb DNA fragment did drive significant transcription of the luciferase gene in the XS DC lines, but not in NS fibroblast, Pam212 keratinocyte, or J774 macrophage lines. These observations suggest that dectin-2 promoters are transcriptionally active only in DC, thus, forming both technical and conceptual basis for targeting gene expression to DC, i.e., delivering foreign genes selectively into DC by using promoter sequences of dectin-1 or dectin-2. Using this method, one can introduce cDNA encoding antigenic polypeptides of infectious pathogens or tumor cells (or even the entire cDNA library) selectively into DC in order to initiate protective immunity. One major advantage for the DC-targeted, genetic vaccination is that it will prevent the induction of tolerance, an event that is frequently inducible when the antigen is presented by non-professional antigen presenting cells in the absence of required co-stimulatory signals.

As discussed above, dectin-related reagents may be used to suppress T cell-mediated immunity. For example, antibodies against dectin-1 or dectin-2 may be used in this manner. In fact, the inventors have been able to inhibit nearly completely DC-induced activation of T cells in vitro with polyclonal antibodies against dectin-1. Another example is the use of soluble forms of dectin-1 or dectin-2. In this regard, DC are known to express CD80 and CD86 molecules, which bind to their ligands, CD28 and CTLA-4, expressed on T cells. The ligation of CD80/CD86 (on DC) with CD28/CTLA-4 (on T cells) is required for DC-dependent, full activation of T cells. This ligation has been blocked relatively effectively by MAb against CD80 or CD86 and even more completely by CTLA-4-Ig fusion proteins that contain the extracellular domain of CTLA-4. CTLA-4-Ig fusion proteins have been used successfully to inhibit DC-dependent activation of T cells in vitro. Moreover, injection of the same preparations into study animals resulted in prevention of several immune reactions, including autoimmune diseases and hypersensitivity diseases. Similar inhibition has also been achieved with CD80-Ig or CD86-Ig fusion proteins. Based on these previous observations, it is expected that extracellular domains of dectin-1 or dectin-2, when administered in soluble forms, will exhibit beneficial effects to prevent or even treat immunological disorders. The present invention also includes the use of soluble forms of dectin-ligands. These approaches are expected to block DC-induced activation of T cells.

Figure 5B:
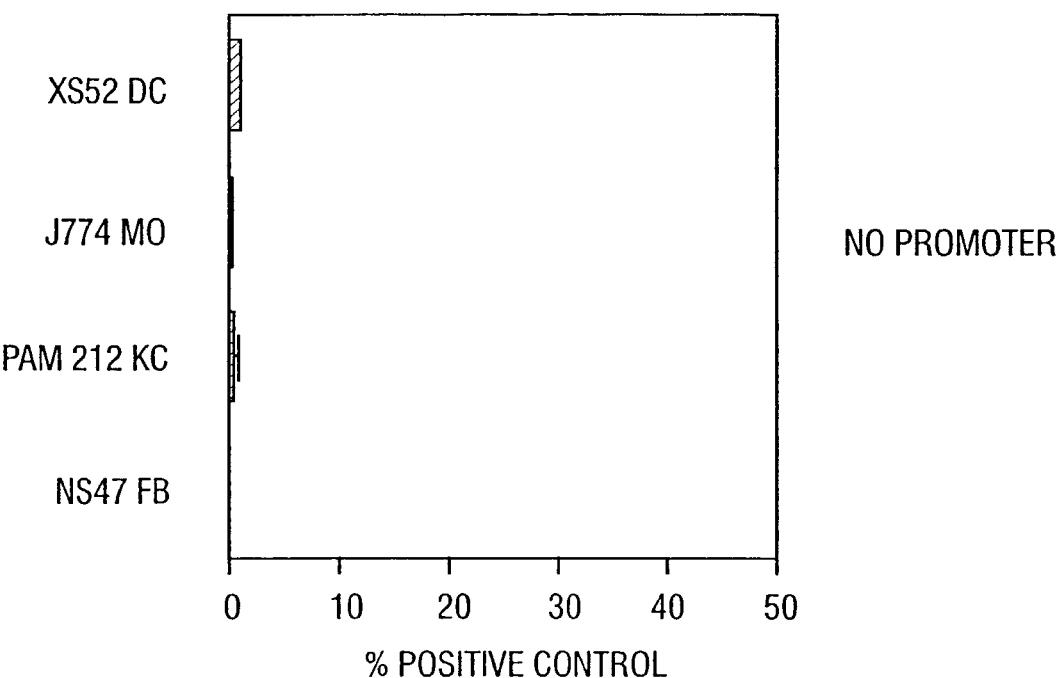
Figure 5C:
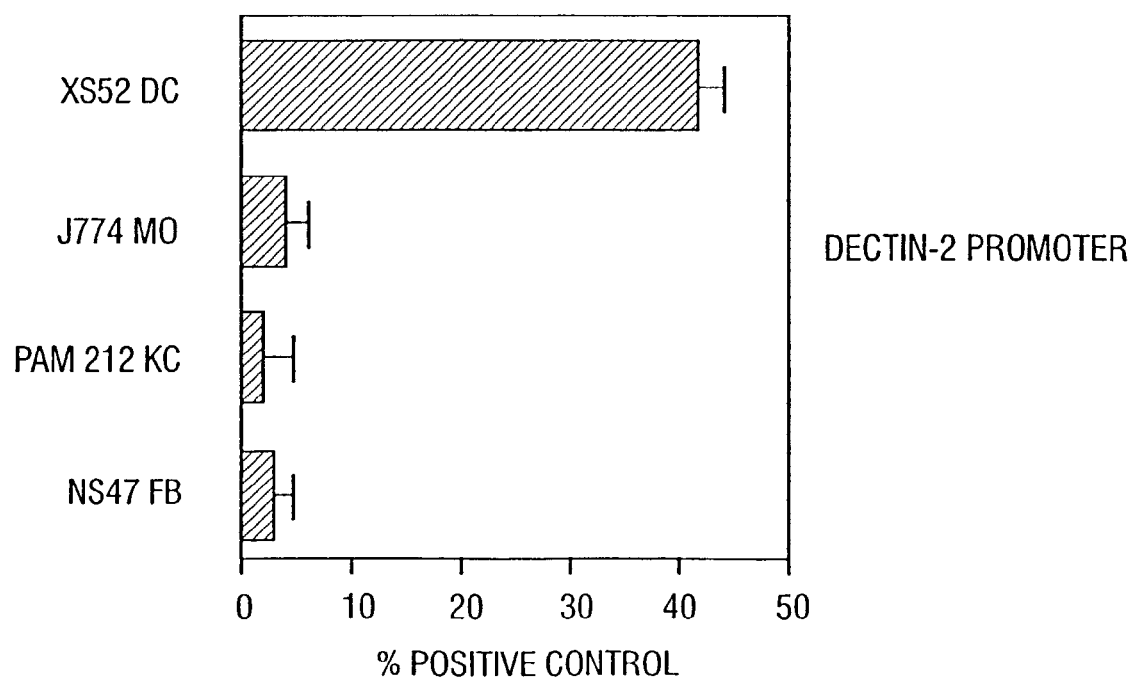

Another important consequence of interfering with dectin-dependent T cell activation cascade is the induction of clonal anergy. In this regard, blocking of the CD80/CD86-dependent cascade leads not only to a failure of T cell activation, but also to unresponsiveness of the T cells to the same antigen, a state termed "clonal anergy." From the viewpoint that the CD80/CD86 cascade and the dectin-dependent cascade are both required for T cell activation, it is expected that blocking of the dectin-dependent signaling also induce clonal anergy. If this is correct, it will then be practically feasible to induce clonal anergy in T cell populations that are otherwise reactive to unwanted antigens (e.g., autoantigens or environmental antigens), thereby treating autoimmune diseases or hypersensitivity reactions. One approach to this aim is the use of anti-dectin-1 or dectin-2 antibodies or the antisense oligonucleotides for dectin-1 or dectin-2. DC purified from patients will be first treated with anti-dectin-1 or dectin-2 antibodies or with the antisense nucleotides. These DC, which express reduced amounts of functional dectin-1 or dectin-2 on their surfaces, will then be pulsed with the targeted antigen at a protein level or be transfected with cDNA encoding such antigen. These engineered DC, expressing reduced dectin-1 or dectin-2 and carrying the targeted antigen, will be injected back to the same patients. Using this method, one can target clonal anergy to those T cells that are reactive to the unwanted antigen. Another important aspect in this invention is the identification of a promoter for the dectin-2 gene. This DNA fragment isolated from 5'-flanking regions of the dectin-2 genomic DNA has been proven to be transcriptionally active in DC, but not in other cell types (FIG. 5B). Therefore, DNA sequences in this fragment (SEQ ID NO:34) or a putative promoter for the dectin-1 gene may be used to drive the transcription of exogenous DNA in a DC-specific manner. One obvious utility for such strategy (DC-targeted DNA vaccines) is to augment immune responses against infectious pathogens or cancers. For this aim, the inventors will design constructs that contain the putative dectin-1 or dectin-2 promoter sequences in the upstream of the cDNA encoding relevant antigens in viruses, bacteria, or parasites or cDNA encoding tumor associated antigens. It is also feasible to construct an entire cDNA library from infectious microorganisms or cancer cells under the control of dectin-1 or dectin-2 promoter. Such constructs will be administered into animals (including human patients) through injections, gene gun, or viral vectors.

A similar method may be used to suppress or downregulate the immune reactions. For example, one may treat human patients who are hypersensitive to a given antigen by replacing the peptides derived from the pathogenic antigen on MHC class I or class II molecules with unrelated, non-pathogenic peptides that bind to the MHC molecules with higher affinities. More specifically, patients will be administered with a construct that contains dectin-1 or dectin-2 promoter in the upstream of the cDNA encoding such non-pathogenic peptides. Such a construct will then be transcribed and translated only within DC, thereby replacing the pathogenic peptides on their MHC molecules with non-pathogenic peptides.

It is also feasible to generate transgenic animals that express "marker genes" (e.g., green fluorescence proteins, β-galactosidase) under the control of the dectin-2 (or dectin-1) promoter. Such transgenic animals will be useful for studying the development of DC. Moreover, these animals may serve as useful tool to search for candidate substances that upregulate or downregulate DC development. For this purpose, transgenic animals will be treated with candidate substances and then examined for the number of DC expressing the marker gene product. Substances that increase the number of DC may be used to augment the immunity in animals (including human patients), whereas substances that decrease their number may be used to suppress the immunity in immunosuppressed animals (including human patients) with hyperimmunity.

The inventors have identified DC-specific promoter in the 5'-flanking regions of dectin-2 gene. Although this promoter is of mouse origin and proven to be transcriptionally active in mouse DC, it is contemplated that it will function as a DC-specific promoter in human cells as well, as judged from previous studies demonstrating that the promoter for mouse immunoglobulin gene or mouse T cell receptor gene is also transcriptionally active in human B cells or human T cells, respectively. On the other hand, the inventors also believe that the dectin-related reagents will allow them to identify relevant promoters for human dectin-1 or human dectin-2 gene.

Although it remains unclear at this moment whether dectin-1 or dectin-2 proteins also play functional roles in DC-dependent activation of B cells directly, DC are now known to deliver B cell activation signals through "helper T cells", leading to immunoglobulin secretion. Therefore, it is conceivable that dectin-related reagents may also prove useful to upregulate as well as to downregulate the B cell/immunoglobulin-dependent arm of immunity. Methods described above to modulate T cell-mediated immunity may be used for this aim as well.

It is also contemplated that the dectin related agents described herein may be used to regulate the in vitro production of antibodies.

1. Dectin-Related Agents and Assays

The following reagents are included in the present invention as "Dectin-related reagents": a) DNA segments of dectin-1 or dectin-2, including the 5'- and 3'-flanking regions, b) RNA segments of sense or anti-sense strands of dectin-1 or dectin-2, including the truncated or mutated transcripts, c) dectin-1 or dectin-2 polypeptides or proteins, including the truncated or mutated forms and their biological equivalents, d) polyclonal or monoclonal antibodies against dectin-1 or dectin-2, e) XS52 and other cell lines of the XS series that express dectin-1 and dectin-2, f) vectors designed to produce dectin-1 or dectin-2 polypeptides or proteins, g) cell lines that are engineered to express dectin-1 or dectin-2, h) cell lines that are engineered to lack the expression of dectin-1 or dectin-2, i) animals that are engineered to overproduce dectin-1 or dectin-2, j) animals that are engineered to lack the expression of dectin-1 or dectin-2, k) other members of the dectin family of genes and their products which can be identified with the above reagents, l) relevant ligands of dectin-1 or dectin-2 which can be identified with above reagents, and m) 5'-flanking and 3'-flanking sequences of dectin-1 or dectin-2, including putative DC-specific promoter sequences.

The following assays that employ dectin-related reagents are also included in the present invention as "Dectin-related assays": a) assays to detect dectin-1 or dectin-2 DNA, including Southern blotting, genomic PCR™, colony and plaque hybridization, and slot blotting; b) assays to detect dectin-1 or dectin-2 RNA, including northern blotting, RT-PCR™, in situ hybridization, primer extension assay, and RNase protection assay; c) assays to detect dectin-1 or dectin-2 polypeptides or proteins, including ELISA, Western blotting, immunoprecipitation, radioimmuno-absorption and competition assays, and immunofluorescence and immunohistochemical stainings; and d) assays to search for reagents that modulate dectin-dependent DC-T cell interaction, including dectin binding assay, DC-induced T cell activation assay, DC-T cell adhesion assay, and assays to examine dectin-1 or dectin-2 expression Detailed methodologies for these assays will be described in the following sections.

2. Assays to Examine Dectin-1 and Dectin-2 at DNA Levels

Nucleotides of dectin-1 or dectin-2 (SEQ ID NO:1 or SEQ ID NO:3) or related nucleotides that exhibit significant homologies with or that contain portions of dectin-1 or dectin-2 will be used as probes to detect members of the dectin family of genes. The dectin family of genes is defined as genes that are detectable with at least one of these probes. For this purpose, standard assays, including Southern blotting, PCR™, colony and plaque hybridization, and slot blot hybridization will be employed under various conditions with different degrees of stringency as described previously. Specimens to be tested include cDNA libraries, genomic DNA, cDNA, and DNA fragments isolated from cells or tissues. These assays may be modified to detect selectively mutated dectin-1 or dectin-2 DNA. For this purpose, Southern blotting or PCR™ will be employed to detect or amplify the mutated DNA segments. These segments will then be sequenced to identify the mutated nucleotides. Alternatively, a combination of selected restriction enzymes will be employed to reveal molecular heterogeneity in Southern blotting. Moreover, these assays may be modified to detect selectively different domains or different portions of the dectin-1 or dectin-2 nucleotide sequences. For this aim, one may employ probes or primers for different portions of the nucleotide sequences. More sophisticated methods may be employed to screen point mutations. For example, it is contemplated that one may choose a PCR™-single-strand conformation polymorphism (PCR™-SSCP) analysis (Sarkar et al., 1995).

3. Assays to Examine Dectin-1 and Dectin-2 at RNA Levels

Nucleotides of dectin-1 or dectin-2 (SEQ ID NO:1 or SEQ ID NO:3) or related nucleotides that exhibit significant homologies with or that contain portions of with dectin-1 or dectin-2 will be used as probes to detect transcripts of the dectin-1 family of genes. For this purpose, standard assays, including northern blotting, RT-PCR™, in situ hybridization, primer extension assay and RNase protection assay will be employed under various conditions with different degrees of stringency as described previously. Specimens to be tested include total RNA and mRNA isolated from cells or tissues and cell and tissue samples themselves obtained from living animals or patients. These assays may be modified to detect selectively the transcripts for different domains or different isoforms. For this purpose, the inventors will employ probes or primers for different portions of the nucleotide sequences. In fact, the inventors have been able to identify several truncated transcripts of dectin-1 or dectin-2 by RT-PCR™ using a panel of different primer sets. These transcripts have been found to be produced by alternative splicing mechanisms. Similar methods using RT-PCR™ may be employed to identify other spliced variants and even other isoforms that are produced by other mechanisms. Alternatively, northern blotting may be used to detect selectively different isoforms. For this purpose, oligonucleotide probes will be constructed, each covering different portions of the nucleotide sequences. To defined the nucleotides that are deleted from the original sequence, RNase protection assays may be employed. Detection of mutated RNA is also included in the present invention. For this aim, RNA isolated from DC will be analyzed by northern blotting or RT-PCR™.

It is further contemplated that assays may be designed to detect selectively different RNA species. In fact, the inventors have been able to identify several truncated transcripts of dectin-1 or dectin-2 by RT-PCR™ using a panel of different primer sets. These transcripts have been found to be produced by alternative splicing mechanisms. Similar methods using RT-PCR™ may be employed to identify other spliced variants and even other isoforms that are produced by other mechanisms. Alternatively, northern blotting may be used to detect selectively different isoforms. For this purpose, oligonucleotide probes will be constructed, each covering different portions of the nucleotide sequences. To define the nucleotides that are deleted from the original sequence, RNase protection assays may be employed.

4. Assays to Examine Dectin-1 and Dectin-2 at Protein or Polypeptide Levels

Antibodies against dectin-1 or dectin-2 will be used to detect dectin-1 or dectin-2 proteins or polypeptides. For this purpose, standard assays, including ELISA, western blotting, immunoprecipitation, radioimmuno-absorption and radioimmuno-competition assays, and immunofluorescence and immunohistochemical stainings will be employed under various conditions with different degrees of specificity and sensitivity. Specimens to be tested include viable cells, whole cellular extracts, and different subcellular fractions of established cell lines, as well as cells, tissues, and body fluids isolated from living animals or patients. These assays may be modified to detect selectively different epitopes, domains, or isoforms of dectin-1 or dectin-2 polypeptides or proteins. For this purpose, the inventors will develop and employ a panel of MAb against different epitopes or domains. In this regard, the inventors have generated a panel of MAb against recombinant His-dectin-2 proteins (produced in $E.\ coli$). Rats were immunized with His-dectin-2 and hybridomas were screened in western blotting for their reactivity to His-dectin-1. Resulting MAb (MAD2-Rhi) recognize not only the His-dectin-1, but also native forms of dectin-2 proteins in the extract from XS52 DC. Although these MAb do not appear to distinguish different isoforms of dectin-2, it is practically feasible to develop domain-specific MAb against dectin-2 (or dectin-1) by immunization with synthetic peptides or recombinant proteins of a given domain.

5. Assays to Examine Dectin-1 and Dectin-2 at Functional Levels

Long-term DC lines expressing dectin-1 and dectin-2 (e.g., XS52, XS106, and other cell lines of the XS series), short-term DC cultures established from various tissues (e.g., blood, bone marrow, or spleen), or DC freshly isolated from various tissues (e.g., skin, blood, spleen, lymph nodes, thymus, or lung) will be employed as DC preparations. Long-term T cell lines and clones, T cell hybridomas, short-term T cell lines (e.g., Con A-blasts), or T cells isolated from various tissues (e.g., blood, spleen, lymph nodes, or thymus) either before or after immunization with particular antigens will be employed as T cell preparations. Soluble forms of dectin-1 or dectin-2 (e.g., His-tagged forms, GST-fusion proteins, or soluble isotypes) will be used as soluble dectin-1 or dectin-2.

An example of functional assays is the "dectin binding assay". The inventors have shown that His-tagged dectin-1, containing only the extracellular domains of dectin-1, does bind to the surface of both T cells freshly isolated from spleen and T cell lines (e.g., HDK-1 T cell clone and the 7–17 DETC line). Thus, it appears that extracellular domains of dectin-1 and presumably dectin-2 contain amino acid sequences that bind to the surface of T cells and that this binding serves as a relevant function of dectin-1 and presumably dectin-2. Test samples containing dectin-1 or dectin-2 may be examined directly for their binding capacity to T cells; the bound dectin-1 or dectin-2 will be measured by using antibodies against dectin-1 or dectin-2. Alternatively, samples may be examined for their capacity to compete with His-tagged dectin-1 or His-tagged dectin-2 (or other soluble forms) for the binding to T cells. In this case, His-tagged dectin-1 or His-tagged dectin-2 will be radiolabeled with $^{125}$I or $^{35}$S or labeled in other ways (e.g., fluorescence-labeled or biotinylated) and then examined for binding to the surface of splenic T cells or T cell lines in the presence or absence of each test sample. If the sample inhibits the binding of the labeled dectin-1 or dectin-2, it will indicate the competitive activity.

Another example for functional assays is the use of "DC-induced T cell activation assays". The inventors have shown that polyclonal antibodies raised against His-dectin-1 (containing the entire extracellular domains) (TAD 1-Rhi) inhibit completely DC-induced activation of T cells. Test samples may be tested in soluble forms for their capacity to inhibit DC-induced T cell activation. If the sample inhibit T cell activation, as assessed by proliferative responses or cytokine secretion by T cells, it will indicate that the sample contains functional active dectin-1 or dectin-2 polypeptides or proteins. Alternatively, dectin-1 or dectin-2 may be tested in immobilized forms. For this aim, dectin-1 or dectin-2 in test samples will be immobilized onto plastic surfaces by means of anti-dectin-1 or anti-dectin-2 antibodies and then examined for their capacity to induce T cell activation. If the sample induces T cell activation, as assessed by proliferative responses or cytokine secretion by T cells, it will indicate that the sample contains functionally active dectin-1 or dectin-2 polypeptides or proteins.

A third example for functional assays is the "DC-T cell adhesion assays". It was noted during studies that addition of polyclonal antibodies against dectin-1 (TAD1-Rhi) in DC-induced T cell activation assays results in significant inhibition of the formation of DC-T cell clusters. This, together with other data, suggest that dectin-1 and presumably dectin-2 mediate the physical binding of DC to responding T cells. The inventors will develop functional assays to test the ability of dectin-1 or dectin-2 in test samples to affect DC-T cell binding. Specifically, two assays will be employed: a) DC-T cell cluster formation is assessed visually under a microscope during DC-induced T cell activation assays; and b) radiolabeled T cells are examined for their adhesion onto DC that are immobilized on tissue culture plates. Non-DC populations transfected with dectin-1 or dectin-2 cDNA may serve as alternative substrates for T cell binding. Samples may be tested in soluble forms for their capacity to inhibit DC-T cell binding in both assays. The sample that inhibits DC-T cell binding will be considered to contain functionally active dectin-1 or dectin-2. Samples may be tested in immobilized forms; dectin-1 or dectin-2 in test samples will be immobilized onto tissue culture plates by means of anti-dectin-1 or anti-dectin-2 antibodies, and radiolabeled T cells will then be assessed for their adhesion to such substrates. The sample that promotes T cell adhesion will be considered to contain functionally active dectin-1 or dectin-2.

6. Assays to Search for Reagents that Modulate Dectin-Dependent DC-T Cell Interaction Finally, the dectin-related assays described above may also be used to search for molecules that inhibit dectin-dependent signaling cascades during DC-T cell interaction, comprising admixing a dectin-1 or dectin-2 composition with a population of T cells and a candidate substance and identifying a candidate substance that inhibits the interaction of dectin-1 or dectin-2 with the T cells. Preferably, the dectin-1 or dectin-2 of this method will be expressed on the surface of a DC. Alternatively, the composition comprising dectin-1 or dectin-2 may comprise engineered cells that express recombinant dectin-1 or dectin-2. In yet another embodiment, the dectin-1 or dectin-2 composition may comprise purified dectin-1 or dectin-2 operatively linked to a detectable label. The dectin-1 or dectin-2 composition may alternatively comprise a population of DC that express dectin-1 or dectin-2.

The first screening will be to determine whether candidate substances may affect the expression of dectin-1 or dectin-2 by DC. For this purpose, DC preparations (e.g., XS52 cells, mouse splenic DC, mouse Langerhans cells, human DC, or human Langerhans cells) will be treated with candidate substances either individually or in combination and then examined for dectin-1 or dectin-2 expression at the levels of mRNA, protein, and function. Alternatively, those candidate substances may be tested in vivo by administering into living animals. In this case, DC will be isolated from those mice after treatment and then examined in vitro for dectin-1 or dectin-2 expression, once again, at the levels of mRNA, protein, and function. In performing these assays, it will be important to also examine the effect(s) of candidate substances on the expression of different isoforms of dectin-1 or dectin-2.

The candidate substance that inhibits the interaction of dectin-1 or dectin-2 with T cells may be identified by inhibition of dectin-1 or dectin-2 binding to the T cells. Alternatively, the candidate substance that inhibits the interaction of dectin-1 or dectin-2 with T cells may be identified by inhibition of dectin-1 or dectin-2 mediated activation of T cells.

More specifically, the invention also provides a method for identifying an inhibitory agent, comprising the steps of:
 (a) admixing a first composition comprising a population of recombinant cells expressing dectin-1 or dectin-2 with a second composition comprising a population of T cells,
 (b) incubating the admixture with a candidate substance;
 (c) testing said admixture for T cell activation; and
 (d) identifying a candidate substance that inhibits the activation of T cells.

The invention further provides agents that inhibit the binding of dectin-1 or dectin-2 to T cells. Alternatively, the invention provides agents that inhibit dectin-1 or dectin-2-mediated activation of T cells. In preferred embodiments, the agent of the invention will be formulated in a pharmaceutical acceptable medium.

The present invention further provides a method for purifying T cells. Preferably, the method comprises the steps of:
 (a) preparing an immobilized dectin-1 or dectin-2 composition comprising a dectin-1 or dectin-2 protein or polypeptide linked to a solid support;
 (b) contacting said immobilized dectin-1 or dectin-2 composition with a test composition suspected of containing T cells under conditions effective to allow T cell binding to said dectin-1 or dectin-2;
 (c) removing unbound components from said test composition; and
 (d) releasing bound T cells from said immobilized dectin-1 or dectin-2 composition.

In still further embodiments, the present invention concerns a method for identifying new DC-T cell interaction inhibitory compounds, which may be termed as "candidate substances." It is contemplated that this screening technique will prove useful in the general identification of any compound that will serve the purpose of inhibiting T cell activation, preferably in response to DC.

It is further contemplated that useful compounds in this regard will in no way be limited to antibodies. In fact, it may prove to be the case that the most useful pharmacological compounds for identification through application of the screening assay will be non-peptidyl in nature and serve to inhibit the T cell activation process through a tight binding or other chemical interaction.

Candidate molecules may also be tested for their capacity to inhibit the binding of labeled dectin-1 or dectin-2 in soluble forms to the surface of T cells (in the dectin binding assay), to inhibit the adhesion of T cells to DC (in the DC-T cell adhesion assay). Alternatively, these molecules may be examined for their capacities to suppress or to enhance the expression of dectin-1 or dectin-2 by DC at mRNA or protein levels. For this aim, DC will be incubated with test samples and then examined for dectin-1 or dectin-2 expression by northern blotting, RT-PCR™, in situ hybridization, primer extension assay and RNase protection assay (at RNA levels) or by ELISA, western blotting, immunoprecipitation, radioimmuno-absorption and competition assays, and immunofluorescence and immunohistochemical stainings (at protein levels).

Candidate molecules may augment dectin-dependent DC-T cell interaction. To test this possibility, test samples will be added to the DC-induced T cell activation assay, the dectin-binding assay, or the DC-T cell adhesion assay. Samples that enhance the function of dectin-1 or dectin-2 in one of these assays will be considered to possess an immuno-augmentative property.

G. Other Members of the Dectin Family and Ligands of Dectin-1 or Dectin-2

1. Other Members of the Dectin Family

It is expected that there exists other molecules that share structural or functional properties with dectin-1 or dectin-2. For example, human equivalents have been identified for most, if not all, of the surface molecules that were originally discovered in mice. Moreover, the inventors have identified several isoforms of dectin-1 or dectin-2. Additionally, it is contemplated that dectin-1 and dectin-2 may not only form a heterodimeric structure, but may also form even more complex structures with other subunits. These molecules, including dectin-equivalents in other species, dectin isoforms, and dectin subunits, are designated as members of the dectin family and are included in the present invention. This is because the availability of dectin-related reagents and assays allows the inventors to identify those molecules that share structural or functional properties with dectin-1 or dectin-2. In fact, the inventors have identified and characterized several isoforms.

To identify human equivalents of dectin-1 and/or dectin-2, genomic PCR™ and RT-PCR™ amplification may be used. In these methods, human genomic DNA or cDNA will be amplified, under various conditions with different degrees of stringency, using primer sets designed on the basis of murine dectin-1 and dectin-2 nucleotide/amino acid sequences as described above. PCR™ products will then be cloned and sequenced. If they exhibit significant homologies to murine dectin-1 or dectin-2 at the level of either nucleotide or amino acid, these PCR™ products will be used to clone relevant cDNA from a cDNA library prepared from human dendritic cells or peripheral blood leukocytes.

To perform colony hybridization, a cDNA library prepared from human DC or peripheral blood leukocytes or a human genomic DNA library will be hybridized under various conditions with different degrees of stringency, with murine dectin-1 or dectin-2 cDNA or targeted fragments of these cDNA. Alternatively, these libraries may be hybridized with oligonucleotides synthesized based on the sequences of murine dectin-1 and dectin-2.

In fact, the inventors have been able to detect a human equivalent of dectin-2 by Southern blotting. In those studies, RNA isolated from human peripheral blood DC were converted into cDNA by using CapFinder® system (Clontech, Palo Alto, Calif.). The resulting DC-derived cDNA were then hybridized with a CRD sequence for murine dectin-1 (SEQ ID NO:9). In Southern blotting under a relatively low stringent condition (1 M NaCl, 30–45% formamide, 10% dextran sulfate, at 37° C.), this cDNA probe hybridized a 2.8 kb band, which most likely represent a human equivalent of dectin-2. These results indicate that murine dectin-1 and human dectin-1 show a nucleotide sequence homology that is high enough to be detectable with the nucleotide sequence of SEQ ID NO:9. These results validate that human equivalents of dectin-1 or dectin-2 are detectable with cDNA probes of mouse origin. By using RT-PCR™, the inventors have identified a 172 bp DNA fragment for human dectin-2 from human peripheral blood DC. This DNA fragment (SEQ ID NO:33) exhibits 71.5% similarity in nucleotide sequence to mouse dectin-2. Human dectin-2 also showed 63.2% similarity in amino acid sequence to mouse dectin-2. Moreover, this DNA fragment hybridized strongly a human dectin-2 mRNA in Northern blotting. Specifically, the inventors have detected 2.8 kb and 4.0 kb bands in human lymphoid tissues (e.g., peripheral blood mononuclear cells, spleen, and thymus), but not in non-lymphoid tissues (e.g., kidney, heart, muscle, liver, and brain).

It is contemplated that antibodies which recognize human DC will be useful in a number of ways. For example, antibodies that recognize human DC may be used to identify human equivalents of dectin-1 and dectin-2. More specifically, relevant proteins may be purified by immunoprecipitation and then sequenced. cDNA encoding human equivalents may then be cloned by PCR™ and/or colony hybridization using PCR™ products (amplified with primers designed from the amino acid sequences) or oligonucleotides.

Relevant ligands of murine dectin-1 and/or dectin-2 (see Example 7), may serve as molecular probes to identify human equivalents of dectin-1 and/or dectin-2. More specifically, soluble forms of ligands for murine dectin-1 and/or dectin-2 are first examined for their binding to the surface of human DC. If they show significant binding, an expression cDNA cloning strategy is employed, in which a non-DC line (which express no detectable dectin-1 or dectin-2) is transfected with a cDNA library prepared from human DC (or peripheral blood leukocytes). Transfectants that bind soluble ligands (in other words, expressing human equivalents of dectin-1 or dectin-2) are isolated by FACS or panning. This procedure will be repeated to identify the cDNA that encode human equivalents of dectin-1 and dectin-2.

2. Relevant Ligands for Dectin-1 or Dectin-2

It is contemplated that ligands for dectin-1 or dectin-2 can be identified by using dectin-related reagents and assays. For example, in an expression cloning strategy, one will first examine several different cell lines for their capacity to bind soluble forms of dectin-1 and dectin-2 (e.g., His-dectin-1 and His-dectin-2). A cell line that shows no significant binding will then be transfected with a cDNA library prepared from the HDK-1 T cell line, which shows significant binding. Transfectants that bind soluble dectin-1 and/or dectin-2 will then be isolated by FACS or panning. This procedure is repeated to identify the cDNA that encode relevant ligands of dectin-1 and/or dectin-2. Considering the possibility that dectin-1 and dectin-2 may increase their affinity following heterodimerization, dectin-1/dectin-2 complex will be used in some studies.

Mammalian cells transfected with dectin-1 and/or dectin-2 cDNA may be used to identify peptides that bind to dectin-1 and/or dectin-2. Specifically, *E. coli* expressing a random peptide display library (e.g., FliTrx™) will be screened for the binding to the above transfectants by panning. After several rounds of screening, positive clones will be sequenced. Full-length polypeptides will then be identified by colony hybridization of a T cell cDNA library using oligonucleotide or PCR™ primers synthesized based on the peptide sequence.

For an alternate, biochemical approach to isolating relevant ligands for dectin-1 or dectin-2, total cell extracts or membrane fractions prepared from a T cell line will be applied onto an affinity column conjugated with soluble dectin-1 and/or dectin-2. Molecules bound to the column (i.e., putative ligands) will then be eluted by changing the pH or washing with EDTA or carbohydrates. The eluents will be purified by conventional column chromatography and HPLC and then examined for amino acid sequences. cDNA encoding these ligands will be cloned by colony hybridization of a T cell cDNA library using oligonucleotide or PCR™ primers synthesized based on the revealed amino acid sequence.

H. Clinical and Subclinical Application of Dectin-Related Reagents and Assays

It is further contemplated that the dectin-1 and/or dectin-2 related agents described herein, i.e., dectin-1 and/or dectin-2 proteins or polypeptides, antibodies raised against such proteins or polypeptides, mutated, truncated or elongated forms of dectin-1 and/or dectin-2, antibodies raised against such forms, and cells engineered to overproduce or lack dectin-1 or dectin-2 may be used to suppress immunity. That is, they may be used for the treatment of autoimmune diseases, allergies, and other forms of hypersensitivity reactions.

In addition to the use of antibodies against dectin-1 and/or dectin-2 to block the function of these receptors or to kill DC, recombinant dectin-1 and/or dectin-2 may be used in soluble forms to suppress immunity. Further, soluble isoforms of native dectin-1 and/or dectin-2, peptides that correspond to the ligand-binding sites of dectin-1 and/or dectin-2, ligands in soluble form, or other reagents that inhibit the expression and function of dectin-1 and/or dectin-2 may be used to suppress immunity.

The inventors also contemplated the use of the dectin related agents described herein to examine the immunological functions of DC and/or T cells isolated from animals or human patients. For example, dectin-1 and/or dectin-2 transfectants may be used to measure the function of T cells, antibodies against dectin-1 and/or dectin-2 may be used to measure the numbers of DC as well as the expression and function of dectin-1 or dectin-2 on DC, or recombinant dectin-1 and/or dectin-2 proteins (e.g., His-dectin-1) may be used to measure the potential of T cells to be activated in a dectin-dependent manner.

1. Diagnostic Application

Dectin-related reagents and assays may be applicable clinically to diagnostic purposes. For example, to determine the number of dectin-1 or dectin-2 expressing DC, the amount of dectin-1 or dectin-2 proteins, or functional activities of dectin-1 or dectin-2 will provide important information with respect to the immunity of patients. Moreover, some patients exhibiting symptoms for immunodeficiency may have: a) dectin-1 or dectin-2 mutations, b) mutations in the relevant ligands of dectin-1 or dectin-2, c) overproduction of soluble isoforms of dectin-1 or dectin-2 (or dectin-ligands), or d) autoantibodies against dectin-1 or dectin-2.

As noted, it is contemplated that the antibodies of the invention will find utility as immunogens, e.g., in connection with vaccine development, as therapeutics in treating T cell-mediated inflammatory diseases, as positive controls in screening assays, purifying dectin-1 or dectin-2 molecules or DC, and in the recombinant cloning of dectin-like molecules. One evident utility of the dectin-related reagents is in immunoassays for the identification of DC and dectin-expressing cells in the tissues and the detection of different isoforms of dectin-1 or dectin-2 and autoantibodies against dectin-1 or dectin-2, as needed in diagnosis and prognostic monitoring.

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the anti-dectin-1 or anti-dectin-2 antibodies of the invention are immobilized onto a selected surface exhibiting protein affinity, such as a well in a polystyrene microtiter plate. Then, a test composition suspected of containing the dectin-1 or dectin-2 antigen, such as a clinical sample, is added to the wells. After binding and washing to remove non-specifically bound immune complexes, the bound dectin-1 or dectin-2 antigen may be detected. Detection is generally achieved by the addition of another anti-dectin-1 or anti-dectin-2 antibody that is linked to a detectable label. This type of ELISA is a "sandwich ELISA". Detection may also be achieved by the addition of a second anti-dectin-1 or anti-dectin-2 antibody, followed by the addition of a third antibody that has binding affinity for the second anti-dectin-1 or anti-dectin-2 antibody, with the third antibody being linked to a detectable label.

In another exemplary ELISA, the samples suspected of containing the dectin-1 or dectin-2 antigen are immobilized onto the well surface and then contacted with the anti-dectin-1 or anti-dectin-2 antibodies of the invention. After binding and washing to remove non-specifically bound immune complexes, the bound anti-dectin-1 or anti-dectin-2 antibodies are detected. Where the initial anti-dectin-1 or anti-dectin-2 antibodies are linked to a detectable label, the immune complexes may be detected directly. Again, the immune complexes may be detected using a second antibody that has binding affinity for the first anti-dectin-1 or anti-dectin-2 antibody, with the second antibody being linked to a detectable label.

Another ELISA in which the proteins or polypeptides are immobilized, involves the use of antibody competition in the detection. In this ELISA, labeled anti-dectin-1 or anti-dectin-2 antibodies are added to the wells, allowed to bind, and detected by means of their label. The amount of dectin-1 or dectin-2 antigen in an unknown sample is then determined by mixing the sample with the labeled anti-dectin-1 antibodies before or during incubation with coated wells. The presence of dectin-1 or dectin-2 antigen in the sample acts to reduce the amount of anti-peptide antibody available for binding to the well and thus reduces the ultimate signal. This is also appropriate for detecting anti-dectin-1 or anti-dectin-2 antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immune complexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control protein and/or clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gammaglobulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid (ABTS) and $H_2O_2$, in the case of peroxidase as the enzyme label. Quantification is then achieved by measuring the degree of color generation, e.g., using a visible spectra spectrophotometer.

In still further embodiments, the present invention concerns immunodetection methods for binding, purifying, removing, quantifying or otherwise generally detecting biological components. The dectin-1 or dectin-2 proteins or polypeptides of the present invention may be employed to detect antibodies having reactivity therewith, or, alternatively, antibodies prepared in accordance with the present invention, may be employed to detect dectin-1 or dectin-2 proteins or polypeptides. Other molecules which may be identified using the dectin-1 and/or dectin-2 related agents described herein include: ligands of dectin-1 and/or dectin-2, including carbohydrate determinants as well as peptide determinants; other members (subunits and isoforms) of the dectin family; molecules that are associated with dectins (e.g., co-receptors, subunits, signaling molecules, etc.); molecules that bind to the 5'- or 3'-flanking regions, as well as the coding sequences of dectin-1 and/or dectin-2 genes; and/or molecules that are found to regulate the expression and/or function of dectin-1 and/or dectin-2. The steps of various useful immunodetection methods have been described in the scientific literature, such as, e.g., Nakamura et al. (1987), incorporated herein by reference.

In general, the immunobinding methods include obtaining a sample suspected of containing a dectin-1 or dectin-2 protein, polypeptide or anti-dectin-1 or anti-dectin-2 antibody, and contacting the sample with an antibody or dectin-1 or dectin-2 protein or polypeptide in accordance with the present invention, as the case may be, under conditions effective to allow the formation of immunocomplexes.

These methods include methods for removing undesirable components from a given sample, as exemplified by removing viral or other contaminants from blood samples, removing environmental contaminants from water samples, and the like. In these instances, an antibody will most likely be used to remove an antigenic component from a sample. The antibody will preferably be linked to a solid support, such as in the form of a column matrix, and the sample suspected of containing the unwanted antigenic component will be applied to the immobilized antibody. A purged or purified sample may be obtained free from the unwanted antigen by collecting the sample from the column and leaving the antigen immunocomplexed to the immobilized antibody.

The immunobinding methods also include methods for detecting or quantifying the amount of a reactive component in a sample, which methods require the detection or quantification of any immune complexes formed during the binding process. Here, one would obtain a sample suspected of containing a dectin-1 or dectin-2 protein, polypeptide or anti-dectin-1 or anti-dectin-2 antibody, and contact the sample with an antibody or dectin-1 or dectin-2 protein or polypeptide, as the case may be, and then detect or quantify the amount of immune complexes formed under the specific conditions.

It is contemplated that in order to monitor the amounts and qualities of dectin-1 and/or dectin-2 in clinical samples (e.g., sera, cells, tissues, etc.), one may use antibodies against dectin-1 and/or dectin-2 (e.g., in ELISA, RIA, immunoblotting as described herein), recombinant dectin-1 and/or dectin-2 (e.g., to provide competition at the level of binding to T cells) or cDNA and/or oligonucleotides (e.g., in RT-PCR™ or northern blotting as described herein).

In terms of antigen detection, the biological sample analyzed may be any sample that is suspected of containing a dectin-1 or dectin-2 protein or polypeptide, such as a cryostat skin tissue section or specimen, a homogenized skin tissue extract, a Langerhans cell, a Langerhans cell membrane preparation, separated or purified forms of any of the above dectin-1 or dectin-2 containing compositions, or even any biological fluid that comes into contact with skin tissues, including serum, urine and even skin blister fluid. Samples of non-skin-origin may also be analyzed; they include sections from lymphoid or non-lymphoid tissues, blood, and biological fluids.

In terms of antibody detection, samples of biological fluids will be more appropriate, as exemplified by blood, serum, sputum, ear fluid, urine, ascites, semen, and even skin blister fluid. However, using tissue sections or samples from the target tissues is also contemplated.

Contacting the chosen biological sample with the protein, polypeptide or antibody under conditions effective and for a period of time sufficient to allow the formation of immune complexes (primary immune complexes) is generally a straightforward matter of adding the composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological or enzymatic tags or labels outlined above. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The dectin-1 or dectin-2 protein, polypeptide or antibody employed in the detection may itself be linked to a detectable label, wherein one would then detect this label, thereby allowing the amount of the primary immune complexes in the composition to be determined.

Alternatively, the first added component that becomes bound within the primary immune complexes may be detected by means of a second binding ligand that has binding affinity for the dectin-1 or dectin-2 protein, polypeptide or antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the dectin-1 or dectin-2 protein, polypeptide or antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present invention have evident utility in the diagnosis of conditions that are caused by or associated with immunodeficiency. These conditions or diseases include recurrent infections and recurrent or rapidly growing cancers. Conversely, these methods may also be used in the diagnosis of conditions or diseases that are caused by or associated with hyperimmune reactions. They include allergic reactions against environmental antigens (e.g., bronchial asthma, allergic rhinitis, urticaria, atopic dermatitis, and allergic contact dermatitis) and inflammatory diseases of autoimmune nature (e.g., lupus erythematosus, rheumatoid arthritis and psoriasis). Here, a biological or clinical sample suspected of containing dectin-1 or dectin-2 protein or polypeptide or antibody is used. However, these embodiments also have applications to non-clinical samples, such as in the titering of antigen or antibody samples, in the selection of hybridomas, and the like.

In the clinical diagnosis or monitoring of patients with symptoms associated with immunodeficiency, the detection of soluble forms of dectin-1 or dectin-2 proteins or autoantibodies against dectin-1 or dectin-2, or an increase in the levels of such molecule, in comparison to the levels in a corresponding biological sample is indicative of dysfunction of dectin-mediated T cell activation pathway. Those patients may also exhibit abnormality in terms of the profile of dectin-1 or dectin-2 isoforms expressed on their DC. They may express predominantly the isoforms that function as natural inhibitors of full-length dectin-1 or dectin-2. On the other hand, detection of abnormally high levels of dectin-1 or dectin-2 on the surface of DC in patients with hyperimmune symptoms is indicative of hyperfunction of dectin-mediated T cell activation pathway.

It is further contemplated to be within the scope of the invention to search for dectin mutations in patients with immunological abnormalities. For example, antibodies, cDNA and oligonucleotides, and functional assays may be used. To search for genetic mutation, DNA isolated from patients will be first screened by Southern blotting or PCR™ for dectin-1 or dectin-2. Likewise, RNA isolated from peripheral blood DC will be examined by northern blotting or RT-PCR™. If patients exhibit dectin-1 or dectin-2 bands of different sizes or no detectable bands, this will indicate the genetic mutation. On the other hand, this screening, which can be routinely and rapidly performed, will not allow one to identify point mutations. Point mutations may be identified by sequencing the cDNA isolated from patients. More sophisticated methods may be employed to screen point mutations. For example, it is contemplated that one may choose a PCR™-single-strand conformation polymorphism (PCR™-SSCP) analysis (Sarkar et al., 1995).

To assess the mutation at the level of proteins, DC isolated from peripheral blood or other tissues will be examined in immunofluorescence staining with a panel of MAb each of which recognizes a different epitope of the dectin-1 or dectin-2 proteins. If one or more of these MAb fail to recognize the DC isolated from a patient, this will indicate that the respective epitopes of domains of dectin-1 or dectin-2 are mutated or deleted in the patient. Alternatively, DC isolated from patients may be examined by western blotting with polyclonal antibodies; immunoreactive bands that migrate differently from those of healthy individuals indicate abnormality at protein levels. To search for functional abnormality, dectin-1 or dectin-2 proteins will be purified from patients and then examined for biological activities by measuring the ability to inhibit the binding of His-dectin-1 or His-dectin-2 to the surface of T cells (in binding assays), to block DC-induced activation of T cells (in antigen presentation assay) or to block the binding of T cells DC (in cell adhesion assays). These and other related assays may lead to the identification of significant mutation of dectin-1 or dectin-2 in patients exhibiting immunological abnormality. Moreover, these assays may reveal a heterogeneity in terms of genetic susceptibility to hyperimmune or hypoimmune reactions to environmental or intrinsic antigens. This, in turn, may serve as a useful marker to predict relative susceptibility of individuals to several immune-controlled disorders, such as autoimmune diseases, allergic diseases, infectious diseases, and even cancers.

Autoantibodies against dectin-1 or dectin-2 may be present in detectable levels. Such autoantibodies may be detected by ELISA using relevant antibodies that recognize dectin-1 or dectin-2 proteins or polypeptides.

The present investors also contemplate that patients may generate autoreactive T cells against dectin-1 or dectin-2. The presence of such autoreactive T cells may be examined by testing the T cells isolated from patients (e.g., blood, lymph nodes, spleen, or thymus) for their responsiveness to purified dectin-1 or dectin-2 or to cells expressing dectin-1 or dectin-2.

2. Preventative/Therapeutic Application to Downregulate Immunity

As discussed above, dectin-related reagents may be used to suppress T cell-mediated immunity. An example is the use of antibodies against dectin-1 or dectin-2. In fact, the inventors have been able to inhibit nearly completely DC-induced activation of T cells in vitro with polyclonal antibodies against dectin-1. Another example is the use of soluble forms of dectin-1 or dectin-2. In this regard, DC are known to express CD80 and CD86 molecules, which bind to their ligands, CD28 and CTLA-4, expressed on T cells. The ligation of CD80/CD86 (on DC) with CD28/CTLA-4 (on T cells) is required for DC-dependent, full activation of T cells. This ligation has been blocked relatively effectively by MAb against CD80 or CD86 and even more completely by CTLA-4-Ig fusion proteins that contain the extracellular domain of CTLA-4. CTLA4-Ig fusion proteins have been used successfully to inhibit DC-dependent activation of T cells in vitro. Moreover, injection of the same preparations into study animals resulted in prevention of several immune reactions, including autoimmune diseases and hypersensitivity diseases. Similar inhibition has also been achieved with CD80-Ig or CD86-Ig fusion proteins. Based on these previous observations, it is expected that extracellular domains of dectin-1 or dectin-2, when administered in soluble forms, will exhibit beneficial effects to prevent or even treat immunological disorders. The present invention also includes the use of soluble forms of dectin-ligands. These approaches are expected to block DC-induced activation of T cells.

Another important consequence of interfering with dectin-dependent T cell activation cascade is the induction of clonal anergy. In this regard, blocking of the CD80/CD86-dependent cascade leads not only to a failure of T cell activation, but also to unresponsiveness of the T cells to the same antigen, a state termed clonal anergy. From the viewpoint that the CD80/CD86 cascade and the dectin-dependent cascade are both required for T cell activation, it is expected that blocking of the dectin-dependent signaling also induce clonal anergy. If this is correct, it will then be practically feasible to induce clonal anergy in T cell populations that are otherwise reactive to unwanted antigens (e.g., autoantigens or environmental antigens), thereby treating autoimmune diseases or hypersensitivity reactions. One approach to this aim is the use of anti-dectin-1 or dectin-2 antibodies or the antisense oligonucleotides for dectin-1 or dectin-2. DC purified from patients will be first treated with anti-dectin-1 or dectin-1 antibodies or with the antisense nucleotides. These DC, which express reduced amounts of functional dectin-1 or dectin-2 on their surfaces, will then be pulsed with the targeted antigen at a protein level or be transfected with cDNA encoding such antigen. These engineered DC, expressing reduced dectin-1 or dectin-2 and carrying the targeted antigen, will be injected back to the same patients. Using this method, one can target clonal anergy to those T cells that are reactive to the unwanted antigen. Another important aspect in this invention is the identification of a promoter for the dectin-2 gene. This DNA fragment isolated from 5'-flanking regions of the dectin-2 genomic DNA is transcriptionally active in DC, but not in other cell types (FIG. 5B). Therefore, DNA sequences in this fragment (SEQ ID NO:34) may be used to drive the transcription of exogenous DNA in a DC-specific manner. One obvious utility for such strategy (DC-targeted DNA vaccines) is to augment immune responses against infectious pathogens or cancers. Another utility is to suppress or downregulate the immune reactions. For example, one may treat human patients who are hypersensitive to a given antigen by replacing the peptides derived from the pathogenic antigen on MHC class I or class II molecules with unrelated, non-pathogenic peptides that bind to the MHC molecules with higher affinities. More specifically, patients will be administered with a construct that contains dectin-1 or dectin-2 promoter in the upstream of the cDNA encoding such non-pathogenic peptides. Such a construct will then be transcribed and translated only within DC, thereby replacing the pathogenic peptides on their MHC molecules with non-pathogenic peptides.

In still further embodiments, the present invention is concerned with a method of inhibiting a T cell activation process which includes subjecting the T cells to an effective concentration of a dectin-1 or dectin-2 inhibitor such as one of the family of positive candidate substances discussed above, but not limited to antibodies, including a soluble form of dectin-1 or dectin-2 or with a candidate substance identified in accordance with the candidate screening assay embodiments. This is, of course, an important aspect of the invention in that it is believed that by inhibiting the T cell activation process, one will be enabled to treat various aspects of disease, such as T cell-mediated inflammatory diseases. It is believed that the use of such inhibitors to block DC or dectin interaction with T cells will serve to treat patients with conditions or diseases caused by or associated with hyperimmunity and may be useful by themselves or in conjunction with other anti-inflammatory, anti-allergy, etc. therapies, including glucocorticoids, cyclosporin A, antihistamines and the like.

Aqueous compositions of the present invention comprise an effective amount of the dectin-related agents, such as anti-dectin-1 monoclonal antibodies dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The active compounds will generally be formulated for parenteral administration, e.g., formulated for injection via the intravenous, intramuscular, sub-cutaneous, intralesional, intranasal, oral or even intraperitoneal routes. The preparation of an aqueous composition that contains a dectin-1 or dectin-2 antibody as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that syringability adequate for injection exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

A dectin-1 or dectin-2 protein or polypeptide or antibodies against dectin-1 or dectin-2 can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. This is envisioned to have particular utility in severe allergic reactions such as in the case of bee stings or insect bites. In this regard, the use of DMSO as solvent is preferred as this will result in extremely rapid penetration, delivering high concentrations of the active dectin-1 or dectin-2 proteins, polypeptides or agents to a small area.

Upon formulation, solutions will be administered in a manner compatible with the dosage formulation and in such amount as is therapeutically effective. The formulations are administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like.

The use of sterile formulations, such as saline-based washes, by surgeons, physicians or health care workers to cleanse a particular area in the operating field may also be particularly useful.

Additional formulations which are suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%–2%.

3. Preventative/Therapeutic Application to Upregulate Immunity

The present invention is applicable not only to prevent T cell activation, thereby suppressing immune reactions, but also to augment immune reactions, thus providing various therapeutic and immunogenic compositions for use in both passive and active immunization embodiments. As such, the contemplated compositions may be used to augment immunity, that is, they may be used for vaccination against infectious pathogens and other harmful antigens and for the treatment of infectious diseases and cancers.

The invention thus provides methods of generating an immune response, which methods generally comprise administering to an animal, including a human subject, a pharmaceutically acceptable composition comprising an immunologically effective amount of a composition comprising dectin-1- or dectin-2-expressing cells or compounds or molecules that upregulate dectin-dependent T cell activation pathways.

Immunogenic compositions suitable for use in generating an effective immune response, such as in vaccination, will generally include cells engineered to express dectin-1 or dectin-2 or dectin-1 or dectin-2 "adjuvants". As used herein, dectin-1 or dectin-2 "adjuvants" are defined as reagents or compounds that augment dectin-dependent T cell activation cascades. Dectin adjuvants may be identified by one of the dectin-related reagents or assays. For example, chemicals that augment the expression of dectin-1 or dectin-2 by DC are suitable candidates. Other compositions contemplated for use to augment immunity as described above include XS52 cells or their equivalents established from human tissues, or transfectants expressing dectin-1 and/or dectin-2 cDNA.

Preferably the "adjuvant" material is extensively dialyzed to remove undesired small molecular weight molecules and/or lyophilized for more ready formulation into a desired vehicle.

By "immunologically effective amount" is meant an amount of a dectin-1 or dectin-2 expressing cell composition or adjuvant that is capable of stimulating an immune response in the recipient animal. This includes both the generation of an antibody response (B cell response), and/or the stimulation of a cytotoxic or helper immune response (T cell response). The generation of such an immune response will have utility in both the production of useful bioreagents, e.g., helper T cells, CTLs and, more particularly, reactive antibodies, for use in diagnostic embodiments, and will also have utility in various prophylactic or therapeutic embodiments.

Accordingly, although these methods for the stimulation of an immune response include vaccination regimens designed to prevent or lessen significant T cell-mediated inflammatory disease, and treatment regimens that may lessen the severity or duration of any infection/disease, it will be understood that achieving either of these end results is not necessary for practicing these aspects of the invention. Moreover, it is expected that dectin adjuvants may prove useful in the prevention or treatment of infectious diseases and cancers.

The invention thus provides methods for obtaining an antibody or a T cell by administering to an animal an immunologically effective amount of a dectin-1 or dectin-2 expressing cell composition or adjuvant and obtaining a sample from the animal to provide the desired antibody or T cell. Blood samples are appropriate for obtaining polyclonal antibodies and less purified T cell compositions, whereas spleen cells or lymph node cells may be obtained to provide monoclonal antibodies and more purified T cell compositions. The methods for generating purified antibodies and T cells from such samples are well known to those of skill in the art.

Immunoformulations of this invention, whether intended for vaccination, treatment, or for the generation of antibodies useful in dectin-1 or dectin-2 detection, may comprise cells engineered to express whole dectin-1 or dectin-2 proteins or antigenic polypeptide fragments from these proteins. As such, antigenic functional equivalents of the proteins and polypeptides described herein also fall within the scope of the present invention. An "antigenically functional equivalent" protein or polypeptide is one that incorporates an epitope that is immunologically cross-reactive with one or more epitopes of the dectin-1 or dectin-2 proteins. Antigenically functional equivalents, or epitopic sequences, may be first designed or predicted and then tested, or may be directly tested for cross-reactivity.

The identification or design of dectin-1 or dectin-2 epitopes, and/or their functional equivalents, suitable for use in immunoformulations, vaccines, or as antigens (e.g., for use in detection protocols), is a relatively straightforward matter.

It is proposed that the use of cells engineered to express shorter antigenic polypeptides, e.g., about 15–30 amino acids in length, that incorporate epitopes of the selected dectin-1 or dectin-2 protein will provide advantages in certain circumstances, for example, in the preparation of vaccines or in immunologic detection assays. Exemplary advantages include the ease of preparation and purification, the relatively low cost and improved reproducibility of production, and advantageous biodistribution.

The preparation of immunotherapeutic formulations that contain polypeptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference.

Typically, such formulations are prepared as injectables, either as liquid solutions or suspensions, or are provided as solid forms suitable for later solution or suspension in liquid, prior to injection. The preparation may also be emulsified.

The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

The immunoformulations may be conventionally administered parenterally, by injection, for example, either subcutaneously or intramuscularly. Additional formulations which are suitable for other modes of administration include suppositories and, in some cases, oral formulations. The dosage of the composition given will likely depend on the route of administration.

The formulations are administered in a manner and at dosage amounts that are therapeutically effective, i.e., in an amount sufficient to stimulate an immune response in an the animal. The quantity to be administered depends on the subject to be treated, including, e.g., the size of the host, the capacity of the individual's immune system to synthesize antibodies, and the degree of protection or clearance desired. Precise amounts of active ingredient required to be administered depend on the judgment of the practitioner. However, suitable dosage ranges are of the order of 1–1000 μg active ingredient per vaccination.

Suitable regimens for initial administration and booster shots are also variable, but are typified by an initial administration followed by subsequent inoculations or other administrations. Adjuvants can also be employed, including the use of agents such as aluminum hydroxide or phosphate (alum), commonly used as 0.05 to 0.1 percent solution in phosphate buffered saline; admixtures of synthetic polymers of sugars (Carbopol), used as 0.25 percent solution; aggregation of the protein in the vaccine by heat treatment with temperatures ranging between 70° to 101° C. for 30 second to 2 minute periods respectively.

Aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles, such as mannide mono-oleate (Aracel A), or emulsion with 20 percent solution of a perfluorocarbon (Fluosol-DA) used as a block substitute may also be employed.

In many instances, where a preventative regimen is used, it will be desirable to have multiple administrations of the formulations, such as three, four, up to and including about six or so. These administrations or "vaccinations" will normally be at from two to twelve week intervals, more usually from three to five week intervals. Periodic boosters at intervals of 1–5 years, usually three years, will be desirable to maintain protective levels of the antibodies.

The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

As these polypeptides are thought to be particularly suitable for the inhibition of pulmonary inflammation, such as occurs in severe allergic reaction, a suitable treatment method for this disorder will be described. For the treatment of allergic rhinitis or bronchial asthma, one may use nasal solutions or sprays, aerosols or inhalants. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Inhalations and inhalants are pharmaceutical preparations designed for delivering a drug or compound into the respiratory tree of a patient. A vapor or mist is administered and reaches the affected area to give relief from symptoms of bronchial and nasal congestion. Inhalations may be administered by the nasal or oral respiratory routes. The administration of inhalation solutions is only effective if the droplets are sufficiently fine and uniform in size so that the mist reaches the bronchioles.

Another group of products, also known as inhalations, and sometimes called insufflations, consists of finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered does of the inhalation is propelled into the respiratory tract of the patient.

Particle size is of major importance in the administration of this type of preparation. It has been reported that the optimum particle size for penetration into the pulmonary cavity is of the order of 0.5 to 7 mm. Fine mists are produced by pressurized aerosols and hence their use in considered advantageous.

The inhalation of one, or a combination, of the dectin antibodies/polypeptides described in this application is contemplated to be capable of attenuating inflammation in ARDS. The range of doses to be administered by aerosol is estimated to be in the range of about 1 to about 100 mg.

The inventors also contemplate that the agents described herein may be used to upregulate as well as to downregulate T cell-mediated immunity in vivo. To Lipregulate immunity, dectin-1 or dectin-2 will be introduced into individuals by means of cDNA transfection. For example, DC purified from a patient may be engineered to overexpress dectin-1 or dectin-2 proteins by transfection with respective cDNA that is driven by a strong promoter. These transfectants will then be injected back to the same patient. If it is desired to target a certain antigen, those DC expressing high levels of dectin-1 or dectin-2 will be labeled with such an antigen at a protein level (by pulsing with antigen in vitro) or at a DNA level (by cotransfecting with a cDNA encoding the desired antigen).

Another important aspect in this invention is the identification of a promoter for the dectin-2 gene. This DNA fragment isolated from 5'-flanking regions of the dectin-2 genomic DNA has been proven to be transcriptionally active in DC, but not in other cell types (FIG. 5B). Therefore, DNA sequences in this fragment (SEQ ID NO:34) or a putative promoter for the dectin-1 gene may be used to drive the transcription of exogenous DNA in a DC-specific manner. One obvious utility for such strategy (DC-targeted DNA vaccines) is to augment immune responses against infectious pathogens or cancers. For this aim, the inventors will design constructs that contain the putative dectin-1 or dectin-2 promoter sequences in the upstream of the cDNA encoding relevant antigens in viruses, bacteria, or parasites or cDNA encoding tumor associated antigens. It is also feasible to construct an entire cDNA library from infectious microorganisms or cancer cells under the control of dectin-1 or dectin-2 promoter. Such constructs will be administered into animals (including human patients) through injections, gene gun, or viral vectors.

Dectin-related reagents may also be useful for the isolation of DC. For example, antibodies against dectin-1 or dectin-2 or ligands of dectin-1 or dectin-2 may be employed for their purification by means of fluorescence activated cell sorter (FACS) or panning. The same reagents may be used to deplete DC.

Another example for enhancing T cell-mediated immunity is the use of dectin-1 or dectin-2 promoters to target the expression of the gene to DC in the genetic immunization protocols. It is now feasible to deliver certain genes into living animals (including humans) by injecting DNA directly in a naked form or by delivering metal particles coated with DNA using high pressure apparatus ("gene guns"). This method has been used successfully to induce protective immunity against infectious pathogens or cancer development. However, it remains unknown which cell types incorporate the DNA, express the protein, and present its antigenic fragments to effector T cells. The present inventors have isolated a putative promoter region of the dectin-2 gene. This 3.2 kb DNA fragment did drive significant transcription of the luciferase gene in the XS DC lines, but not in NS fibroblast lines. These observations suggest that dectin-2 promoters are transcriptionally active only in DC, thus, forming both technical and conceptual basis for targeting gene expression to DC, i.e., delivering foreign genes selectively into DC by using promoter sequences of dectin-1 or dectin-2. Using this method, one can introduce cDNA encoding antigenic polypeptides of infectious pathogens or tumor cells (or even the entire cDNA library) selectively into DC in order to initiate protective immunity. One major advantage for the DC-targeted, genetic vaccination is that it will prevent the induction of tolerance, an event that is frequently inducible when the antigen is presented by non-professional antigen presenting cells in the absence of required co-stimulatory signals.

The inventors have identified DC-specific promoter in the 5'-flanking regions of dectin-2 gene. Although this promoter is of mouse origin and proven to be transcriptionally active in mouse DC, it is contemplated that it will also function as a DC-specific promoter in human cells. In this regard, it is known that the promoters for mouse immunoglobulin gene or mouse T cell receptor gene are also transcriptionally active in human B cells or human T cells, respectively. On the other hand, if human promoters are preferred for clinical use, it will be feasible to identify human promoters for dectin-1 or dectin-2 gene by using dectin-related reagents.

Another example for enhancing T cell-mediated immunity is the use of antibodies against dectin-1 or dectin-2 (or of ligands of dectin-1 or dectin-2) to absorb naturally occurring antagonists of dectin-1 or dectin-2. For example, the inventors have identified a soluble form of dectin-2 isoform, an isoform that may function as an antagonist. Therefore, it is contemplated that some patients with immunodeficiency may overproduce antagonists of dectin-1 or dectin-2. Such antagonists may be removed from blood circulation or other body fluids by using antibodies against dectin-1 or dectin-2 that are immobilized onto a solid phase (e.g., using protein A or protein G sepharose beads). Similar absorption may be achieved by using ligands of dectin-1 or dectin-2. As described previously, some patients may have circulating autoantibodies against dectin-1 or dectin-2. This form of antagonist may be removed by using recombinant dectin-1 or dectin-2 (e.g., His-dectin-1 or His-dectin-2) that are immobilized onto a solid phase (e.g., nickel-conjugated beads).

4. Pharmacological Application to Search for Reagents that Modulate Dectin-Dependent DC-T cell Interaction In still further embodiments, the present invention concerns a method for identifying new DC-T cell interaction inhibitory compounds, which may be termed as "candidate substances." It is contemplated that this screening technique will prove useful in the general identification of any compound that will serve the purpose of inhibiting T cell activation, preferably in response to DC.

It is further contemplated that useful compounds in this regard will in no way be limited to antibodies. In fact, it may prove to be the case that the most useful pharmacological compounds for identification through application of the screening assay will be non-peptidyl in nature and serve to inhibit the T cell activation process through a tight binding or other chemical interaction.

Accordingly, in screening assays to identify pharmaceutical agents which disrupt T cell activation, it is proposed that compounds isolated from natural sources, such as animals, bacteria, fungi, plant sources, including leaves and bark, and marine samples (as taught in Flam, 1994) may be assayed for the presence of potentially useful pharmaceutical agents. It will be understood that the pharmaceutical agents to be screened could also be derived from chemical compositions or man-made compounds.

In important aspects, the candidate substances may be preferred, e.g., anti-dectin-1 antibodies or anti-dectin-2 antibodies, including polyclonal and monoclonal antibodies; protein and/or polypeptide compositions. The suspected agents could also include proteins and polypeptides, such as those derived from recombinant DNA technology or by other means, including polypeptide synthesis. The active compounds may include fragments or parts of naturally-occurring compounds or may be only found as active combinations of known compounds which are otherwise inactive.

One may choose to determine whether candidate substances may affect the expression of dectin-1 or dectin-2 by DC. For this purpose, DC preparations (e.g., XS52 cells, mouse splenic DC, mouse Langerhans cells, human DC, or human Langerhans cells) will be treated with candidate substances either individually or in combination and then examined for dectin-1 or dectin-2 expression at the levels of mRNA, protein, and function. Alternatively, those candidate substances may be tested in vivo by administering into living animals. In this case, DC will be isolated from those mice after treatment and then examined in vitro for dectin-1 or dectin-2 expression, once again, at the levels of mRNA, protein, and function. In performing these assays, it will be important to also examine the effect(s) of candidate substances on the expression of different isoforms of dectin-1 or dectin-2.

In these embodiments, the present invention is directed to a method for determining the ability of a candidate substance to inhibit the T cell activation process, the method including generally the steps of:

(a) admixing a first composition comprising a population of recombinant cells expressing dectin-1 or dectin-2 with a second composition comprising a population of T cells (and relevant antigen if required);

(b) incubating the admixture with a candidate substance;

(c) testing said admixture for DC-induce T cell activation; and (d) identifying a candidate substance that inhibits the activation of T cells.

Figure 4A:
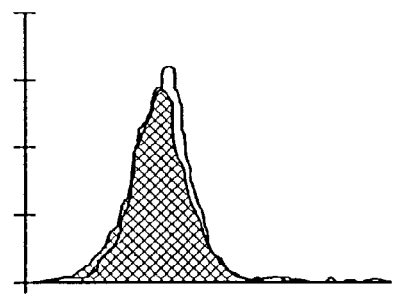
FIG. 4A, FIG. 4B, FIG. 4C. Functional role of dectin-1. Splenic T cells freshly isolated from naive BALB/c mice were incubated in the presence or absence of recombinant His-dectin-1 and then incubated with mAb against the His tag (filled histograms) or an isotype-matched control mouse IgG (open histograms).
Figure 4B:
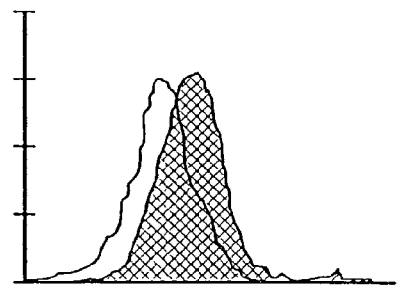

To identify a candidate substance, including a monoclonal antibody capable of inhibiting T cell activation, one would first obtain a dectin-1 or dectin-2 composition that is capable of activating T cells. For example, the inventors have shown that the His-dectin-1 fusion protein showed significant binding to splenic T cells freshly isolated from BALB/c mice, as revealed with the anti-His tag MAb (FIG. 4A). This staining, albeit relatively modest in intensity, was reproducible and specific. No staining was observed with an isotype matched control IgG or in the absence of His-dectin-1. This fusion protein also showed a modest degree of binding to the CD4+ T cell clone HDK-1 (FIG. 4B). Importantly, a control His-tagged protein, dehydrofolate reductase (DHFR), failed to show any binding, thus, establishing specificity. These results indicate that the extracellular domain of dectin-1, at least in soluble forms, bind to the surface of T cells.

Naturally, one would measure or determine the T cell activation capacity of the dectin-1 or dectin-2 composition in the absence of the added candidate substance. One would then add the candidate substance to the dectin-1 or dectin-2 composition and re-determine the ability of the dectin-1 or dectin-2 composition to activate T cells in the presence of the candidate substance. A candidate substance which reduces the T cell activation capacity of the dectin-1 or dectin-2 composition relative to the activity in its absence is indicative of a candidate substance with inhibitory capability.

The candidate screening assay is quite uncomplicated to set up and perform, and is related in many ways to the assay discussed above for determining protein or polypeptide activity. Thus, after obtaining a relatively purified preparation of the protein or polypeptide, either from native or recombinant sources, one will desire to admix a candidate substance with the protein preparation, preferably under conditions which would allow the protein to perform its T cell activation function but for inclusion of an inhibitory substance. Thus, for example, one will typically desire to include within the admixture an amount of a known T cell inhibitor, such as CTLA-4. As discussed previously, ligation of CD80/CD86 (on DC) with CD28/CTLA-4 (on T cells) is required for DC-dependent, full activation of T cells. This ligation has been blocked almost completely by CTLA-4-Ig fusion proteins that contain the extracellular domain of CTLA-4. It is important to note that CTLA-4-Ig fusion proteins not only inhibit DC-dependent activation of T cells in vitro, but they also prevent in animal levels several immune reactions, including autoimmune diseases and hypersensitivity diseases. In this fashion, one can measure the ability of the candidate substance to reduce T cell activation capacity relatively in the presence of the candidate substance.

Figure 4C:
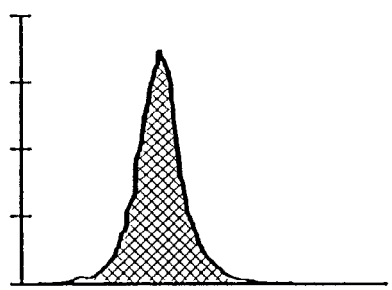
Figure 4D:
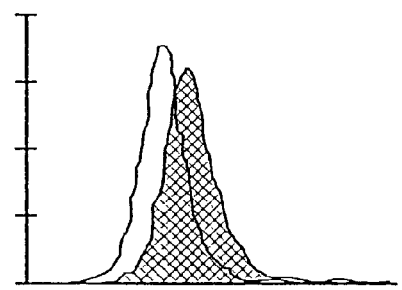
FIG. 4D shows the CD4$^+$ HDK-1 T cell clone labeled with His-dectin-1 and stained with anti-His tag or control IgG.
Figure 4E:
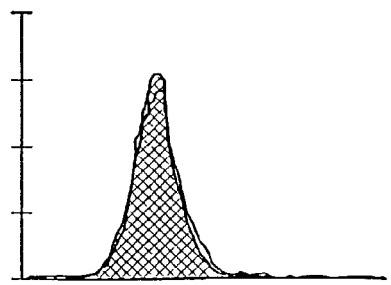
FIG. 4E shows the CD4$^+$ HDK-1 T cell clone labeled with His-DHFR and stained with anti-His tag or control IgG.
Figure 4F:
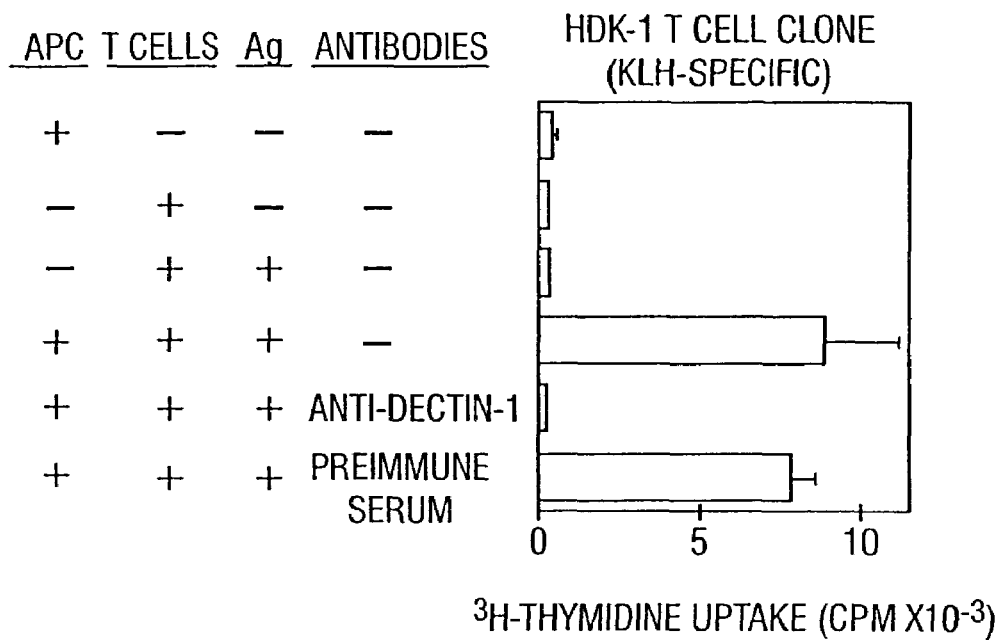
FIG. 4F, FIG. 4G, FIG. 4H, and FIG. 4I. Rat antiserum against His-dectin-1 (TAD1-Rhi) or preimmune serum was examined for its effect on antigen presentation by DC.
Figure 4G:
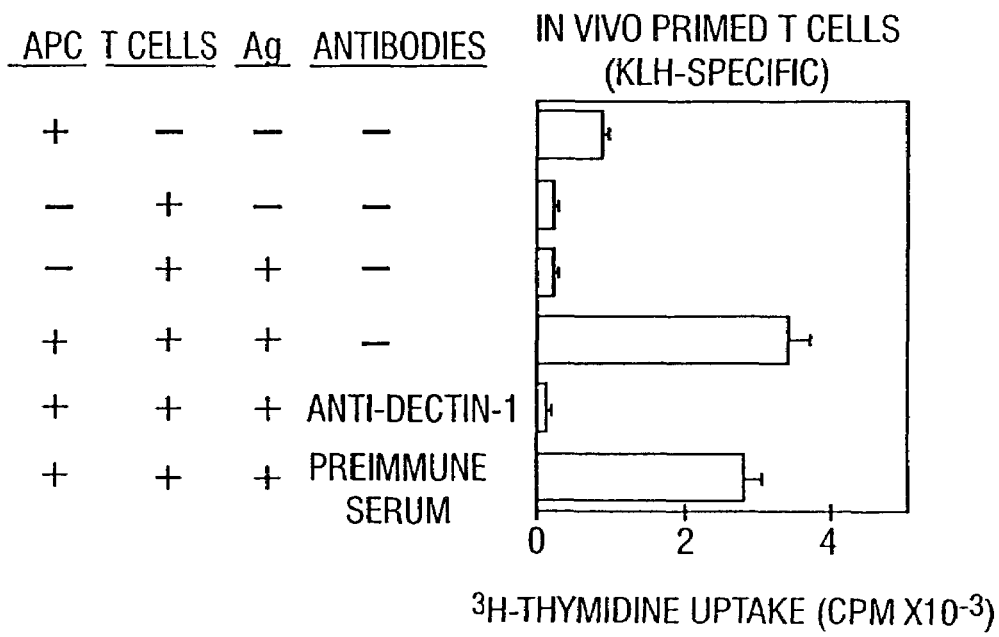
Figure 4H:
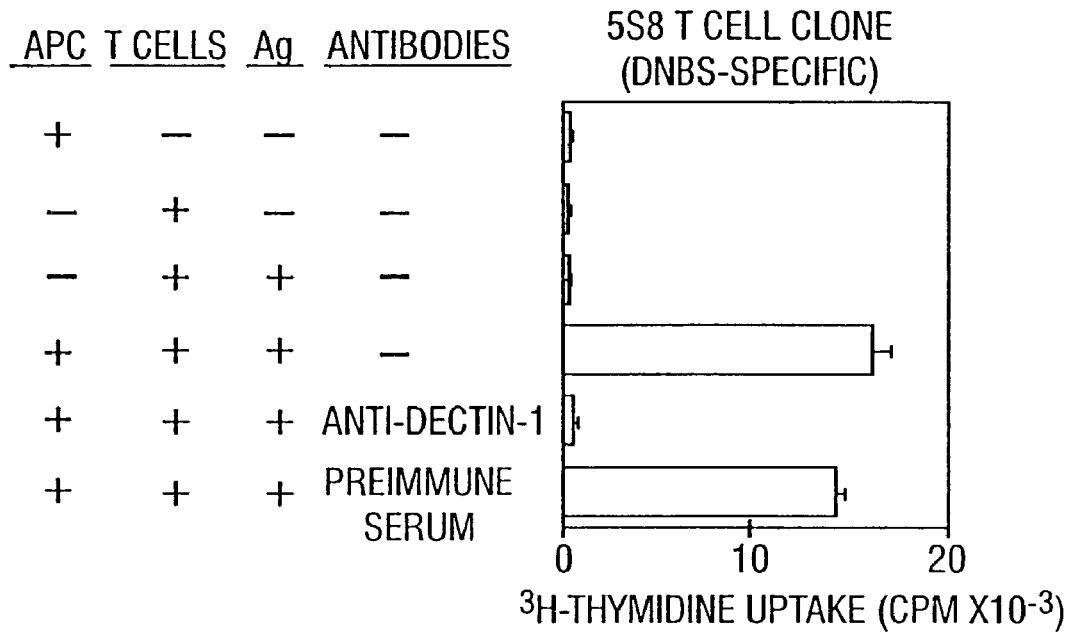
Figure 4I:
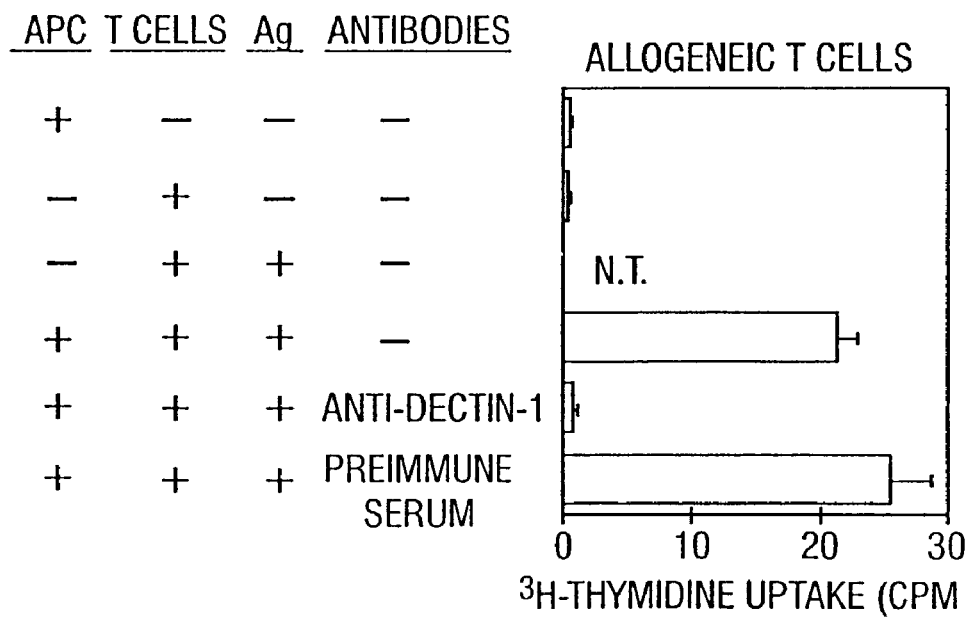
Figure 4J:
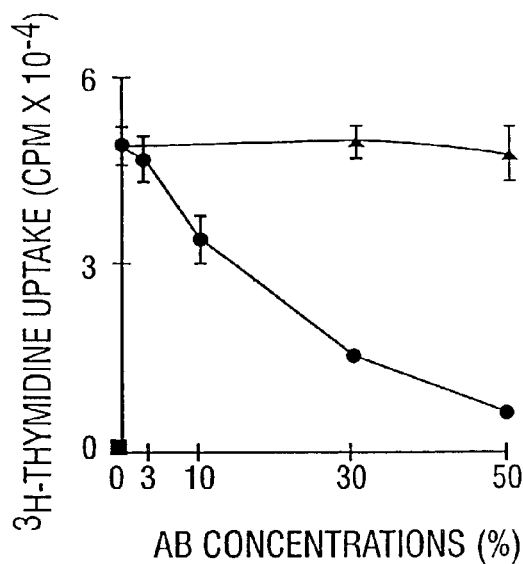
FIG. 4J. Anti-dectin-1 mAb 2E5 (circles) or isotype-matched control mAb (triangles) was examined for its effect on DC-dependent activation of allogeneic T cells. A baseline level of T cell proliferation in the absence of DC is indicated with a square. Data shown are the mean±SD (n=3) of $^3$H-thymidine, representing at least three independent studies.
Figure 4K:
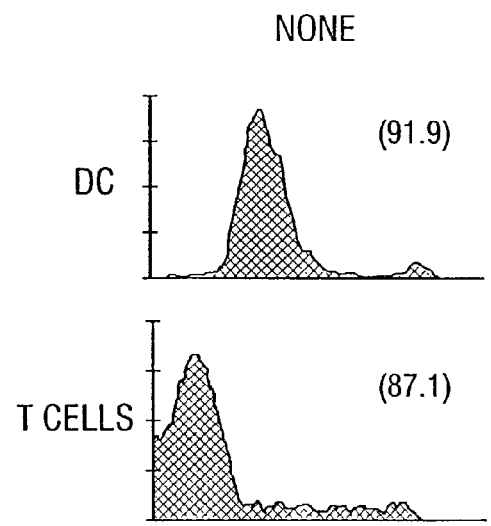
FIG. 4K, FIG. 4L and FIG. 4M. XS52 DC or HDK-1 T cells were cultured for 24 hours with anti-dectin-1 mAb 2E5 or control mAb (50% v/v) and then examined for cell viability. Data shown are the PI-labeling profiles; numbers in parentheses indicated the mean % viability from triplicate samples.
Figure 4L:
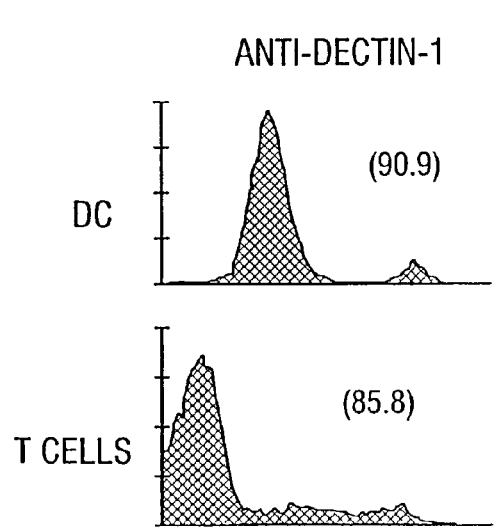
Figure 4M:
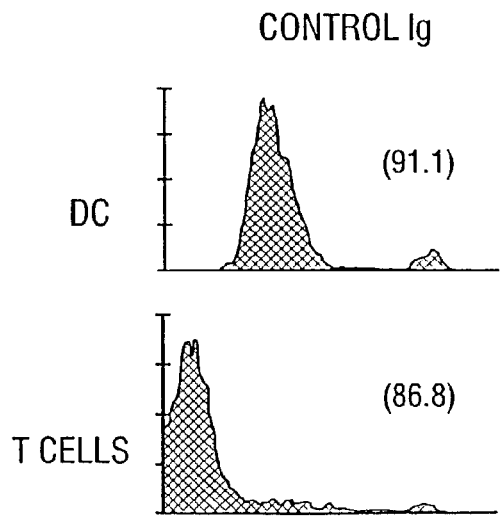

Rat antisera raised against His-dectin-1 inhibited completely the capacity of splenic DC and XS52 DC to present a protein antigen (KLH), as well as a chemical antigen (DNBS), to antigen-specific T cell clones and the T cells isolated from antigen-primed animals (FIG. 4C). These antibodies also inhibited completely their capacity to activate allogeneic T cells isolated from unprimed animals. Similar inhibition was also achieved with rabbit polyclonal anti-His-dectin-1 antibodies (BAD1-Pep).

It will, of course, be understood that all the screening methods of the present invention are useful in themselves notwithstanding the fact that effective candidates may not be found, since it would be a practical utility to know that dectin-1 or dectin-2 agonists and/or antagonists do not exist. The invention provides methods for screening for such candidates, not in finding them.

Finally, the dectin-related assays described may also be used to search for molecules that inhibit dectin-dependent signaling cascades during DC-T cell interaction. For example, one method obtained from the invention is a method for identifying an inhibitory agent, comprising admixing a dectin-1 or dectin-2 composition with a population of T cells and a candidate substance and identifying a candidate that inhibits the interaction of dectin-1 or dectin-2 with the T cells. Preferably, the dectin-1 or dectin-2 of this method will be expressed on the surface of a DC. The composition comprising dectin-1 or dectin-2 may comprise engineered cells that express recombinant dectin-1 or dectin-2; purified dectin-1 or dectin-2 operatively linked to a detectable label; or a population of DC that express dectin-1 or dectin-2.

The candidate substance that inhibits the interaction of dectin-1 or dectin-2 with T cells may be identified by inhibition of dectin-1 or dectin-2 binding to the T cells or by inhibition of dectin-1 or dectin-2 mediated activation of T cells.

More specifically, a method for identifying an inhibitory agent as disclosed herein may include the steps of: admixing a first composition comprising a population of recombinant cells expressing dectin-1 or dectin-2 with a second composition comprising a population of T cells; incubating the admixture with a candidate substance as described above; testing the admixture for DC-activation T cells; and identifying a candidate substance that inhibits the activation of T cells.

Agents that inhibit the binding of dectin-1 or dectin-2 to T cells or that inhibit dectin-1 or dectin-2-mediated activation of T cells are also contemplated as being within the invention. Preferably, the agents of the invention will be formulated in a pharmaceutical acceptable medium. The agents of the invention may be prepared by a process comprising: admixing a first composition comprising a population of recombinant cells expressing dectin-1 or dectin-2 with a second composition comprising a population of T cells; incubating the admixture with a candidate substance; testing the admixture for DC-activated T cells; and identifying a candidate substance that inhibits the activation of T cells.

Candidate molecules may also be tested for their capacity to inhibit the binding of labeled dectin-1 or dectin-2 in soluble forms to the surface of T cells (in the dectin binding assay), or to inhibit the adhesion of T cells to DC (in the DC-T cell adhesion assay). Alternatively, candidate molecules may be examined for their capacities to suppress or to enhance the expression of dectin-1 or dectin-2 by DC at mRNA or protein levels. The techniques used to test levels of dectin-1 or dectin-2 expression include northern blotting, RT-PCR™, in situ hybridization, and RNase protection assay (at RNA levels) or by ELISA, western blotting, immunoprecipitation, radioimmunoabsorption and competition assays, and immunofluorescence and immunohistochemical stainings at protein levels.

Candidate molecules may augment dectin-dependent DC-T cell interaction. To test this possibility, test samples will be added to the DC-induced T cell activation assay, the dectin-binding assay, or the DC-T cell adhesion assay. Samples that enhance the function of dectin-1 or dectin-2 in one of these assays will be considered to possess an immunoaugmentative property.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Obtaining Dectin-1

A long-term DC line established from the epidermis of newborn BALB/c mice, termed XS52, was used. mRNAs isolated from the XS52 DC line were reverse-transcribed into double-strand cDNAs, ligated unidirectionally into the lambda ZAP II vector, and packaged into phage particles. Double-stranded DNAs were then converted to single-stranded forms by co-infection with ExAssist helper phages, and single-stranded DNAs (in the anti-sense orientation) were hybridized with biotinylated mRNAs isolated from the J774 macrophage line. A subtractive cDNA library was then constructed from the unhybridized cDNAs; 50- to 200-fold enrichment was achieved by this subtraction.

cDNA isolated from the XS52 DC line was hybridized with excess mRNA from the J774 macrophage line and a library was constructed from the cDNA that remained unhybridized. A total of 12,000 clones in the subtracted library were screened sequentially by colony hybridization, slot blotting, and northern blotting. The inventors then selected 50 clones that were expressed by XS52 DC, but not J774 macrophages. Sequencing of these clones revealed 18 that encoded recognized molecules, including IL-1β, a β-chemokine C10, cathepsin C, spermidine/spermine N1-acetyltransferase, the ras-related protein Rab-2, and the hemopoietic-specific early response gene A1. On the other hand, 32 clones (6 different genes) showed no significant homologies with nucleotide sequences currently registered in the EMBL or Gene Banks.

One of these clones was of special interest, not only because it was expressed by XS52 DC in relatively large amounts and in a highly specific manner, but also because its open reading frame encoded a unique, type II membrane-integrated polypeptide. Its deduced amino acid sequence contains 244 amino acids (aa), consisting of: a) a cytoplasmic domain (aa 1–44) with a tyrosine residue at aa 15, b) a putative transmembrane domain (aa 45–68), and c) an extracellular domain (aa 69–244) (FIG. 1A). The extracellular domain contains a region (aa 119–244) that exhibits significant homology (up to 35.6% similarity) with CRDs of currently recognized C-type lectins, such as the phospholipase A2 receptor (PA2R), asialoglycoprotein receptors or hepatic lectin (HL)-1 and HL-2, CD23 (low affinity IgE receptor: FcεRII), and CD69 (early activation marker) (FIG. 1B). After comparing CRD sequences, Spiess has postulated that 13 amino acids are relatively well conserved in many C-type lectins. These invariant residues include six cysteines, which appear to play a critical role in forming disulfide bridge frameworks (Spiess 1990). Importantly, the putative CRD sequence in the inventors' polypeptide contained 11 out of 13 of these invariant residues, including all six cysteine residues (FIG. 1A). Based on these features, the inventors termed this molecule "DC-specific C-type lectin" or "dectin-1".

Example 2

DC Expression of Dectin-1

Northern blotting and RT-PCR™ were carried out as described previously (Ariizumi et al., 1995; Takashima et al. 1995). The following primers were used to amplify the dectin-1 DNA: 5'primer; 5'-AGGCCCTATGAAGAACTA-CAGACA-3' (SEQ ID NO:29) and 3'primer; 5'-AACCATG-GCCCTTCACTCTG-3' (SEQ ID NO:30). After 30 cycles of amplification, PCR™ products were hybridized with internal probes.

Figure 2B:
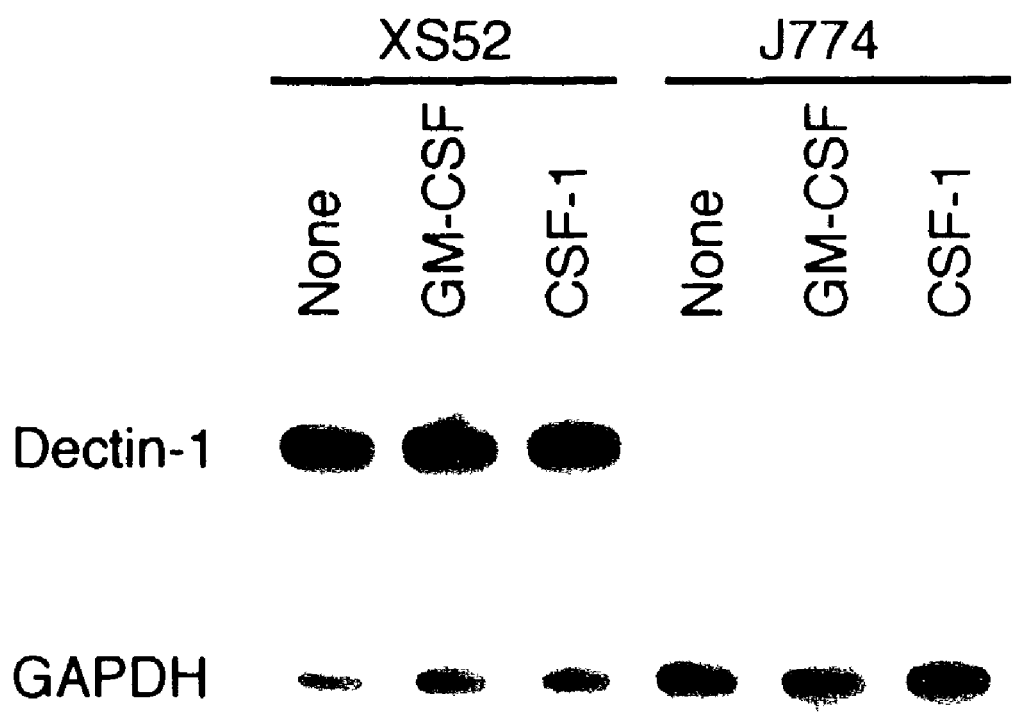
Figure 2C:
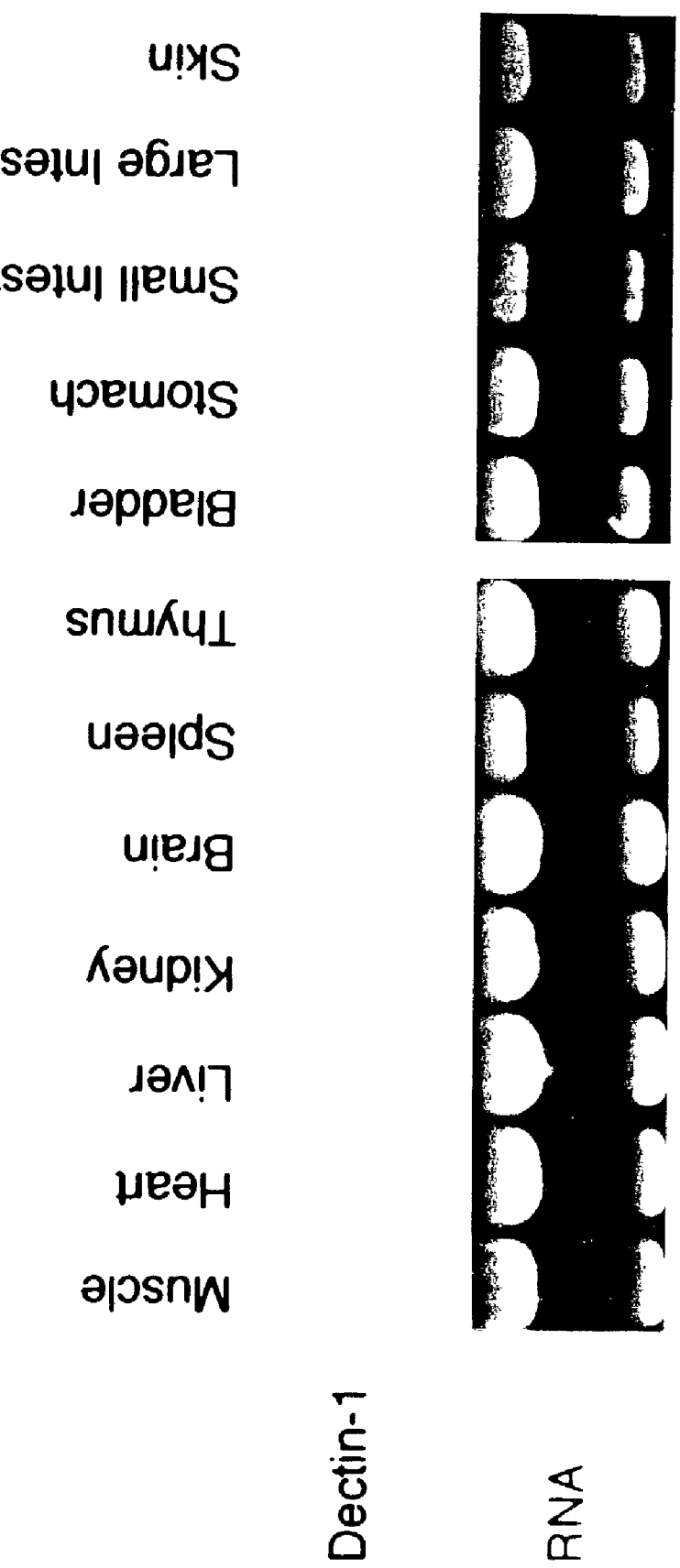

As mentioned above, dectin-1 mRNA was expressed at relatively high levels by XS52 DC, whereas it was detected at only negligible levels in J774 macrophages. To further assess expression specificity, the inventors examined a wide panel of cell lines, including two macrophage lines, a B cell hybridoma, and two αβ T cell lines. Once again, dectin-1 mRNA was expressed exclusively by the XS52 DC line (FIG. 2A). Because the XS52 line, but not other cell lines, had been expanded in the presence of GM-CSF and CSF-1 (Xu et al., 1995; Takashima et al., 1995), the inventors considered the possibility that dectin-1 might represent a gene that was inducible by these cytokines. To address this possibility, the inventors examined the influence of these cytokines on dectin-1 mRNA expression (FIG. 2B). Expression patterns remained unchanged in both XS52 cells and J774 cells, regardless of the culture conditions, suggesting that the cytokine milieu had played no significant role in dectin-1 gene expression. Moreover, the inventors observed that dectin-1 mRNA expression occurred preferentially in spleen and thymus, tissues known to contain relatively large numbers of DC (FIG. 2C). The inventors also observed that dectin-1 mRNA is expressed in relatively large amounts by splenic DC, whereas only minimal, if any, expression was detected in B220+ spleen cells (i.e., B cells) or peritoneal macrophages. Although northern blotting failed to reveal dectin-1 mRNA expression in skin, the tissue from which the XS52 line had been established, the inventors detected a strong PCR™ signal in epidermal cells freshly isolated from BALB/c mice (FIG. 2C). Depletion of the Ia+ population (i.e., Langerhans cells) depleted dectin-1 mRNA, as well as IL-1β mRNA, which is known to be expressed exclusively by Langerhans cells in murine epidermis (Matsue et al., 1992; Heufler et al., 1992; Enk et al., 1992). This corroborates the inventors' observations with cell lines; dectin-1 mRNA was detected by northern blotting in the Langerhans cell-derived line XS52, but was absent from cell lines derived from other epidermal cell populations, i.e., Pam 212 keratinocytes and 7–17 dendritic epidermal T cells (DETC) (FIG. 2A). Collectively, these results indicate that dectin-1 mRNA is expressed constitutively and specifically by DC, including Langerhans cells in skin.

Example 3

Production of Antibodies to Dectin-1

Rabbits were immunized with the synthetic polypeptide, GRNPEEKDNFLSRNKENHKP (SEQ ID NO:11), and collected serum was subjected to affinity purification using the Thiol Coupling Gel conjugated with the same polypeptide. Cells were extracted in 0.3% Triton X-100 in PBS and examined by immunoblotting with anti-peptide antibodies or rabbit IgG control as described previously (Mohamadzadeh et al., 1996). Splenic DC were surface labeled with $^{125}$I and then subjected to immunoprecipitation with anti-peptide antibodies or rabbit control antibodies as before (Kitajima et al., 1995).

Figure 3C:
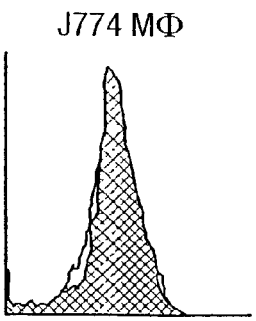
Figure 3D:
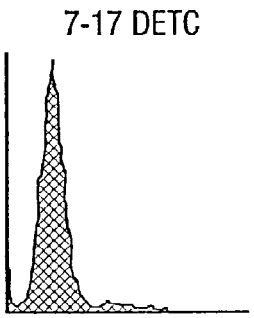
Figure 3E:
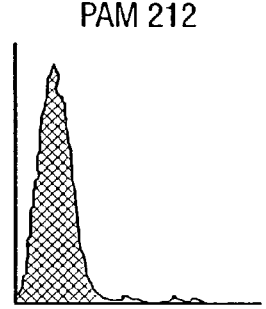
Figure 3F:
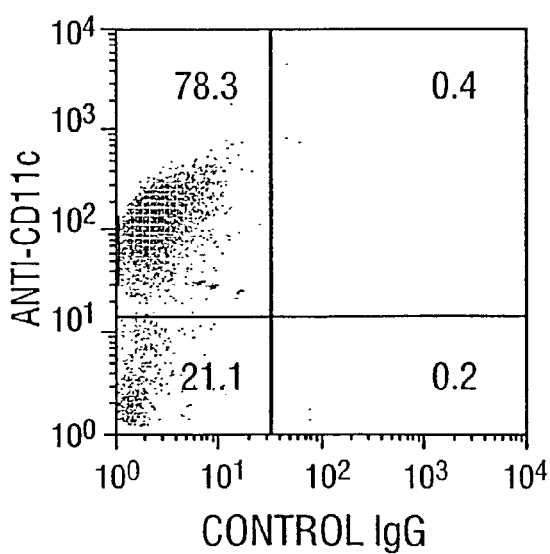
FIG. 3F and FIG. 3G. Splenic DC were isolated by standard protocol of Steinman and then examined for surface expression of dectin-1. DC were identified with anti-CD11c Mab (HL-2, purchased from PharMingen, San Diego, Calif.) in the FL-2 channel. About 80–90% of the cells were CD11c-positive (i.e., DC) and the rest of the cells were CD11c-negative (i.e., contaminating macrophages and B cells).
Figure 3G:
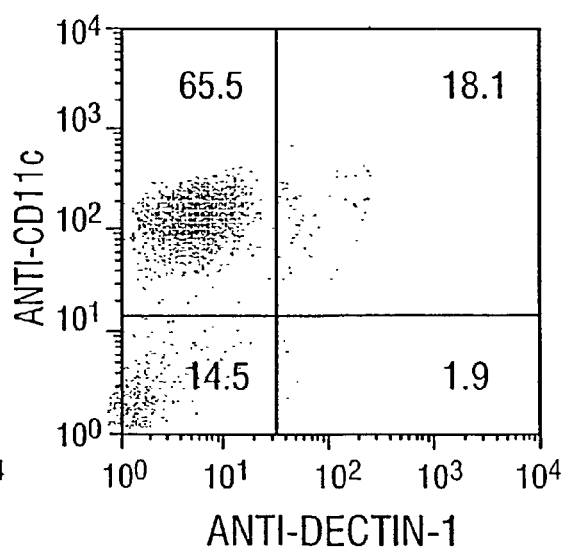

Affinity-purified antibodies (BAD1-Pep) against a synthetic polypeptide GRNPEEKDNFLSRNKENHKP (corresponding to aa 75–94) (SEQ ID NO:11) immunolabeled a major band of 41 kD in an extract of XS52 DC, but not J774 macrophages (FIG. 3A). This major band was considerably larger than the molecular weight (28 kD) predicted from the amino acid sequence of dectin-1. This discordance presumably reflects glycosylation of the native dectin-1 molecule, because its sequence contains putative N-glycosylation sites at aa 185 and 233. The same anti-peptide antibodies revealed dectin-1 on the surface of XS52 DC (FIG. 3B). By contrast, and consistent with the inventors' observations on mRNA expression, no significant antibody binding was observed for J774 macrophages, Pam 212 keratinocytes, or 7–17 DETC. Importantly, dectin-1 was expressed at significant levels by splenic DC isolated from BALB/c mice (FIG. 3B). Cell surface expression of dectin-1 was further confirmed by radio-immunoprecipitation; a 41 kD radiolabeled band was precipitated with the anti-peptide antibodies from splenic DC that had been surface labeled with $^{125}$I (FIG. 3C). Interestingly, an additional band of 29 kD, which was totally absent in western blotting (FIG. 3A), was co-precipitated with anti-peptide antibodies. In this regard, the inventors have recently identified a second molecule (dectin-2) with a predicted molecular size of 19 kD which also contains a single, but distinct, CRD and which is also expressed selectively by DC Thus, it is conceivable that the additional band may correspond to dectin-2, with the implication that dectin-1 and dectin-2 may form a heterodimer on the surface of DC. Nevertheless, these results document that dectin-1 proteins are expressed primarily by DC, and on their surfaces.

With respect to the function of dectin-1, the inventors hypothesized that it would bind to putative ligands expressed by T cells and that it would facilitate DC-T cell interaction during antigen presentation. To test this hypothesis, the inventors generated a fusion protein consisting of 6× histidine and the extracellular domain (aa 73–244) of dectin-1. This His-dectin-1 protein migrated as a single mass of 23 kD in 12.5% SDS-PAGE, corresponding with the predicted molecular size of 21 kD (FIG. 3A).

Example 4

Antibodies Against His-dectin-1 Fusion Protein

DNA sequence that encodes aa 73–244 was amplified by PCR™ and introduced into a pQE30 expression vector immediately following the histidine tag sequence. Recombinant His-dectin-1 was produced in *E. coli* and extracted in 8M urea. Recombinant proteins that remained insoluble after extensive dialysis were used to immunize rats, and the soluble proteins were used for the binding assay (α). The purity of these preparations is shown in FIG. 3A. Antigen presentation assays were conducted as described previously (Xu et al. 1995), in the presence of anti-His-dectin-1 sera or preimmune sera (1% v/v).

His-dectin-1 fusion protein showed significant binding to splenic T cells which had been freshly isolated from BALB/c mice, as revealed by FACS analysis using a monoclonal antibody (mAb) against the histidine tag (FIG. 4A). This staining, albeit relatively modest in intensity, was reproducible and specific; no detectable staining was observed with an isotype matched control IgG or in the absence of His-dectin-1. Having validated the first half of the inventors' hypothesis, the inventors next sought to determine whether DC-T cell interaction could be blocked by interfering with surface dectin-1. For this purpose, the inventors raised antibodies against recombinant His-dectin-1 (TAD1-Rhi). These antibodies inhibited completely the capacity of splenic DC and XS52 DC to present a protein antigen (KLH), as well as a chemical antigen (DNBS), to antigen-specific T cell clones and the T cells isolated from antigen-primed animals (FIG. 4B). More importantly, these antibodies also inhibited completely the capacity to activate allogeneic T cells isolated from unprimed animals, suggesting that dectin-1 mediates DC interaction with T cells, rather than the uptake of soluble antigens. This was supported further by the microscopic observation that anti-His-dectin-1 antibodies inhibited substantially antigen-specific aggregation of DC with responding T cells in the above antigen presentation assays.

In this regard, the inventors have generated a panel of MAb against recombinant His-dectin-2 proteins (produced in *E. coli*). Rats were immunized with His-dectin-2 and hybridomas were screened in western blotting for their reactivity to His-dectin-1. Resulting MAb (MAD2-Rhi) recognize not only the His-dectin-1, but also native forms of dectin-2 proteins in the extract from XS52 DC.

Example 5

Recombinant Production of Dectin-1 or Dectin-2

The nucleotide sequence encoding the extracellular domain (aa 73–244) of dectin-1 was inserted in the 3' end of the 6×His sequence of pQE30 plasmid. *E coli* were transformed with the resulting pQE30-Dec1ECD plasmid. Extracts isolated from these transfectants in 8M urea were then purified with nickel-sepharose column and then dialyzed extensively against PBS in the presence of 0.5 M L-arginine, 1 mM GSH, and 1 mM GSSG. Fractions that were solubilized during the dialysis were tested for their binding to T cells, whereas fractions that remained insoluble were injected into rats or rabbits to obtain antibodies against dectin-1. The same protocols were used to prepare His-dectin-2 that contain the extracellular domain of dectin-2. His-dectin-1 or His-dectin-2 migrated in 4–12% SDS-PAGE as a single mass of 23 kD or 18 kD, corresponding with a predicted molecular size, and was immunolabeled with either anti-dectin-1 or anti-dectin-2 antibodies, respectively.

An alternative approach was to produce chimeric proteins consisting of glutathione S-transferase (GST) (in the N-terminus) and extracellular domains of dectin-1 or dectin-2 (in the C-terminus). When these proteins were produced in *E. coli* and then extracted with high concentrations (8 M) of urea, they remained totally insoluble after dialysis against PBS. On the other hand, the investigators contemplate that the use of GST-fusion proteins may have an advantage over His-tagged proteins in the stability. Therefore, these GST-dectin-1 or GST-dectin-2 fusion proteins may prove useful as antigens for immunization.

The inventors have been able to produce recombinant dectin-1 and dectin-2 in soluble forms in mammalian cells. A DNA fragment encoding the extracellular domain of dectin-1 (nucleotides 232–820 in SEQ ID NO:1) or dectin-2 (nucleotides 296–772 in SEQ ID NO:3) was introduced into the downstream of the immunoglobulin leader sequence (pSecTagB, purchased from Invitrogen, San Diego, Calif.). The construct was then transfected into COS cells to produce secreted forms of extracellular domains of dectin-1 or dectin-2.

As a third alternative strategy, a new vector system (pMAL-c2) that directs the production of fusion proteins in a soluble form to the periplasm of bacteria (New England Biolabs, Beverly, Mass.) may be employed. The fusion partner, maltose-binding protein, will be cleaved from the extracellular domain of dectin-2 by factor Xa protease.

Example 6

Identifying Human Equivalents of Dectin-1 and/or Dectin-2

PCR™ and RT-PCR™ Amplification:

Human genomic DNA or cDNA will be amplified, under various conditions with different degrees of stringency, using primer sets designed on the basis of murine dectin-1 and dectin-2 nucleotide/amino acid sequences. PCR™ products will then be cloned and sequenced. If they exhibit significant homologies to murine dectin-1 or dectin-2 at the level of either nucleotide or amino acid, these PCR™ products will be used to clone relevant cDNA from a cDNA library prepared from human dendritic cells or peripheral blood leukocytes.

Colony Hybridization:

A cDNA library prepared from human DC or peripheral blood leukocytes or a human genomic DNA library will be hybridized under various conditions with different degrees of stringency, with murine dectin-1 or dectin-2 cDNA or targeted fragments of these cDNA. Alternatively, these libraries may be hybridized with oligonucleotides synthesized based on the sequences of murine dectin-1 and dectin-2.

In fact, the inventors have been able to detect a human equivalent of dectin-1 by Southern blotting. In those studies, RNA isolated from human peripheral blood DC were converted into cDNA by using CapFinder (Clontech, Palo Alto, Calif.). The resulting DC-derived cDNA were then hybridized with a CRD sequence of murine dectin-1 (SEQ ID NO:9). In Southern blotting under a relatively low stringent condition (1 M NaCl, 30–45% formamide, 10 dextran sulfate, at 37 C), this cDNA probe hybridized a 2.8 kb band, which most likely represent a human equivalent of dectin-1. These results indicate that murine dectin-1 and human dectin-1 show a nucleotide sequence homology that is high enough to be detectable with the nucleotide sequence of SEQ ID NO:1. Moreover, the inventors have identified, using RT-PCR™, a 172 bp DNA fragment for human dectin-1 from human peripheral blood DC. This DNA fragment (SEQ ID NO:33) exhibits 71.5% similarity in nucleotide sequence to mouse dectin-1. Moreover, this DNA fragment hybridized strongly a human dectin-1 mRNA in Northern blotting. Specifically, the inventors have detected 2.8 kb and 4.0 kb bands in human lymphoid tissues, but not in non-lymphoid tissues. These results validate that human equivalents of dectin-1 or dectin-2 are detectable with cDNA probes of mouse origin.

Use of Antibodies:

Monoclonal and polyclonal antibodies will be produced in various animal species using recombinant murine dectin-1 or dectin-2 or synthetic peptides as antigens. These antibodies will then be examined for their reactivity to human dendritic cells. Antibodies that recognize human dendritic cells will be used to identify human equivalents of dectin-1 and dectin-2. More specifically, relevant proteins will be purified by immunoprecipitation and then sequenced. cDNA encoding human equivalents will then be cloned by PCR™ and/or colony hybridization using PCR™ products (amplified with primers designed from the amino acid sequences) or oligonucleotides.

Use of Ligands of Dectin-1 or Dectin-2:

Once relevant ligands of murine dectin-1 and/or dectin-2 are identified (see Example 7), these molecules will serve as molecular probes to identify human equivalents of dectin-1 and/or dectin-2. More specifically, soluble forms of ligands for murine dectin-1 and/or dectin-2 will be first examined for their binding to the surface of human dendritic cells. If they show significant binding, the inventors will employ an expression cDNA cloning strategy, in which a non-dendritic cell line (which express no detectable dectin-1 or dectin-2) will be transfected with a cDNA library prepared from human dendritic cells (or peripheral blood leukocytes). Transfectants that bind soluble ligands (in other words, expressing human equivalents of dectin-1 or dectin-2) will be isolated by FACS or panning. This procedure will be repeated to identify the cDNA that encode human equivalents of dectin-1 and dectin-2.

Example 7

Identifying Ligands of Dectin-1 and/or Dectin-2

Expression Cloning:

The inventors will examine several different cell lines for their capacity to bind soluble forms of dectin-1 and dectin-2 (e.g., His-dectin-1 and His-dectin-2). A cell line that shows no significant binding will then be transfected with a cDNA library prepared from the HDK-1 T cell line, which shows significant binding. Transfectants that bind soluble dectin-1 and/or dectin-2 will then be isolated by FACS or panning. This procedure will be repeated to identify the cDNA that encode relevant ligands of dectin-1 and/or dectin-2. Considering the possibility that dectin-1 and dectin-2 may increase their affinity following heterodimerization, dectin-1/dectin-2 complex will be used in some studies.

Use of Random Peptide Display Library:

Mammalian cells transfected with dectin-1 and/or dectin-2 cDNA will be used to identify peptides that bind to dectin-1 and/or dectin-2. Specifically, *E. coli* expressing a random peptide display library (e.g., FliTrx™) will be screened for the binding to the above transfectants by panning. After several rounds of screening, positive clones will be sequenced. Full-length polypeptides will then be identified by colony hybridization of a T cell cDNA library using oligonucleotide or PCR™ primers synthesized based on the peptide sequence.

Biochemical Approach:

Total cell extracts or membrane fractions prepared from a T cell line will be applied onto an affinity column conjugated with soluble dectin-1 and/or dectin-2. Molecules bound to the column (i.e., putative ligands) will then be eluted by changing the pH or washing with EDTA or carbohydrates. The eluents will be purified by conventional column chromatography and HPLC and then examined for amino acid sequences. cDNA encoding these ligands will be cloned by colony hybridization of a T cell cDNA library using oligonucleotide or PCR™ primers synthesized based on the revealed amino acid sequence.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,791,932
U.S. Pat. No. 3,817,837
U.S. Pat. No. 3,850,752
U.S. Pat. No. 3,939,350
U.S. Pat. No. 3,949,064
U.S. Pat. No. 3,996,345
U.S. Pat. No. 4,174,384
U.S. Pat. No. 4,196,265
U.S. Pat. No. 4,215,051
U.S. Pat. No. 4,275,149
U.S. Pat. No. 4,277,437
U.S. Pat. No. 4,366,241
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,682,195
U.S. Pat. No. 4,683,202
*Antibodies: A Laboratory Manual*, Cold Spring Harbor Laboratory, 1988.
Ariizumi, Kitajima, Bergstresser, Takashima, *Eur. J. Immunol.*, 25:2137–2141, 1995.
Beaudet, *Am. J. Hum. Gen.*, 37:386–406, 1985.
Bittner et al., *Methods in Enzymol*, 153:516–544, 1987.
Bradley et al, *Current Topics in Developmental Biology*, 20:357–371, 1986.
Brutlag et al., *CABIOS*, 6:237–245, 1990.
Caceres-Dittmar, Ariizumi. Xu. Tapia, Bergstresser. Takashima. *Photochem. Photobiol.* 62:176–183, 1995.
Campbell, In: *Monoclonal Antibody Technology, Laboratory Techniques In Biochemistry and Molecular Biology*, Burden and Von Knippenberg, Amsterdam, Elseview. Vol. 13, pp 75–83, 1984.
Caouto, Christian, Peterson, Ceriani, *Cancer Research* (supp.), 55:5973s–5977s, 1995.
Capaldi et al. *Biochem. Biophys Res. Comm.*, 76:425 1977.
Caux, Massacrier, Vanbervliet et al, *J. Exp. Med.*, 180: 1263–1272, 1994.
Chou and Fasman, *Adv. Enzymol. Relat. Areas Mol. Biol.*, 47:45–148, 1978a.
Chou and Fasman, *Ann. Rev. Biochem.*, 47:251–276, 1978b.
Chou and Fasman, *Biophys. J*, 26:367–384, 1979.
Chou and Fasman, *Biochemistry*, 13(2):222–245, 1974a.
Chou and Fasman, *Biochemistry*, 13(2):211–222, 1974b.
Co, Baker, Bednavik, Janzek, Noruda, Mayer, Plot, Stumper, Vesquez, Queen, Loibner, *Cancer Research*, 56:1118–1125, 1996.
Co, Avdalovic, Caron, Avdalovic, Scheinberg, Queen, *J. Immunology*, 138:1149–1154, 1992.
Colberre-Garapin et al., *J. Mol. Biol.*, 150:1, 1981.
Enk and Katz, *Proc. Natl. Acad. Sci. USA*, 89; 1398–1402, 1992.
Ezekomitz et al., 1990
Ezekomitz et al., 1991.
Fetrow and Bryant, *Biotechnology*, 11:479–483, 1993.
Flam, JOURNAL, VOL: PAGES?, 1994.
Gefter et al., *Somatic Cell Genet.*, 3:231–236, 1977
Goding, In: *Monoclonal Antibodies: Principles and Practice,* 2d ed., Orlando, Fla., Academic Press, pp. 60–61, 65–66, 71–74, 1986.
Hess et al., *J. Adv. Enzyme Reg.*, 7:149, 1968.
Heufler, Topar, Koch, et al., *J. Exp. Med.*, 176:1221–1226, 1992.
Hitzeman et al, *J. Biol. Chem.*, 255:2073, 1980.
Hogan et al, *Manipulating the Mouse Embryo: A Laboratory Manual*, Cold Spring Harbor Laboratory Press, Cold Spring Harbor, N.Y., 1986.

Holland et al, *Biochemistry*, 17:4900, 1978.
Hoover et al., (eds). "Remington's Pharmaceutical Sciences," 15th Ed., pp. 1035–1038 and 1570–1580, Mark Publishing Co., Barton, Pa., 1975.
Hopp, U.S. Pat. No. 4,554,101
Inaba, Swiggard, Inaba et al, *Cell. Immunol.*, 163:148–156, 1995.
Jameson and Wolf, *Comput. Appl. Biosci.*, 4(1):181–186, 1988.
Jiang, Swiggard, Heufler et al., *Nature*, 375:151–155, 1995.
Johnson et al., *Biotechnology and Pharmacy*, Pezzuto et al., eds., Chapman and Hall, New York, 1993.
Jones, *Genetics*, 85:12, 1977.
Kery, 1991.
Kingsman et al., JOURNAL, VOL: PAGES?, 1979.
Kijimoto-Ochiai et al., 1994.
Kitajima, Ariizumi, Mohamadzadeh, Edelbaum, Bergstresser, Takashima, *J. Immunol.*, 155:3794–3800, 1995.
Kohler and Milstein, *Eur. J. Immunol.*, 6:511–519, 1976.
Kholer and Milstein, *Nature*, 256:495–497, 1975.
Kyte and Doolittle, *J. Mol. Biol.*, 157:105–132, 1982.
Lovell-Badge, In: *Teratocarcinomas and Embryonic Stem Cells: A Practical Approach*, E. J. Robertson, ed., IRL Press, Washington D.C., 1987.
Lowry et al., *Cell*, 22:817, 1980.
Matsue, Cruz, Bergstresser, Takashima, *J. Invest. Dermatol.*, 99:537–541, 1992.
Mohamadzadeh, Poltorak, Bergstresser, Beutler, Takashima, *J. Immunol.*, 156:3102–3106, 1996.
Mulligan et al., *Proc. Natl. Acad. Sci. USA*, 78:2072, 1981.
Nakamura et al., "Enzyme Immunoassays: Heterogeneous and Homogeneous Systems." Chapter 27, 1987.
O'Hare et al., *Proc. Natl. Acad. Sci. USA*, 78; 1527, 1981.
Oldenburg et al., 1992.
Reid et al., 1994.
Robertson, *Teratocarcinomas and Embryonic Stem Cells: A Practical Approach*, E. J. Robertson, ed., IRL Press, Washington D.C., 1987.
Sallusto, Cella, Danieli, Lanzavecchi, *J. Exp. Med.*, 182:389–400, 1995.
Sambrook, Fritsch, Maniatis, *Molecular Cloning, A Laboratory Manual*, 2nd ed., 1989.
Sancar, Valdineso, Borders, Yao, Raval, Madan, Sreepatni, Shimoyami, Steiger, Visscher, *Diagnostic Molecular Patholgy*, 4:266–273, 1995.
Santerre et al., *Gene*, 30: 147, 1984.
Schreiber, Kilgus, Payer et al., *J. Immunol.*, 149:3525–3534, 1992.
Spiess, *Biochemistry*, 29:10009–10018, 1990.
Stahl, *Current Opinion in Immunology*, 4:49–52, 1992.
Steinman and Swanson, *J. Exp. Med.*, 182:283–288, 1995.
Steinman, *Ann. Rev. Immunol.*, 9:271–296, 1991.
Steinman, Inaba, Schuler, In: *The Immune Functions of Epidermal Langerhans Cells*, (ed. Heidrun Moll), R. G. Landes Company, Austin, Tex., 1–19, 1995.
Stinchcomb et al., *Nature*, 282:39, 1979.
Szybalska et al., *Proc. Natl. Acad. Sci. USA*, 48:2026, 1962.
Takashima, Edelbaum, Kitajima et al., *J. Immunol*, 154:5128–5135, 1995.
Tschemper et al., *Gene*, 10: 157, 1980.
Vassa et al., 1994.
Vercelli et al., 1989.
Weinberger et al., *Science*, 228:740–742, 1985.
Wigler et al., *Cell*, 11:223, 1977.
Wigler et al., *Proc. Natl. Acad. Sci. USA*, 77:3567, 1980.
Witmer-Pack, Swiggard, Mirza, Inaba, Steinman, *Cell. Immunol.*, 163:157–162, 1995.
Wolf et al., *Comput. Appl. Biosci.*, 4(1):187–191, 1988.
Xu, Ariizumi, Caceres-Dittmar et al., *J. Immunol.* 154:2697–2705, 1995.
Xu, Ariizumi, Edelbaum, Bergstresser, Takashima, *Eur. J. Immunol.*, 25:1018–1024, 1995.

What is claimed is:

1. A method of identifying an effector of dendritic cell (DC) interaction with T cells comprising the steps of (a) admixing a purified mouse T cell-binding dectin-1 or dectin-2 composition with a T cell and a candidate substance, and (b) determining if the candidate substance alters the interaction of mouse dectin-1 or dectin-2 with the T cell, wherein a candidate substance that alters the interaction of mouse dectin-1 or dectin-2 with the T cell is an effector of dendritic cell interaction.

2. The method of 1, wherein said mouse dectin-1 or dectin-2 composition comprises purified mouse dectin-1 or dectin-2 linked to a detectable label.

3. The method of claim 1, wherein a candidate substance that affects the interaction of mouse dectin-1 or dectin-2 with the T cell is identified by an alteration in mouse dectin-1 or dectin-2 composition binding to the T cell.

4. The method of claim 1, wherein a candidate substance that affects the interaction of mouse dectin-1 or dectin-2 composition with the T cell is identified by an alteration in mouse dectin-1-mediated or dectin-2-mediated activation of the T cell.

5. The method of claim 1, wherein said effector stimulates the interaction of mouse dectin-1 or dectin-2 with T cells.

6. The method of claim 1, wherein said effector inhibits the interaction of mouse dectin-1 or dectin-2 with T cells.

7. A method of identifying a T cell inhibitory agent comprising the steps of:
(a) admixing a composition comprising a recombinant cell comprising a mouse dectin-1 or dectin-2 transgene and expressing mouse dectin-1 or dectin-2 peptide or polypeptide that binds T cells with a T cell;
(b) incubating the admixture of step (a) with a candidate substance; and
(c) assessing activation of the T cell,
wherein a reduction in activation of the T cell in the presence of the candidate substance, as compared to activation observed in the absence of the candidate substance, identifies the candidate substance as a T cell inhibitory agent.

8. A method of identifying a T cell stimulatory agent comprising the steps of:
(a) admixing a composition comprising a recombinant cell comprising a mouse dectin-1 or dectin-2 transgene and expressing mouse dectin-1 or dectin-2 peptide or polypeptide that binds T cells with a T cell;
(b) incubating the admixture of step (a) with a candidate substance; and
(c) assessing activation of the T cell,
wherein an increase in activation of the T cell in the presence of the candidate substance, as compared to activation observed in the absence of the candidate substance, identifies the candidate substance as a T cell stimulatory agent.

* * * * *

UNITED STATES PATENT AND TRADEMARK OFFICE
CERTIFICATE OF CORRECTION

| | |
|---|---|
| PATENT NO. | : 7,129,039 B2 |
| APPLICATION NO. | : 10/201060 |
| DATED | : October 31, 2006 |
| INVENTOR(S) | : Ariizumi et al. |

Page 1 of 1

It is certified that error appears in the above-identified patent and that said Letters Patent is hereby corrected as shown below:

Column 141, line 23, after "method of", insert --claim --therefor.

Signed and Sealed this

Thirteenth Day of February, 2007

JON W. DUDAS
*Director of the United States Patent and Trademark Office*